(12) United States Patent
Zhang et al.

(10) Patent No.: US 11,535,845 B2
(45) Date of Patent: Dec. 27, 2022

(54) AUTOMATED SCREENING OF ENZYME VARIANTS

(71) Applicant: Codexis, Inc., Redwood City, CA (US)

(72) Inventors: Xiyun Zhang, Fremont, CA (US); Russell Javiniar Sarmiento, Redwood City, CA (US); Donald Scott Baskerville, Burlingame, CA (US); Gjalt W. Huisman, Redwood City, CA (US)

(73) Assignee: Codexis, Inc., Redwood City, CA (US)

( * ) Notice: Subject to any disclaimer, the term of this patent is extended or adjusted under 35 U.S.C. 154(b) by 431 days.

(21) Appl. No.: 16/875,848

(22) Filed: May 15, 2020

(65) Prior Publication Data

US 2020/0277597 A1    Sep. 3, 2020

Related U.S. Application Data

(62) Division of application No. 14/498,864, filed on Sep. 26, 2014, now Pat. No. 10,696,964.

(60) Provisional application No. 61/883,838, filed on Sep. 27, 2013.

(51) Int. Cl.
  *C12N 15/10*   (2006.01)
  *G16C 20/60*   (2019.01)
  *G16B 35/00*   (2019.01)
  *G16B 35/20*   (2019.01)

(52) U.S. Cl.
  CPC ..... *C12N 15/1089* (2013.01); *C12N 15/1058* (2013.01); *G16B 35/00* (2019.02); *G16B 35/20* (2019.02); *G16C 20/60* (2019.02)

(58) Field of Classification Search
  None
  See application file for complete search history.

(56) References Cited

U.S. PATENT DOCUMENTS

| | | |
|---|---|---|
| 6,969,763 B1 | 11/2005 | Ecker et al. |
| 7,747,393 B2 | 6/2010 | Fox |
| 8,762,066 B2 | 6/2014 | Fox |
| 10,696,964 B2 | 6/2020 | Zhang et al. |
| 11,342,046 B2 | 5/2022 | Sarmiento et al. |
| 2002/0099506 A1 | 7/2002 | Floriano et al. |
| 2002/0133297 A1 | 9/2002 | Yang et al. |
| 2006/0099667 A1 | 5/2006 | Andre et al. |
| 2006/0121455 A1 | 6/2006 | Goddard et al. |
| 2006/0136184 A1 | 6/2006 | Gustafsson et al. |
| 2009/0118130 A1 | 5/2009 | Mundorff et al. |
| 2014/0303952 A1 | 10/2014 | Wang et al. |
| 2015/0133307 A1 | 5/2015 | Zhang et al. |
| 2015/0134315 A1 | 5/2015 | Sarmiento et al. |
| 2016/0136184 A1 | 5/2016 | DeLuca et al. |
| 2020/0020415 A1 | 1/2020 | Sarmiento et al. |
| 2022/0238179 A1 | 7/2022 | Sarmiento et al. |

FOREIGN PATENT DOCUMENTS

| | | |
|---|---|---|
| CN | 1468959 A | 1/2004 |
| CN | 101484462 A | 7/2009 |
| CN | 102156823 A | 8/2011 |
| CN | 102164952 A | 8/2011 |
| CN | 102939383 A | 2/2013 |
| CN | 103265635 A | 8/2013 |
| CN | 103324861 A | 9/2013 |
| EP | 2 216 429 A1 | 8/2010 |
| JP | 04-179495 A | 6/1992 |
| JP | 2005-309877 A | 11/2005 |
| JP | 2009-525274 A | 7/2009 |
| KR | 20080099278 A | 11/2008 |
| RU | 2008 140 858 A | 4/2010 |
| RU | 2453911 C2 | 6/2012 |
| WO | WO 2006/044378 A2 | 4/2006 |
| WO | WO 2006/121455 A1 | 11/2006 |
| WO | WO 2007/087266 A2 | 8/2007 |
| WO | WO 2010/077470 A2 | 7/2010 |
| WO | WO 2015/048572 A1 | 4/2015 |
| WO | WO 2015/048573 A1 | 4/2015 |

OTHER PUBLICATIONS

US Office Action dated Nov. 17, 2016 issued in U.S. Appl. No. 14/498,864.
US Final Office Action dated May 15, 2017 issued in U.S. Appl. No. 14/498,864.
US Office Action dated May 18, 2018 issued in U.S. Appl. No. 14/498,864.
US Final Office Action dated Dec. 13, 2018 issued in U.S. Appl. No. 14/498,864.

(Continued)

*Primary Examiner* — Michael L Borin
(74) *Attorney, Agent, or Firm* — Weaver Austin Villeneuve & Sampson LLP

(57) ABSTRACT

Disclosed are methods for identifying bio-molecules with desired properties (or which are most suitable for a round of directed evolution) from complex bio-molecule libraries or sets of such libraries. Some embodiments of the present disclosure provide methods for virtually screening proteins for beneficial properties. Some embodiments of the present disclosure provide methods for virtually screening enzymes for desired activity and/or selectivity for catalytic reactions involving particular substrates. Some embodiments combine screening and directed evolution to design and develop proteins and enzymes having desired properties. Systems and computer program products implementing the methods are also provided.

20 Claims, 12 Drawing Sheets

(56) References Cited

OTHER PUBLICATIONS

US Office Action dated Aug. 1, 2019 issued U.S. Appl. No. 14/498,864.
US Notice of Allowance dated Apr. 9, 2020 issued in U.S. Appl. No. 14/498,864.
US Office Action dated Jun. 20, 2016 issued in U.S. Appl. No. 14/498,881.
US Final Office Action dated Nov. 18, 2016 issued in U.S. Appl. No. 14/498,881.
US Office Action dated Dec. 14, 2017 issued in U.S. Appl. No. 14/498,881.
US Final Office Action dated Jun. 19, 2018 issued in U.S. Appl. No. 14/498,881.
US Office Action dated Aug. 1, 2019 issued U.S. Appl. No. 14/498,881.
US Office Action dated Jan. 16, 2020 issued in U.S. Appl. No. 16/434,138.
Australian Examination Report dated Aug. 7, 2019 issued in AU 2014324669.
Brazil First Office Action and Written Opinion dated Mar. 17, 2020 issued in BR 1120160062850.
PCT International Search Report and Written Opinion dated Dec. 9, 2014 issued in PCT/US2014/057899.
PCT International Preliminary Report on Patentability and Written Opinion dated Apr. 7, 2016 issued in PCT/US2014/057899.
European Examination Report dated Jun. 12, 2017 issued in Application No. EP 14781426.3.
Extended European Search Report dated Sep. 20, 2018 issued in Application No. EP 18187438.9.
Japanese First Office Action dated Sep. 19, 2018 issued in Application No. JP 2016-516874.
Japanese Second Office Action dated Apr. 26, 2019 issued in Application No. JP 2016-516874.
Japanese First Office Action dated Feb. 21, 2020 issued in Application No. JP 2018-237169.
New Zealand First Examination Report dated Mar. 12, 2020 issued in Application No. NZ 717658.
Russian First Office Action dated Mar. 17, 2017 issued in Application No. RU 2016116253.
Russian Second Office Action dated Aug. 30, 2017 issued in Application No. RU 2016116253.
Russian Third Office Action dated Jan. 16, 2018 issued in Application No. RU 2016116253.
Russian Fourth Office Action dated Jul. 26, 2018 issued in Application No. RU 2016116253.
Russian Fifth Office Action dated Oct. 25, 2018 issued in Application No. RU 2016116253.
Singapore Written Opinion dated Jan. 20, 2017 issued in Application No. SG 11201601695W.
Singapore Second Written Opinion dated Oct. 25, 2017 issued in Application No. SG 11201601695W.
Chinese First Office Action dated Nov. 30, 2017 issued in Application No. CN 201480065215.X.
Chinese Second Office Action dated Sep. 26, 2018 issued in Application No. CN 201480065215.X.
Chinese Third Office Action dated May 22, 2019 issued in Application No. CN 201480065215.X.
Australian Examination Report dated Mar. 22, 2019 issued in Application No. AU 2014324670.
Brazil First Office Action/Written Opinion dated Nov. 12, 2019 issued in Application No. BR 1120160062841.
Chinese First Office Action dated Jan. 17, 2018 issued in Application No. CN 201480065176.3.
European First Office Action dated May 23, 2018 issued in Application No. EP 14786396.3.
European Office Action dated Oct. 25, 2018 issued in Application No. EP 14786396.3.
Israel First Office Action dated Jun. 30, 2019 issued in Application No. IL 244457.
PCT International Search Report and Written Opinion dated Jan. 23, 2015 issued in PCT/US2014/057900.
PCT International Preliminary Report on Patentability and Written Opinion dated Apr. 7, 2016 issued in PCT/US2014/057900.
Singapore Written Opinion dated Oct. 26, 2016 issued in Application No. SG 11201601692P.
Israel First Office Action dated Sep. 16, 2018 issued in Application No. IL 244458.
Japanese Office Action dated Jul. 26, 2017 issued in Application No. JP 2016-516871.
New Zealand First Examination Report dated Aug. 14, 2019 issued in Application No. NZ 717647.
New Zealand Further Examination Report dated Mar. 17, 2020 issued in Application No. NZ 717647.
Russian First Office Action dated Mar. 1, 2018 issued in Application No. RU 2016116261.
Russian Second Office Action dated Jul. 30, 2018 issued in Application No. RU 2016116261.
Russian Third Office Action dated Dec. 18, 2018 issued in Application No. RU 2016116261.
Chaparro-Riggers, et al. (2007) "Better library design: data-driven protein engineering," *Biotechnol. J.*, 2:180-191.
Ferreira P., et al. (2006) "Site-directed mutagenesis of selected residues at the active side of aryl-alcohol oxidase, an H2O2-producing ligninolytic enzyme," The FEBS Journal, vol. 273, No. 21, pp. 4878-4888.
Fox, et al. (2005) "Directed molecular evolution by machine learning and the influence of nonlinear interactions," *Journal of Theoretical Biology*, 234:187-199.
Fox, et al. (2007) "Improving catalytic function by ProSAR-driven enzyme evolution," *Nature Biotechnology*, 25(3):338-344.
Hecht, et al. (2011) "Applications of Machine Learning and Computational Intelligence to Drug Discovery and Development" Drug Development Research, vol. 72, pp. 53-65.
Hediger, et al. (2012) "A Computational Methodology to Screen Activities of Enzyme Variants," *PLOS ONE*, 7(12):10pp.
Hediger, et al. (Aug. 29, 2013) "In silico screening of 393 mutants facilitates enzyme engineering of amidase activity in CalB," *PeerJ*, vol. 1, 15pp [DOI 10.7717/peerj.145].
Hermann, et al. "Structure-based activity prediction for an enzyme of unknown function," Nature, vol. 448, No. 7155, Aug. 16, 2007, pp. 775-779.
Imberty, et al. "Molecular modelling of protein-carbohydrate interactions. Docking of monosaccharides in the binding site of concanavalin A," Glycobiology, vol. 1, No. 6, (1991) pp. 631-642, <doi:10.1093/glycob/1.6.631>.
Juhl, et al. "Modeling substrate specificity and enantioselectivity for lipases and esterases by substrate-imprinted docking," BMC Structural Biology, vol. 9, No. 39, Jun. 3, 2009, pp. 1-17, <doi: 10.1186/1472-6807-9-39>.
Kuchner, et al. (Dec. 1997) "Directed evolution of enzyme catalysts," *Tibtech*, 15:523-530.
Mizutani, et al. "Efficient Method for High-Throughput Virtual Screening Based on Flexible Docking: Discovery of Novel Acetylcholinesterase Inhibitors," Journal of Medicinal Chemistry, vol. 47, No. 20, Aug. 28, 2004, pp. 4818-4828. <doi:10.1021/jm030605g>.
Murphy, et al. "An active role for machine learning in drug development" Nature Chemical Biology, vol. 7, Jun. 2011, pp. 327-330.
Ning, et al. (2011) "In Silico Structure-Activity-Relationship (SAR) Models From Machine Learning: A Review," Drug Development Research, vol. 72, pp. 138-146.
Schneidman-Duhovny, et al., "PatchDock and SymmDock: servers for rigid and symmetric docking," Nucleic Acids Research, vol. 33, (2005) pp. W363-W367. <doi:10.1093/nar/gki481>.
Sirin, et al. (2014) "A Computational Approach to Enzyme Design: Predicting co-Aminotransferase Catalytic Activity Using Docking and MM-GBSA Scoring," *Journal of Chemical Information and Modeling*, 54(8):2334-2346.
Sonawane, et al. "In Silico mutagenesis and docking studies of active site residues suggest altered substrate specificity and possible

(56) References Cited

OTHER PUBLICATIONS physiological role of Cinnamoyl CoA Reductase 1 (L1-CCRH1)," Bioinformation vol. 9, No. 5, Mar. 2, 2013, pp. 224-232, <ISSN 0973-2063>.
Trott, et al. "AutoDock Vina: improving the speed and accuracy of docking with a new scoring function, efficient optimization and multithreading," J. Comput. Chem., vol. 31, No. 2, Jan. 30, 2010, pp. 455-461, <doi:10.1002/jcc.21334>.
Vieth, et al. (1998) "Assessing Energy Functions for Flexible Docking," *Journal of Computational Chemistry*, 19(14): 1612-1622.
Vieth, et al. (1998) "Assessing Search Strategies for Flexible Docking," *Journal of Computational Chemistry*, 19(14): 1623-1631.
Vilar, et al. (2012) "Predicting Biological Activities through QSAR Analysis and Docking-based Scoring," Methods Mol. Biol., vol. 914, pp. 271-284. <doi: 10.1007/978-1-62703-023-6_16>.
Wu, et al. (2003) "Detailed Analysis of Grid-Based Molecular Docking: A Case Study of CDOCKER-A CHARMm-Based MD Docking Algorithm," *Journal of Computational Chemistry*, 24(13):1549-1562.
Yang, et al. (2004) "GEMDOCK: A Generic Evolutionary Method for Molecular Docking," Proteins: Structure, Function, and Bioinformatics, vol. 55, pp. 288-304.
BR Office Action dated Apr. 28, 2022, in Application No. BR1120160062850.
Canadian First Examination Report dated Aug. 24, 2021 issued in CA 2,923,755.
Canadian First Office Action dated Jul. 23, 2020 issued in Application No. CA 2923758.
Canadian Second Office Action dated Apr. 21, 2021 issued in Application No. CA 2,923,758.
David P. Nannemann et al., "Assessing directed evolution methods for the generation of biosynthetic enzymes with potential in drug biosynthesis" Future Med Chem. vol. 3, pp. 803-819 (May 2011).
Fang Zheng et al., "Computational Modeling of Solvent Effects on Protein-Ligand Interactions Using Fully Polarizable Continuum Model and Rational Drug Design" Commun. Comput. Phys. vol. 13 (Jan. 2013).
India First Office Action dated Jul. 8, 2020 issued in Application No. IN 201647013534.
Indian First Office Action dated Jul. 11, 2020 issued in Application No. IN 201647013558.
Japanese Final Office Action [no-translation] dated Jan. 29, 2021 issued in Application No. JP 2018-237169.
Japanese Third Office Action dated Oct. 30, 2020 issued in Application No. JP 2016-516874.
JP Office Action dated Jul. 4, 2022, in Application No. JP2021-89944.
Korean First Office Action dated Nov. 24, 2020 issued in Application No. KR 10-2016-7010661.
Korean First Office Action dated Sep. 18, 2020 issued in Application No. KR 10-2016-7010659.
Korean Notice of Allowance dated Sep. 14, 2021 issued in Application No. KR 10-2016-7010659.
Korean Second Office Action dated May 25, 2021 issued in Application No. KR 10-2016-7010661.
Korean Second Office Action [no-translation] dated Mar. 23, 2021 issued in Application No. KR 10-2016-7010659.
New Zealand Second Examination Report dated Sep. 24, 2020 issued in Application No. NZ 717658.
U.S. Final Office Action dated Jun. 9, 2020 issued in U.S. Appl. No. 16/434,138.
U.S. Notice Of Allowance dated Jan. 13, 2022, in U.S. Appl. No. 16/434,138.
U.S. Office Action dated Jun. 28, 2021 issued in U.S. Appl. No. 16/434,138.

Native Reaction and Selectivity

Mechanism of catalysis and selectivity

Desired Reaction and Selectivity

Various types of Constraints

Positional Constraint    Distance Constraint    Angle Constraint    Torsion Constraint

AUTOMATED SCREENING OF ENZYME VARIANTS

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

Protein design has long been known to be a difficult task if for no other reason than the combinatorial explosion of possible molecules that constitute searchable sequence space. The sequence space of proteins is immense and is impossible to explore exhaustively using methods currently known in the art, which are often limited by the time and cost required to identify useful polypeptides. Part of the problem arises from the great number of polypeptide variants that must be sequenced, screened and assayed. Directed evolution methods increase the efficiency in honing in on the candidate biomolecules having advantageous properties. Today, directed evolution of proteins is dominated by various high throughput screening and recombination formats, often performed iteratively.

Various computational techniques have also been proposed for exploring sequence-activity space. Relatively speaking, these techniques are in their infancy and significant advances are still needed. Accordingly, new methods for improving the efficiency of screening, sequencing, and assaying candidate biomolecules are highly desirable.

SUMMARY

The present disclosure relates to the fields of molecular biology, molecular evolution, bioinformatics, and digital systems. Systems, including digital systems, and system software for performing these methods are also provided. Methods of the present disclosure have utility in the optimization of proteins for industrial and therapeutic use. The methods and systems are especially useful for designing and developing enzymes having desired activity and selectivity for catalytic reactions of particular substrates.

Certain aspects of the present disclosure relate to methods for virtually screening proteins having beneficial properties and/or guiding directed evolution programs. The disclosure presents methods for identifying bio-molecules with desired properties (or which are most suitable for directed evolution toward such properties) from complex bio-molecule libraries or sets of such libraries. Some embodiments of the present disclosure provide methods for virtually screening enzymes for desired activity and selectivity for catalytic reactions on particular substrates. Some embodiments combine screening and directed evolution to design and develop proteins and enzymes having desired properties. Systems and computer program products implementing the methods are also provided.

Some embodiments of the disclosure provide methods for screening a plurality of different enzyme variants for activity with a substrate. In some embodiments, the method is implemented using a computer system that includes one or more processors and system memory. The method includes: (a) for each enzyme variant, docking, by the computer system, a computational representation of the substrate to a computational representation of an active site of the enzyme variant, wherein docking (i) generates a plurality of poses of the substrate in the active site, and (ii) identifies energetically favorable poses of the substrate in the active site; (b) for each energetically favorable pose, determining whether the pose is active, wherein an active pose meets one or more constraints for the substrate to undergo catalysis in the active site; and (c) selecting at least one of the enzyme variants determined to have one or more active poses.

In some embodiments, the constraints include one or more of the following: position, distance, angle, and torsion constraints. In some embodiments, the constraints include a distance between a particular moiety on the substrate and a particular residue or residue moiety in the active site. In some embodiments, the constraints include a distance between a particular moiety on the ligand and an ideally positioned native ligand in the active site.

In some embodiments, the computational representation of the substrate represents a species along the reaction coordinate for the enzyme activity. The species is selected from the substrate, a reaction intermediate of the substrate, or a transition state of the substrate. In some embodiments, the variants screened are selected from a panel of enzymes that can turn over multiple substrates and wherein the members of the panel possess at least one mutation relative to a reference sequence. In some embodiments, at least one mutation is a single-residue mutation. In some embodiments, at least one mutation is in the active site of the enzyme. In some embodiments, the plurality of variants include one or more enzymes that can catalyze a chemical reaction selected from ketone reduction, transamination, oxidation, nitrile hydrolysis, imine reduction, enone reduction, acyl hydrolysis, and halohydrin dehalogenation. In some embodiments, the enzyme is selected from ketone reductase, transaminase, cytochrome P450, Baeyer-Villiger monooxygenase, monoamine oxidase, nitrilase, imine reductase, enone reductase, acylase, and halohydrin dehalogenase. However, it is not intended that the present invention be limited to any particular enzyme or class of enzyme, as any suitable enzyme finds use in the methods of the present invention. In some embodiments, the variants are members of library produced by one or more rounds of directed evolution in vitro and/or in silico.

In some embodiments, the method screens at least about ten different variants. In other embodiments the method screens at least about a thousand different variants.

In some embodiments, the computational representations of active sites are provided from 3-D homology models for the plurality of variants. In some embodiments, methods are provided for producing the 3-D homology models for protein variants. In some embodiments, the method is applied to screen a plurality of substrates.

Some embodiments provide method for identifying the constraints for the substrate to undergo the catalyzed chemical transformation by identifying one or more poses of a native substrate, a reaction intermediate of the native substrate, or a transition state of the native substrate when the native substrate undergoes the catalyzed chemical transformation by a wild-type enzyme.

Some embodiments provide method for applying a set of one or more enzyme constraints to the plurality of enzyme variants, wherein the one or more enzyme constraints are similar to the constraints of a wild-type enzyme when a native substrate undergoes a catalyzed chemical transformation in the presence of the wild-type enzyme.

In some embodiments, the plurality of poses of the substrate is obtained by docking operations including one or more of the following: high temperature molecular dynamics, random rotation, refinement by grid-based simulated annealing, and a final grid-based or full force field minimization. In some embodiments, the plurality of poses of the ligand comprises at least about 10 poses of the substrate in the active site.

In some embodiments, the selecting of variants in (c) above involves identifying variants determined to have large numbers of active poses by comparison to other variants. In some embodiments, the selecting in (c) involves ranking the variants by one or more of the following: the number of active poses the variants have, docking scores of the active poses, and binding energies of the active poses. Then variants are selected based on rank. In some embodiments, the docking scores are based on van de Waals force and electrostatic interaction. In some embodiments, the binding energies are based on one or more of the following: van der Waals force, electrostatic interaction, and solvation energy.

In some embodiments, the screening method also involves preparing a plurality of oligonucleotides containing or encoding at least a portion of at least one selected variant. The method further involves performing one or more rounds of directed evolution using the plurality of oligonucleotides. In some embodiments, preparing a plurality of oligonucleotides involves synthesizing the oligonucleotides using a nucleic acid synthesizer. In some embodiments, performing one or more rounds of directed evolution comprises fragmenting and recombining the plurality of oligonucleotides. In some embodiments, performing one or more rounds of directed evolution involves performing saturation mutagenesis on the plurality of oligonucleotides.

In some embodiments, the screened enzyme variant has desired catalytic activity and/or selectivity. The method of some embodiments also involves synthesizing the enzyme selected from screening.

In some embodiments, the screening method can be expanded to screen biomolecules other than enzymes. Some embodiments provide a method for screening a plurality of protein variants for interaction with a ligand. The method involves: (a) for each protein variant, docking, by the computer system, a computational representation of the ligand to a computational representation of an active site of the enzyme variant, wherein docking (i) generates a plurality of poses of the ligand in the active site, and (ii) identifies energetically favorable poses of the ligand in the active site; (b) for each energetically favorable pose, determining whether the pose is active, wherein an active pose meets one or more constraints for the ligand to undergo a particular interaction with protein variant; and (c) selecting at least one of the protein variants determined to have one or more active poses. In some embodiments, the ligand can be selected from a substrate, an intermediate, a transition state, a product, an inhibitor, an agonist, and/or an antagonist.

In some embodiments, computer program products and computer systems implementing the methods for screening enzymes and proteins are also provided.

These and other features are presented below with reference to the associated drawings.

DETAILED DESCRIPTION

Figure 1:
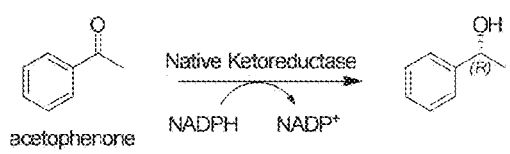
FIG. 1 illustrates geometric constraints for identifying active poses for a catalytic reaction of pro-R selectivity, the reaction involving a ketone reductase enzyme with a tyrosine moiety, an acetophenone substrate, and the cofactor NADPH.
Figure 1:
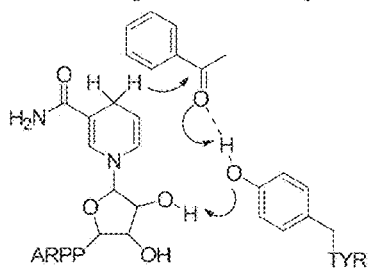
Figure 1:
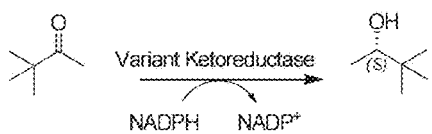
Figure 1:
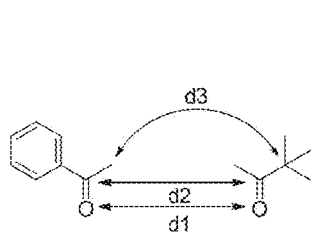
Figure 1:
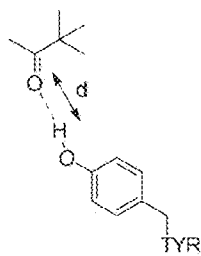
Figure 1:
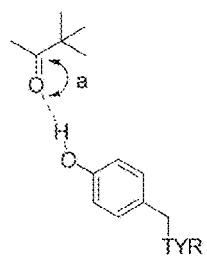
Figure 1:
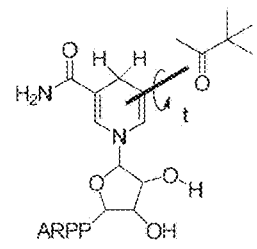

Screening of proteins and enzymes may be performed in actual ways that involve measurements of the chemical and physical properties of protein and enzyme molecules interacting with ligands and substrates. Actual measurements consume time and resources, and underlying physical and chemical mechanisms are often difficult to visualize or manipulate. The "virtual" screening methods and systems disclosed herein provide tools to visualize or manipulate the structure and dynamics of enzymes, proteins, and their substrates and ligands. These tools can save time and/or materials for studying the molecules.

In some embodiments, virtual screening of proteins or enzymes is used in directed evolution of proteins of interest. Virtual screening is used in place of physical screening during various stages of these directed evolution embodiments, making it possible to study a large number of molecules and reactions without requiring the physical materials or the time required by actual screening. These embodiments can speed up the processes for obtaining proteins and enzymes having desired properties. Materials and resources may also be saved in the processes. Some embodiments are especially useful for designing and developing enzymes having desired activity and/or selectivity for catalytic reactions involving particular substrates.

I. DEFINITIONS

Unless defined otherwise herein, all technical and scientific terms used herein have the same meaning as commonly understood by one of ordinary skill in the art. Various scientific dictionaries that include the terms included herein are well known and available to those in the art. Any methods and materials similar or equivalent to those described herein find use in the practice of the embodiments disclosed herein.

The terms defined immediately below are more fully understood by reference to the specification as a whole. The definitions are for the purpose of describing particular embodiments only and aiding in understanding the complex concepts described in this specification. They are not intended to limit the full scope of the disclosure. Specifically, it is to be understood that this disclosure is not limited to the particular sequences, compositions, algorithms, systems, methodology, protocols, and reagents described, as these may vary, depending upon the context they are used by those of skill in the art.

As used in this specification and appended claims, the singular forms "a", "an", and "the" include plural referents unless the content and context clearly dictates otherwise. Thus, for example, reference to "a device" includes a combination of two or more such devices, and the like. Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected).

"Docking" as used herein, refers to the computational process for simulating and/or characterizing the binding of a computational representation of a molecule (e.g., a substrate or ligand) to a computational representation of an active site of a biomolecule (e.g., an enzyme or protein). Docking is typically implemented in a computer system using a "docker" computer program. Typically, the result of a docking process is a computational representation of the molecule "docked" in the active site in a specific "pose." A plurality of docking processes may be carried out between the same computational representation of a molecule and the same computational representation of an active site resulting in a plurality of different "poses" of the molecule in the active site. The evaluation of the structure, conformation, and energetics of the plurality of different "poses" in the computational representation of the active site can identify certain "poses" as more energetically favorable for binding between the ligand and the biomolecule.

In some embodiments, poses generated from docking are evaluated to determine if they are "active" for a desired interaction with the biomolecule. "Active poses" are those meeting one or more constraints for an activity under consideration. A "constraint" may limit a pose's structure, geometry, conformation, energetics, etc. In certain embodiments, an "active pose" of a computational representation of a substrate in the active site of an enzyme satisfies conditions for catalysis by the enzyme. When docking identifies numerous active poses of a computational representation of a substrate in the computational representation of the active site, the specific enzyme represented may be selected as favorable for catalyzing the chemical transformation of the substrate to product.

A "docker" is a computer program that computationally simulates and/or characterizes the docking process between a computational representation of a molecule (e.g., a substrate or ligand) and a computation representation of an active site of interest in a protein or other biological molecule.

Dockers are typically implemented as software that may be temporarily or permanently stored in association with hardware such as a processor or processors. Commercially available docking programs include CDocker (Accelrys), DOCK (University of California, San Francisco), AutoDock (Scripps Research Institute), FlexX (tripos.com), GOLD (ccdc.cam.ac.uk), and GLIDE (schrodinger.com).

Docking using a docker typically generates "poses" of computational representations of substrates and ligands with respect to active sites. These poses may be used in generating a docking score or otherwise assessing docking. In some embodiments, poses are associated with interaction energy values calculated by a docker. Some poses are energetically more favorable than other poses. In some embodiments, the docker permits a user to specify a number of poses (n) to use in assessing docking. Only the top n poses with the best docking scores are considered in assessing docking. In some embodiments, only poses with favorable interaction energy that meet defined criteria are selected to be classified as active or inactive poses.

In some embodiments, a docker can determine that a substrate or ligand is likely to bind with a biomolecule if one or more poses of the substrate or ligand have favorable interaction energy with the biomolecule. A bound ligand may act as an agonist or antagonist. Various dockers output a docking score or other measure of binding between the substrate or ligand and the biomolecule. For some combinations of biomolecule active site with a substrate or ligand, the docking program will determine that binding is unlikely to occur. In such cases, the docking program will output a conclusion that the substrate or ligand does not bind with biomolecule.

A docker may be programmed to output an assessment of the likelihood that a ligand will dock with the active site of biomolecule or the quality of such docking, should it occur. The likelihood and quality of docking indicate the likelihood that a ligand will bind with a biomolecule. At one level, a docker determines whether a ligand is likely to bind to a biomolecule's active site. If the docker logic concludes that binding is not likely or is highly unfavorable, it may output a "no refined poses found" result. This may occur when all the conformations the docking program generated have unfavorable van der Waals clashes and/or electrostatic repulsions with the active site. In the above example of a docking procedure, if the second operation fails to find a pose with soft energy less than the threshold, the docker may return a result such as "no refined poses found." Because soft energy primarily considers nonbonded interactions including van der Waals and electrostatic forces, the "no refined poses found" result means the ligand has severe steric clashes and/or electrostatic repulsions with the biomolecule receptor for a given number of poses.

In certain embodiments, the docker outputs a docking score that represents the interaction between the ligand in the biomolecule active site. Dockers may calculate various features of the ligand-biomolecule interaction. In one example, the output is simply the interaction energy between the ligand and the biomolecule. In another embodiment, a total energy is output. The total energy may be understood to be a combination of ligand-biomolecule interaction energy and ligand strain. In certain implementations, such energy may be calculated using a force field such as CHARMm.

In various embodiments, docking programs generate such outputs by considering multiple poses of the ligand in the active site of the biomolecule. Each pose will have its own associated energy values. In some embodiments, the docking program ranks the poses and considers the energy associated with one or more of the high-ranking poses. In some cases, it may average the energies of certain high-ranking poses or otherwise perform a statistical analysis of the top ranking poses. In other embodiments, it simply chooses the value assisted with the top-ranked pose and outputs this as the resulting energy for the docking.

In some embodiments, the computational representation of a substrate corresponds to a molecular species along the reaction coordinate of an enzymatic reaction that is capable of converting the substrate molecule to the desired product molecule. In some embodiments, the computational representation of the substrate represents the substrate molecule per se. In some embodiments, the computational representation of the substrate represents an intermediate structure of the substrate that forms along the reaction coordinate (i.e., a "reaction intermediate of the substrate"). In some embodiments, the computational representation of the substrate represents a transition state structure that forms along the enzymatic reaction coordinate (i.e., a "transition state of the substrate").

In some embodiments, a computational representation of a ligand can represent a molecular species that binds strongly to an enzyme or biomolecule but does not proceed along a reaction coordinate to a desired product. For example, the computational representation of the ligand can represent a strong inhibitor in order to screen for inhibitors of an enzyme, or strong-binding antagonists or agonists of proteins (e.g., receptors).

A "pose" is the position or orientation of a substrate or ligand with respect to an active site of a biological molecule. In a pose, the three dimensional positions of some or all atoms of the ligand are specified with respect to some or all positions of atoms in the active site. While a ligand's conformation is not its pose—because the conformation does not consider the active site—the conformation can be used in determining a pose. In some embodiments, a ligand's orientation and conformation together define a pose. In some embodiments, a pose only exists if a ligand's orientation/conformation combination meets a defined threshold energy level in the reference active site.

Various computational mechanisms can be employed to generate poses for docking. Examples include systematic or stochastic torsional searches about rotatable bonds, molecular dynamics simulations, and genetic algorithms to "evolve" new low energy conformations. These techniques are used to modify computational representations of the ligand and/or active site to explore "pose space."

Dockers evaluate poses to determine how the ligand interacts with the active site. In some embodiments, they do this by calculating energy of interaction based on one or more of the interaction types mentioned above (e.g., van der Waals forces). This information is used to characterize docking and in some cases produce a docking score. In some implementations, dockers rank poses based on docking scores. In some implementations, dockers remove poses with unfavorable docking scores from consideration.

In certain embodiments, a virtual protein screening system evaluates a pose to determine whether the pose is active. A pose is deemed to be active if it meets defined constraints known to be important for the desired activity under consideration. As an example, the virtual protein screening system may determine whether a pose supports catalytic transformation of the ligand in an active site.

A "ligand" is a molecule or complex that interacts with an active site of a biomolecule to form a stable complex containing at least the ligand and biomolecule. In addition to the ligand and biomolecule, the stable complex may include (sometimes require) other chemical entities such as organic and inorganic cofactors (e.g., coenzymes and prosthetic groups), metal ions, and the like. Ligands may be agonists or antagonists.

The "active site" of a biomolecule is a site defined by the structure of the biomolecule which is capable of containing and/or binding all or part of a molecule (e.g., a substrate or ligand). Many types of active sites are contemplated and some of these are described elsewhere herein. Often the active site contains chemical and/or physical features (e.g., amino acid residues) capable of forming binding interactions with the substrate or ligand. In some embodiments (e.g., when the biomolecule is an enzyme), the "active site" includes at least one catalytic residue and a plurality of binding residues, and sometimes other chemical entities such as organic and inorganic cofactors (e.g., coenzymes and prosthetic groups), metal ions, and the like. The at least one catalytic residue of the active site may contain a catalytic moiety that catalyzes the turnover of a substrate. The binding residues of the active site provide binding interactions with the substrate to hold it in the active site in a stereoselective and/or regioselective manner. Such interactions may include van der Waals interactions, electrostatic interactions, hydrogen bonding, hydrophilic interactions, hydrophobic interactions, solvent interactions, covalent bonding, etc.

In some embodiments, a computational representation of an active site can be used for docking a computational representation of a substrate or ligand, thereby generating poses that can be evaluated for favorable interaction with the active site (e.g., determination of binding energy for poses).

In some embodiments, the computational representation of the active site is defined geometrically by a sphere or other shape. In some embodiments, the active site is defined by creating a sphere around the centroid of selected objects (e.g., ligands and/or other chemical entities in the structure template) with the radius adjusted to include them. The minimum radius is 5 Å but the active site size can be expanded by increasing the sphere radius by 1 Å, 2 Å, 3 Å, 4 Å, 6 Å, 8 Å, 10 Å, and so on. In some implementations, the size of the radius is selected to capture residues proximate the substrate. Therefore, larger substrates will be associated with larger radii and small substrates will be associated with smaller radii. It is not intended that the present disclosure be limited to any particular values of radii. In some embodiments, the active site can be defined from receptor cavities, where the active site was derived from one of the cavities detected in the structure template. In some embodiments, the active site can be defined from Protein Data Bank (PDB) site records, as the PDB file of the structure template often has active site defined using site records. Since all the homology models will be created using the structure template, the defined active site is transferable to all the homology models.

In some embodiments, the computational representation of the active site can be defined by various three-dimensional shapes, such as a user customizable shape (e.g., an ellipse or an irregular shape reflecting the structure of the substrate) with reference to moieties on the substrate and/or the enzyme.

In some embodiments, the computational representation of the active site can be defined to include amino acids that do not interact directly (e.g., via van der Waals interactions, electrostatic interactions, hydrogen bonding) with the substrate or ligand molecule in the active site, but which interact with other amino acids in the computational representation of the active site, and thereby affect the evaluation of poses of the substrate or ligand.

In some embodiments, residues contributing to catalysis and/or binding may exist outside of the computational representation of the active site as defined above. Such residues may be modified during directed evolution by considering residues beyond the active site as candidates for mutation or recombination.

A "reaction intermediate" is a chemical entity generated from the substrate in the transformation from substrate to reaction product. A "transition state" of a substrate is the substrate in a state corresponding to the highest potential energy along a reaction pathway. At a transition state that tends to have a fleeting existence, colliding reactant molecules proceed to form products. In this disclosure, sometimes when a substrate is described in a process, the intermediate and transition state may also be suitable for the process. In such situations, the substrate, intermediate, and transition state may collectively be referred to as "ligands." In some cases, multiple intermediates are generated in the catalytic transformation of a substrate. In certain embodiments, the ligand species (substrate or intermediate or transition state) chosen for analysis is one known to be associated with a rate limiting step in the catalytic transformation. As an example, a substrate covalently bound to an enzyme cofactor may be chemically modified in a rate limiting step. In such case, the substrate-cofactor species is used in modeling the interaction.

A "ligand" is a molecule capable of binding to a biomolecule and can include "substrate" molecules that are capable of binding and further undergoing a catalytic chemical transformation. Some ligands bind with an active site but do not undergo a catalytic transformation. Examples include ligands evaluated in the drug design field. Such ligands may be small molecules chosen for their ability to non-covalently bind with a target biomolecule for pharmacological purposes. In some cases, a ligand is evaluated for its ability to potentiate, activate, or inhibit the natural behavior of a biomolecule.

A "biomolecule" or "biological molecule" refers to a molecule that is generally found in or produced by a biological organism. In some embodiments, biological molecules comprise polymeric biological macromolecules having multiple subunits (i.e., "biopolymers"). Typical biomolecules include proteins, enzymes, and other polypeptides, DNA, RNA and other polynucleotides, and can also include molecules that share some structural features with naturally occurring polymers such as RNAs (formed from nucleotide subunits), DNAs (formed from nucleotide subunits), and peptides or polypeptides (formed from amino acid subunits), including, e.g., RNA analogues, DNA analogues, polypeptide analogues, peptide nucleic acids (PNAs), combinations of RNA and DNA (e.g., chimeraplasts), or the like. It is not intended that biomolecules be limited to any particular molecule, as any suitable biological molecule finds use in the present disclosure, including but not limited to, e.g., lipids, carbohydrates, or other organic molecules that are made by one or more genetically encodable molecules (e.g., one or more enzymes or enzyme pathways) or the like. Of particular interest for some aspects of this disclosure are biomolecules having active sites that interact with a ligand to effect a chemical or biological transformation, e.g., catalysis of a substrate, activation of biomolecules, or inactivation of the biomolecules, specifically enzymes.

In some embodiments, a "beneficial property" or "activity" is an increase or decrease in one or more of the following: catalytic rate ($k_{cat}$), substrate binding affinity ($K_M$), catalytic efficiency ($k_{cat}/K_M$), substrate specificity, chemoselectivity, regioselectivity, stereoselectivity, stereospecificity, ligand specificity, receptor agonism, receptor antagonism, conversion of a cofactor, oxygen stability, protein expression level, solubility, thermoactivity, thermostability, pH activity, pH stability (e.g., at alkaline or acidic pH), glucose inhibition, and/or resistance to inhibitors (e.g., acetic acid, lectins, tannic acids, and phenolic compounds) and proteases. Other desired activities may include an altered profile in response to a particular stimulus (e.g., altered temperature and/or pH profiles). In the context of rational ligand design, optimization of targeted covalent inhibition (TCI) is a type of activity. In some embodiments, two or more variants screened as described herein act on the same substrate but differ with respect to one or more of the following activities: rate of product formation, percent conversion of a substrate to a product, selectivity, and/or percent conversion of a cofactor. It is not intended that the present disclosure be limited to any particular beneficial property and/or desired activity.

In some embodiments, "activity" is used to describe the more limited concept of an enzyme's ability to catalyze the turnover of a substrate to a product. A related enzyme characteristic is its "selectivity" for a particular product such as an enantiomer or regioselective product. The broad definition of "activity" presented herein includes selectivity, although conventionally selectivity is sometimes viewed as distinct from enzyme activity.

The terms "protein," "polypeptide" and "peptide" are used interchangeably to denote a polymer of at least two amino acids covalently linked by an amide bond, regardless of length or post-translational modification (e.g., glycosylation, phosphorylation, lipidation, myristilation, ubiquitination, etc.). In some cases, the polymer has at least about 30 amino acid residues, and usually at least about 50 amino acid residues. More typically, they contain at least about 100 amino acid residues. The terms include compositions conventionally considered to be fragments of full-length proteins or peptides. Included within this definition are D- and L-amino acids, and mixtures of D- and L-amino acids. The polypeptides described herein are not restricted to the genetically encoded amino acids. Indeed, in addition to genetically encoded amino acids, the polypeptides described herein may be made up of, either in whole or in part, naturally-occurring and/or synthetic non-encoded amino acids. In some embodiments, a polypeptide is a portion of the full-length ancestral or parental polypeptide, containing amino acid additions or deletions (e.g., gaps) and/or substitutions, as compared to the amino acid sequence of the full-length parental polypeptide, while still retaining functional activity (e.g., catalytic activity).

A "wild type" or "wildtype" (WT) biomolecule or organism is one that has the phenotype of the typical form of a species as it occurs in nature. Sometimes a wild type biomolecule has been isolated from a naturally occurring source. Other times, it is derived in the laboratory environment. Usually, wild type biomolecules are related to or encoded by genetic sequences of normal or reference genomes as opposed to mutant genomes. Included within the definition of "wild type biomolecules" are recombinant forms of a polypeptide or polynucleotide having a sequence identical to the native form. A substrate or ligand that reacts with a wild-type biomolecule is sometimes considered a "native" substrate or ligand.

As used herein, the terms "variant," "mutant," "mutant sequence," and "variant sequence" refer to a biological sequence that differs in some respect from a standard or reference sequence (e.g., in some embodiments, a parental sequence). The difference may be referred to as a "mutation". In some embodiments, a mutant is a polypeptide or polynucleotide sequence that has been altered by at least one substitution, insertion, cross-over, deletion, and/or other genetic operation. For purposes of the present disclosure, mutants and variants are not limited to a particular method by which they are generated. In some embodiments, a mutant or variant sequence has increased, decreased, or substantially similar activities or properties, in comparison to the parental sequence. In some embodiments, the variant polypeptide comprises one or more amino acid residues that have been mutated, as compared to the amino acid sequence of the wild-type polypeptide (e.g., a parent polypeptide). In some embodiments, one or more amino acid residues of the polypeptide are held constant, are invariant, or are not mutated as compared to a parent polypeptide in the variant polypeptides making up a plurality of polypeptides. In some embodiments, the parent polypeptide is used as the basis for generating variants with improved stability, activity, or any other desired property.

As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for the desired property (e.g., high or increased; or low or reduced activity, increased thermal and/or alkaline stability, etc.).

A "panel of enzymes" is a group of enzymes selected such that each member of the panel catalyzes the same chemical reaction. In some embodiments, the members of the panel can collectively turn over multiple substrates, each undergoing the same reaction. Often the panel members are chosen to efficiently turn over multiple substrates. In some cases, the panels are commercially available. In other cases, they are proprietary to an entity. For example, a panel may include various enzymes identified as hits in a screening procedure. In certain embodiments, one or more members of a panel exist only as a computational representation. In other words, the enzyme is a virtual enzyme.

A "model" is a representation of the structure of a biomolecule or ligand. It is sometimes provided as a collection of three-dimensional positions for the atoms or moieties of the entity being represented. Models often contain computationally-produced representations of the active sites or other aspects of the enzyme variants. Examples of models relevant to the embodiments herein are produced from homology modeling, protein threading, or ab initio protein modeling using a routine such as Rosetta (rosettacommons.org/software/) or Molecular Dynamics simulations.

A "homology model" is a three dimensional model of a protein or portion of a protein containing at least the active site of a ligand under consideration. Homology modeling relies on the observation that protein structures tend to be conserved amongst homologous proteins. A homology model provides three dimensional positions of residues including backbone and side chains. The model is generated from a structure template of a homologous protein likely to resemble the structure of the modeled sequence. In some embodiments, a structure template is used in two steps: "align sequence to templates" and "build homology models".

The "align sequence to templates" step aligns the model sequence to one or more structure template sequences and prepares an input sequence alignment for building the homology model. The alignment identifies gaps and other regions of dissimilarity between the model sequence and the structure template sequence(s).

The "building homology models" step uses structural features of the structure template to derive spatial restraints which, in turn, are used to generate, e.g., model protein structures using conjugate gradient and simulated annealing optimization procedures. The structural features of the template may be obtained from a technique such as NMR or x-ray crystallography. Examples of such techniques can be found in the review article, "A Guide to Template Based Structure Prediction," by Qu X, Swanson R, Day R, Tsai J. Curr Protein Pept Sci. 2009 June; 10(3):270-85.

The term "active conformation" is used in reference to a conformation of a protein (e.g., an enzyme) that allows the protein to cause a substrate to undergo a chemical transformation (e.g., a catalytic reaction).

An "active pose" is one in which a ligand is likely to undergo a catalytic transformation or perform some desired role such as covalently binding with the binding site.

The terms "oxidoreduction," "oxidation-reduction," and "redox" are used interchangeably with reference to a reversible chemical reaction in which one reaction is an oxidation and the reverse is a reduction. The terms are also used to refer to all chemical reactions in which atoms have their oxidation state changed; in general, redox reactions involve the transfer of electrons between species. This can be either a simple redox process, such as the oxidation of carbon to yield carbon dioxide ($CO_2$) or the reduction of carbon by hydrogen to yield methane ($CH_4$), or a complex process such as the oxidation of glucose ($C_6H_{12}O_6$) in the human body through a series of complex electron transfer processes.

An "oxidoreductase" is an enzyme that catalyzes an oxidoreduction reaction.

The term "transferation" is used herein to refer to a chemical reaction that transfers a functional group from one compound to another compound. A "transferase" is used to refer to any of various enzymes that catalyze a transferation reaction.

The term "hydrolysis" is used to refer to a chemical reaction in which water reacts with a compound to produce other compounds, which reaction involves the splitting of a chemical bond by the addition of the hydrogen cation and the hydroxide anion from the water.

A "hydrolase" is an enzyme that catalyzes a hydrolysis reaction.

The term "isomerization" is used to refer to a chemical reaction that converts a compound into an isomer.

An "isomerase" is an enzyme that catalyzes an isomerization reaction, causing its substrate to change into an isomeric form.

The term "ligation" is used herein to refer to any chemical reactions that join two molecules by forming a new chemical bond. In some embodiments, a ligation reaction involves hydrolysis of a small chemical group dependent to one of the larger molecules. In some embodiments, an enzyme catalyzes the linking together of two compounds, e.g., enzymes that catalyze joining of C—O, C—S, C—N, etc. An enzyme that catalyzes a ligation reaction is referred to as a "ligase".

A "lyase" is an enzyme that catalyzes the breaking of various chemical bonds by means other than hydrolysis and oxidation. In some embodiments, a lyase reaction forms a new double bond or a new ring structure.

A "ketoreductase" is an enzyme that typically uses cofactor NADPH to stereospecifically reduce a keto group to a hydroxyl group (See e.g., variants disclosed in WO2008103248A2, WO2009029554A2, WO2009036404A2, WO2009042984A1, WO2009046153A1, and WO2010025238A2).

A "transaminase" or an "aminotransferase" is an enzyme that catalyzes a transamination reaction between an amino acid and an α-keto acid, in which the amine group $NH_2$ on the amino acid is exchanged with the keto group =O on the α-keto acid (See e.g., variants disclosed in WO2010081053A2 and WO2010099501A2).

The "cytochrome" proteins (abbreviated as "CYP") are enzymes involved in oxidation of organic substances. One example is cytochrome P450 enzymes. The substrates of CYP enzymes include, but are not limited to metabolic intermediates such as lipids and steroidal hormones, as well as xenobiotic substances such as drugs and other toxic chemicals. CYPs are the major enzymes involved in drug metabolism and bioactivation. CYPs use a variety of small and large molecules as substrates in enzymatic reactions. The most common reaction catalyzed by cytochrome P450 is a monooxygenase reaction, e.g., insertion of one atom of oxygen into an organic substrate (RH) while the other oxygen atom is reduced to water. Cytochrome P450 enzymes belong to a superfamily of proteins containing a heme cofactor and, therefore, are hemoproteins. In general, they are terminal oxidase enzymes in electron transfer chains. The MicroCyp® screening plates and enzymes available from Codexis are useful in production of drug metabolites and novel lead compounds (See e.g., variants disclosed in WO2002083868A2, WO2005017105A2, WO2005017116A2, and WO2003008563A2).

A "Baeyer-Villiger monooxygenase" is an enzyme that employs NADPH and molecular oxygen to catalyze a Baeyer-Villiger oxidation reaction, in which an oxygen atom is inserted into a carbon-carbon bond of a carbonylic substrate (See e.g., variants in WO2011071982A2 and WO2012078800A2).

A "monoamine oxidase" (MAO) (EC 1.4.3.4) is an enzyme that catalyze the oxidation of monoamines, which are neurotransmitters and neuromodulators that contain one amino group that is connected to an aromatic ring by a two-carbon chain (—$CH_2$—$CH_2$—). MAOs belong to the protein family of flavin-containing amine oxidoreductases (See e.g., variants in WO2010008828A2).

A "nitrilase" or nitrile aminohydrolase (EC 3.5.5.1) is an enzyme that catalyzes the hydrolysis of nitriles to carboxylic acids and ammonia, without the formation of "free" amide intermediates (See e.g., variants in WO2011011630A2).

An "imine reductase" is an enzyme that catalyzes the reduction of an imine functional group containing a carbon-nitrogen double bond, breaking the double bond by causing an electron to be donated to the nitrogen atom.

An "enone reductase" is an enzyme that catalyzes the reduction of an enone functional group, which includes a conjugated system of an alkene and a ketone, breaking the keto- or alkene double bond (See e.g., variants disclosed in WO2010075574A2).

An "acylase" is an enzyme that catalyzes the hydrolytic cleavage of acyl amide or acyl ester bonds (See e.g., variants of penicillin G acylase in WO2010054319A2).

A "halohydrin dehalogenase" "HHDH" is an enzyme involved in the degradation of vicinal halohydrins. In *Agrobacterium radiobacter* AD1, for instance, it catalyzes the dehalogenation of halohydrins to produce the corresponding epoxides (See e.g., variants disclosed in WO2010080635A2).

The term "sequence" is used herein to refer to the order and identity of any biological sequences including but not limited to a whole genome, whole chromosome, chromosome segment, collection of gene sequences for interacting genes, gene, nucleic acid sequence, protein, peptide, polypeptide, polysaccharide, etc. In some contexts, a "sequence" refers to the order and identity of amino acid residues in a protein (i.e., a protein sequence or protein character string) or to the order and identity of nucleotides in a nucleic acid (i.e., a nucleic acid sequence or nucleic acid character string). A sequence may be represented by a character string. A "nucleic acid sequence" refers to the order and identity of the nucleotides comprising a nucleic acid. A "protein sequence" refers to the order and identity of the amino acids comprising a protein or peptide.

"Codon" refers to a specific sequence of three consecutive nucleotides that is part of the genetic code and that specifies a particular amino acid in a protein or starts or stops protein synthesis.

The term "gene" is used broadly to refer to any segment of DNA or other nucleic acid associated with a biological function. Thus, genes include coding sequences and optionally, the regulatory sequences required for their expression. Genes also optionally include non-expressed nucleic acid segments that, for example, form recognition sequences for other proteins. Genes can be obtained from a variety of sources, including cloning from a source of interest or synthesizing from known or predicted sequence information, and may include sequences designed to have desired parameters.

A "moiety" is a part of a molecule that may include either whole functional groups or parts of functional groups as substructures, while functional groups are groups of atoms or bonds within molecules that are responsible for the characteristic chemical reactions of those molecules.

"Screening" refers to the process in which one or more properties of one or more bio-molecules are determined. For example, typical screening processes include those in which one or more properties of one or more members of one or more libraries are determined.

Screening can be performed computationally using computational models of biomolecules and virtual environment of the biomolecules. In some embodiments, virtual protein screening systems are provided for selected enzymes of desired activity and selectivity.

An "expression system" is a system for expressing a protein or peptide encoded by a gene or other nucleic acid.

"Directed evolution," "guided evolution," or "artificial evolution" refers to in silico, in vitro, or in vivo processes of artificially changing one or more biomolecule sequences (or a character string representing that sequence) by artificial selection, mutation, recombination, or other manipulation. In some embodiments, directed evolution occurs in a reproductive population in which (1) there are varieties of individuals, (2) some varieties having heritable genetic information, and (3) some varieties differ in fitness. Reproductive success is determined by outcome of selection for a predetermined property such as a beneficial property. The reproductive population can be, e.g., a physical population in an in vitro process or a virtual population in a computer system in an in silico process.

Directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237: 1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391: 288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In certain embodiments, directed evolution methods generate protein variant libraries by recombining genes encoding variants developed from a parent protein, as well as by recombining genes encoding variants in a parent protein variant library. The methods may employ oligonucleotides containing sequences or subsequences encoding at least one protein of a parental variant library. Some of the oligonucleotides of the parental variant library may be closely related, differing only in the choice of codons for alternate amino acids selected to be varied by recombination with other variants. The method may be performed for one or multiple cycles until desired results are achieved. If multiple cycles are used, each typically involves a screening step to identify those variants that have acceptable or improved performance and are candidates for use in at least one subsequent recombination cycle. In some embodiments, the screening step involves a virtual protein screening system for determining the catalytic activity and selectivity of enzymes for desired substrates.

In some embodiments, directed evolution methods generate protein variants by site-directed mutagenesis at defined residues. These defined residues are typically identified by structural analysis of binding sites, quantum chemistry analysis, sequence homology analysis, sequence-activity models, etc. Some embodiments employ saturation mutagenesis, in which one tries to generate all possible (or as close to as possible) mutations at a specific site, or narrow region of a gene.

"Shuffling" and "gene shuffling" are types of directed evolution methods that recombine a collection of fragments of the parental polynucleotides through a series of chain extension cycles. In certain embodiments, one or more of the chain extension cycles is self-priming; i.e., performed without the addition of primers other than the fragments themselves. Each cycle involves annealing single stranded fragments through hybridization, subsequent elongation of annealed fragments through chain extension, and denaturing. Over the course of shuffling, a growing nucleic acid strand is typically exposed to multiple different annealing partners in a process sometimes referred to as "template switching," which involves switching one nucleic acid domain from one nucleic acid with a second domain from a second nucleic acid (i.e., the first and second nucleic acids serve as templates in the shuffling procedure).

Template switching frequently produces chimeric sequences, which result from the introduction of crossovers between fragments of different origins. The crossovers are created through template switched recombinations during the multiple cycles of annealing, extension, and denaturing. Thus, shuffling typically leads to production of variant polynucleotide sequences. In some embodiments, the variant sequences comprise a "library" of variants (i.e., a group comprising multiple variants). In some embodiments of these libraries, the variants contain sequence segments from two or more parent polynucleotides.

When two or more parental polynucleotides are employed, the individual parental polynucleotides are sufficiently homologous that fragments from different parents hybridize under the annealing conditions employed in the shuffling cycles. In some embodiments, the shuffling permits recombination of parent polynucleotides having relatively limited/low homology levels. Often, the individual parent polynucleotides have distinct and/or unique domains and/or other sequence characteristics of interest. When using parent polynucleotides having distinct sequence characteristics, shuffling can produce highly diverse variant polynucleotides.

Various shuffling techniques are known in the art (See e.g., U.S. Pat. Nos. 6,917,882, 7,776,598, 8,029,988, 7,024, 312, and 7,795,030, all of which are incorporated herein by reference in their entireties).

Some directed evolution techniques employ "Gene Splicing by Overlap Extension" or "gene SOEing," which is a PCR-based method of recombining DNA sequences without reliance on restriction sites and of directly generating mutated DNA fragments in vitro. In some implementations of the technique, initial PCRs generate overlapping gene segments that are used as template DNA for a second PCR to create a full-length product. Internal PCR primers generate overlapping, complementary 3' ends on intermediate segments and introduce nucleotide substitutions, insertions or deletions for gene splicing. Overlapping strands of these intermediate segments hybridize at 3' region in the second PCR and are extended to generate the full-length product. In various applications, the full length product is amplified by flanking primers that can include restriction enzyme sites for inserting the product into an expression vector for cloning purposes (See e.g., Horton, et al., Biotechniques, 8(5): 528-35 [1990]). "Mutagenesis" is the process of introducing a mutation into a standard or reference sequence such as a parent nucleic acid or parent polypeptide.

Site-directed mutagenesis is one example of a useful technique for introducing mutations, although any suitable method finds use. Thus, alternatively or in addition, the mutants may be provided by gene synthesis, saturating random mutagenesis, semi-synthetic combinatorial libraries of residues, recursive sequence recombination ("RSR") (See e.g., US Patent Application Publ. No. 2006/0223143, incorporated by reference herein in its entirety), gene shuffling, error-prone PCR, and/or any other suitable method.

One example of a suitable saturation mutagenesis procedure is described in US Patent Application Publ. No. 2010/0093560, which is incorporated herein by reference in its entirety.

A "fragment" is any portion of a sequence of nucleotides or amino acids. Fragments may be produced using any suitable method known in the art, including but not limited to cleaving a polypeptide or polynucleotide sequence. In some embodiments, fragments are produced by using nucleases that cleave polynucleotides. In some additional embodiments, fragments are generated using chemical and/or biological synthesis techniques. In some embodiments, fragments comprise subsequences of at least one parental sequence, generated using partial chain elongation of complementary nucleic acid(s). In some embodiments involving in silico techniques, virtual fragments are generated computationally to mimic the results of fragments generated by chemical and/or biological techniques. In some embodiments, polypeptide fragments exhibit the activity of the full-length polypeptide, while in some other embodiments, the polypeptide fragments do not have the activity exhibited by the full-length polypeptide.

"Parental polypeptide," "parental polynucleotide," "parent nucleic acid," and "parent" are generally used to refer to the wild-type polypeptide, wild-type polynucleotide, or a variant used as a starting point in a diversity generation procedure such as a directed evolution. In some embodiments, the parent itself is produced via shuffling or other diversity generation procedure(s). In some embodiments, mutants used in directed evolution are directly related to a parent polypeptide. In some embodiments, the parent polypeptide is stable when exposed to extremes of temperature, pH and/or solvent conditions and can serve as the basis for generating variants for shuffling. In some embodiments, the parental polypeptide is not stable to extremes of temperature, pH and/or solvent conditions, and the parental polypeptide is evolved to make a robust variants.

A "parent nucleic acid" encodes a parental polypeptide.

A "library" or "population" refers to a collection of at least two different molecules, character strings, and/or models, such as nucleic acid sequences (e.g., genes, oligonucleotides, etc.) or expression products (e.g., enzymes or other proteins) therefrom. A library or population generally includes a number of different molecules. For example, a library or population typically includes at least about 10 different molecules. Large libraries typically include at least about 100 different molecules, more typically at least about 1000 different molecules. For some applications, the library includes at least about 10000 or more different molecules. However, it is not intended that the present invention be limited to a specific number of different molecules. In certain embodiments, the library contains a number of variant or chimeric nucleic acids or proteins produced by a directed evolution procedure.

Two nucleic acids are "recombined" when sequences from each of the two nucleic acids are combined to produce progeny nucleic acid(s). Two sequences are "directly" recombined when both of the nucleic acids are substrates for recombination.

"Selection" refers to the process in which one or more bio-molecules are identified as having one or more properties of interest. Thus, for example, one can screen a library to determine one or more properties of one or more library members. If one or more of the library members is/are identified as possessing a property of interest, it is selected. Selection can include the isolation of a library member, but this is not necessary. Further, selection and screening can be, and often are, simultaneous. Some embodiments disclosed herein provide systems and methods for screening and selecting enzymes of desirable activity and/or selectivity.

The term "sequence-activity model" refers to any mathematical models that describe the relationship between activities, characteristics, or properties of biological molecules on the one hand, and various biological sequences on the other hand.

"Reference sequence" is a sequence from which variation of sequence is effected. In some cases, a "reference sequence" is used to define the variations. Such sequence may be one predicted by a model to have the highest value (or one of the highest values) of the desired activity. In another case, the reference sequence may be that of a member of an original protein variant library. It certain embodiments, a reference sequence is the sequence of a parent protein or nucleic acid.

"Next-generation sequencing" and "high-throughput sequencing" are sequencing techniques that parallelize the sequencing process, producing thousands or millions of sequences at once. Examples of suitable next-generation sequencing methods include, but are not limited to, single molecule real-time sequencing (e.g., Pacific Biosciences, Menlo Park, Calif.), ion semiconductor sequencing (e.g., Ion Torrent, South San Francisco, Calif.), pyrosequencing (e.g., 454, Branford, Conn.), sequencing by ligation (e.g., SOLiD sequencing of Life Technologies, Carlsbad, Calif.), sequencing by synthesis and reversible terminator (e.g., Illumina, San Diego, Calif.), nucleic acid imaging technologies such as transmission electron microscopy, and the like.

A "genetic algorithm" is a process that mimics evolutionary processes. Genetic algorithms (GAs) are used in a wide variety of fields to solve problems which are not fully characterized or too complex to allow full characterization, but for which some analytical evaluation is available. That is, GAs are used to solve problems that can be evaluated by some quantifiable measure for the relative value of a solution (or at least the relative value of one potential solution in comparison to another). In the context of the present disclosure, a genetic algorithm is a process for selecting or manipulating character strings in a computer, typically where the character string corresponds to one or more biological molecules (e.g., nucleic acids, proteins, or the like) or data used to train a model such as a sequence activity model.

In a typical implementation, a genetic algorithm provides and evaluates a population of character strings in a first generation. A "fitness function" evaluates the members of the population and ranks them based on one or more criteria such as high activity. High ranking character strings are selected for promotion to a second generation and/or mating to produce "children character strings" for the second generation. The population in the second generation is similarly evaluated by the fitness function, and high ranking members are promoted and/or mated as with the first generation. The genetic algorithm continues in this manner for subsequent generations until a "convergence criterion" is met, at which point the algorithm concludes with one or more high ranking individuals.

The term "genetic operation" (or "GO") refer to biological and/or computational genetic operations, wherein all changes in any population of any type of character strings (and thus in any physical properties of physical objects encoded by such strings) can be described as a result of random and/or predetermined application of a finite set of logical algebraic functions. Examples of GO include but are not limited to multiplication, crossover, recombination, mutation, ligation, fragmentation, etc.

II. VIRTUAL PROTEIN SCREENING

In some embodiments, a virtual protein screening system is configured to perform various operations associated with computationally identifying biomolecule variants that are likely to have a desirable activity such as efficiently and selectively catalyzing a reaction at a defined temperature. The virtual protein screening system may take as inputs, representations of one or more than one ligands that are intended to interact with the variants. The system may take as other inputs, representations of the biomolecule variants, or at least the active sites of these variants. The representations may contain three-dimensional positions of atoms and/or moieties of the ligands and/or variants. Homology models are examples of the representations of the biomolecule variants. The virtual protein screening system may apply docking information and activity constraints to assess the functioning of the variants.

In certain embodiments, a virtual protein screening system applies one or more constraints to distinguish active and inactive poses. Such poses may be generated by a docker as described above or by another tool. A ligand pose is evaluated in its environment to determine whether one or more features of the ligand are positioned in the environment so as to result in a catalytic transformation or other defined activity. The environment in question is typically an active site of an enzyme or other biomolecule.

If one assumes that a substrate or other ligand binds to an active site of the biomolecule, the question to be asked whether it binds in an "active" way. A typical docking program can tell one whether or not a ligand will bind to the active site, but does not tell one whether it binds in an "active" way.

In certain embodiments, activity is determined by considering one or more poses generated by a docker or other tool. Each pose is evaluated to determine whether it meets constraints associated with an activity of interest (e.g., a "desired activity"). An active pose is one in which the ligand is likely to undergo a catalytic transformation or perform some desired role such as covalently binding with the binding site.

When considering catalytic turnover of a substrate as the activity, the virtual protein screening system may be configured to identify poses known to be associated with a particular reaction. In some embodiments, this involves considering a reaction intermediate or transition state rather than the substrate itself. In addition to turnover, poses may be evaluated for other types of activity such as stereoselective synthesis of enantiomers, binding to a receptor of a target biomolecule identified as important for drug discovery, regioselective conversion of products, etc. In some cases, the activity is irreversible or reversible covalent binding such as targeted covalent inhibition (TCI).

Constraints may be determined directly, manually, automatically, empirically, and/or based on previously known information. In one approach, a researcher evaluates the active site and a native substrate for a wild-type protein. This is because wild-type protein is known to be evolved for its native substrate by nature and hence has optimal catalytic constant ($k_{cat}$). In some cases, crystal structures of the wild-type protein and native substrate or an intermediate complex have been solved. The constraint can then be set up based on structural analysis. This is referred to as a "direct approach" for determining the constraint. In cases where such crystal structures are not available, the evaluation may be conducted with a docking program for example. Using the program, the researcher identifies constraints associated with a catalytic transformation of the native substrate in the wild-type protein. This is referred to as a manual or empirical approach for determining constraints. In another approach, constraints are determined using quantum mechanics calculations. For example, a researcher can optimize the substrate or intermediate or transition state in the presence of functional groups of the catalytic residues (e.g., Tyr) and/or cofactors (e.g., NADHP), using quantum mechanics and set the constraint to resemble those states. This approach is sometimes referred to as an automatic or ab initio approach. An example of a commercial tool using this approach is Gaussian available from wwwl.lGaussian.com.

Constraints may take various forms. In certain embodiments, some or all these constraints are geometric constraints that specify the relative position(s) of one more atoms in a ligand pose in a three-dimensional space. In some embodiments, the space may be defined with respect to the positions of atoms in an active site.

A "geometric constraint" is a constraint that evaluates the geometry of two or more participant moieties or other chemical elements. In certain embodiments, one of the participants is a moiety or other chemical species on the ligand. In some embodiments, another of the participants is a moiety or other chemical feature of an active site of a biomolecule. The moiety or other chemical feature of the active site may be associated with residues on the biomolecule active site (e.g., an amino acid residue side-chain), a feature on a cofactor or other compound that is typically associated with the active site and/or catalysis, and the like. As an example, in the reduction of ketones by a ketoreductase protein, the carbonyl group of the substrate may be one participant in a geometric constraint and a tyrosine moiety of an enzyme active site may be a second participant in the geometric constraint.

In general, geometric constraints are made with respect to a ligand on the one hand and one or more features of the binding environment on the other hand. In some embodiments, the environment may include residue positions of the peptide backbone (or side-chains) and/or cofactors or other non-backbone materials that normally reside in an active site.

The geometry of the participants in the geometric constraint may be defined in terms of distance between moieties, angles between moieties, torsional relation between moieties, etc. Sometimes, a constraint includes multiple basic geometric constraints used to characterize activity. For example, a constraint on the position of a substrate may be defined by distances between two or more pairs of atoms. An example is shown in FIG. 1. In the case of a torsional relation, the constraint may be appropriate when a substrate and a feature of the active site environment are viewed as nominally parallel plates sharing a common axis of rotation. The relative angular position of these plates around the axis defines the torsional constraint.

FIG. 1 depicts an example of a workflow that may be employed to identify geometric constraints for identifying active poses. The depicted workflow assumes that the wild type enzyme is a ketone reductase and the native substrate is acetophenone. As depicted in the top left corner of FIG. 1, the native reaction converts acetophenone to a corresponding alcohol by stereoselective catalysis. The reaction introduces a chiral center at the acetyl carbon of the ketone substrate. The wild-type ketone reductase controls the conversion so that only the R enantiomer is produced. The reaction is accomplished in the presence of NADPH as a cofactor. The reaction is depicted schematically in the top left corner of FIG. 1.

In the top right corner of FIG. 1, the mechanism of catalysis and selectivity is depicted. This mechanism is considered when defining geometric constraints used to distinguish active from inactive poses. As part of the process, a researcher or automated system determines the orientation of the acetophenone substrate with respect to its catalytic environment in the wild-type ketone reductase. In general, the relevant environment includes the surrounding residues, cofactors, etc. present when the catalytic transformation takes place.

In the depicted example, the relevant features of the active site environment in the wild-type ketone reductase are the positions of atoms in (1) a tyrosine residue in the backbone of the wild-type enzyme and (2) the cofactor, NADPH. Other relevant environmental features of the substrate in the active poses are sub-pockets within the active site. These are not shown in FIG. 1. One of the sub-pockets accommodates the phenyl group of the acetophenone substrate and another accommodates the methyl group of the acetophenone. Together these sub-pockets hold the substrate in an orientation that dictates the stereospecificity of the reaction. In some embodiments, the above information is gathered based on structural analysis of the crystal structure of the wild-type ketone reductase and native acetophenone substrate complex. Hence, the geometric constraints can be directly defined.

The catalytic mechanism of ketoreductase is depicted by a sequence of arrows shown in the depicted arrangement (top right corner of FIG. 1). Specifically, the NADPH donates electrons through a hydride ion that couples with the carbonyl carbon of the acetophenone. Concurrently, an electron pair from the carbonyl oxygen of the acetophenone is donated to the proton of the tyrosine residue, and an electron pair from the hydroxyl oxygen of the tyrosine is donated to the proton of the ribose moiety of NADP(H), hence completing the substrate's conversion to the corresponding alcohol. As noted, the reaction proceeds while the substrate's phenyl group is held in one larger sub-pocket, its methyl group is held in a smaller sub sub-pocket, and its ketone group is held in close proximity toward the tyrosine hydroxyl group.

As further shown in FIG. 1, the wild-type ketone reductase is evolved to a variant ketone reductase that stereospecifically catalyzes the conversion of a different substrate, called a "desired substrate," herein. As depicted in a middle of FIG. 1, the desired reaction is a conversion of methyl tert-butyl ketone to the S enantiomer of the corresponding alcohol (1 tert-butyl ethyl alcohol). The reaction is presumed to be catalyzed in an active site of a variant enzyme optimized for the conversion and with the cofactor NADPH.

To ensure that the reaction unfolds with the desired stereospecificity, one or more constraints should be determined. Note that the native substrate is converted by the wild-type ketone reductase to the R enantiomer and the desired substrate is to be converted by the variant to the S enantiomer. Therefore, one may consider that the tert-butyl group of the desired substrate should be positioned in the sub-pocket that normally accommodates the methyl group of the native acetophenone substrate and the methyl group of the desired substrate should be positioned in the sub-pocket that accommodates the phenyl group of the native substrate.

With this in mind, a set of positional constraints may be defined as depicted in the lower left corner of FIG. 1. As shown therein, various constraints are defined with respect to the three-dimensional position of the native substrate as it sits in the WT enzyme active site in the crystal structure, in order to obtain maximum turnover ($k_{cat}$). In other words, the orientation of the key functional group of the native substrate, including carbonyl carbon and carbonyl oxygen that dictate catalytic turnover and either of the two carbons next to the carbonyl carbon that dictate stereoselectivity, as determined with respect to the diagram in the top right corner of FIG. 1 is translated into X, Y, Z coordinates. Since homology models of all the variants were built using WT structure as template, the X, Y, Z coordinates are transferable to the variants. With this frame of reference, the positions of the key functional group ($C_1(C_2)C=O$) of the desired substrate can be compared to the positions of the corresponding 4 atoms of the native substrate as they are predicted to sit in an optimal orientation toward the catalytic tyrosine residue and NADPH cofactor. It is noteworthy that the residues for catalysis (e.g., tyrosine) and residues for cofactor (NADPH) binding are conserved in all the variants and only subtle conformational or positional changes are expected for this tyrosine and NADPH in all the variants. With this in mind, the positional constraints depicted in the bottom left corner of FIG. 1 specify a range of positions of the desired substrate's carbonyl carbon atom, carbonyl oxygen atom, and central tert-butyl atom with respect to corresponding positions of the native substrate's carbonyl carbon atom, carbonyl oxygen atom, and methyl carbon atom. The range of positional differences between the desired substrate's atoms and the native substrate's corresponding atoms is depicted by the distances d1, d2, and d3. As an example, each of these distances may be required to be 1 angstrom or more or less in order for a pose of the desired substrate to be deemed an active pose. The constraint values are usually set to be a range that allows certain flexibility reflecting subtle conformational changes of the catalytic tyrosine and cofactor in a variant. In some implementations, the criteria for these distances are refined by machine learning algorithms.

In the examples above, the positions of the three relevant atoms of the desired substrate approximate those of the native substrate. The ketoreductase variants docked with the desired substrate in poses satisfying the above positional constraints are expected to be catalytically active and S selective.

In general, the virtual protein screening system may apply geometric constraints of any of various types. In some implementations, it applies the absolute distance between participants. For example, the distance between an oxygen atom in the carbonyl group of a substrate and an atom of a tyrosine group of an active site may be specified as a constraint (e.g., the distance between these atoms must be 2 Å±0.5 Å). In another example, the angle between one line defined by the axis between the carbon and oxygen atoms in a carbonyl group and another line along an axis of a phenyl group in an active site is 120°±20°.

The bottom right of FIG. 1 depicts examples of types of geometric constraints, each defined between one or more atoms of the desired substrate and one or more atoms of the enzyme or a cofactor (or other entity) within a binding pocket. A distance constraint is defined as the distance between an atom on the substrate and an atom on an active site residue, a cofactor, etc. In angle constraint is defined for a pose by the angular relation between two or more axes defined on the substrate and its environment. The axes may be covalent bonds, lines between atoms of the substrate and a moiety in the binding pocket, etc. For example, an angle may be defined between one axis defined between two atoms on the substrate and another axis defined as the separation between an atom on a residue and an atom on the substrate. In some other embodiments, one axis is defined between two atoms on a residue side chain and another axis is defined by separation between an atom on the substrate and an atom on the residue. An additional type of geometric constraint is depicted in the bottom right corner of FIG. 1. This type of constraint is referred to as a "torsional constraint" and assumes that two distinct entities in the binding pocket (one of them typically being all or part of the substrate) share a common axis of rotation. The torsional constraint may be defined by a range of angular positions of one of the entities with respect to the other around the common axis of rotation.

In general, the geometric constraint may be applied with respect to some preset geometric position or orientation of a substrate moiety within a binding pocket. Such position or orientation may be specified by, for example, a representative position of an active moiety in a native substrate in a binding pocket. As an example, the carbon and oxygen atoms of the carbonyl group of the substrate under consideration must be within 1 Å of the locations of the carbon oxygen atoms of a carbonyl group in a native substrate in the binding pocket. See the positional constraint shown in the lower left corner of FIG. 1. Note that the positional constraints in the lower left corner of FIG. 1 exist between the desired substrate and the native substrate. However, the positional constraints can be translated into relations between the desired substrate and enzyme variants, which correspond to the geometric constraints in the lower middle and right corner of FIG. 1.

In addition to determining the geometric constraints directly, manually, or automatically using computer systems, the constraints can also be refined by screening results. For example, if one or more than one variants are identified as being active while some others are identified as being inactive for the desired reaction through laboratory screening, their poses can be further analyzed and the constraints can be trained.

While the example depicted in FIG. 1 uses a relatively small and simple molecule (methyl tert-butyl ketone) as a desired substrate, much larger and more complex substrates are often evaluated in a directed evolution effort.

Figure 2:
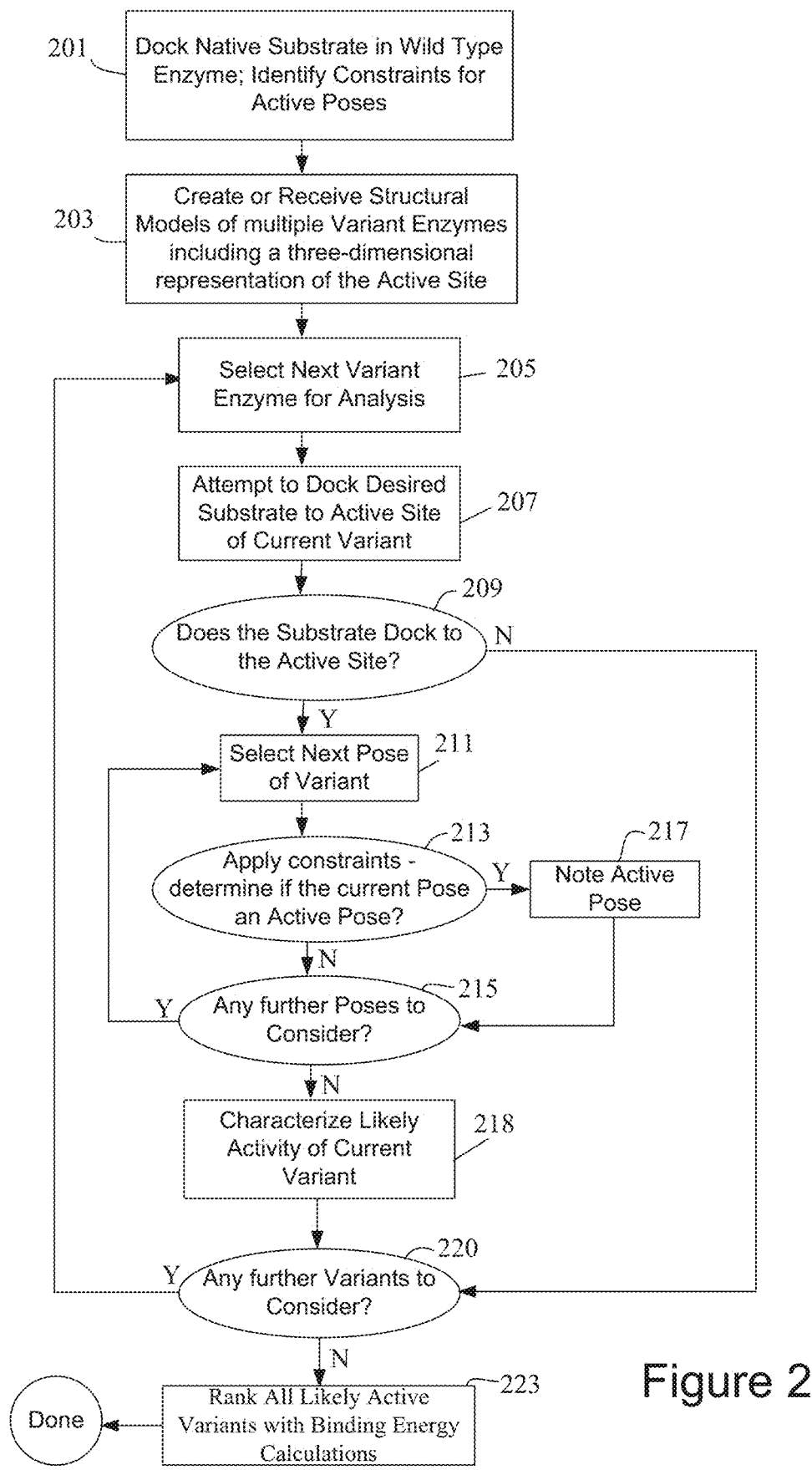
FIG. 2 is a flow chart presenting a workflow for analyzing potential activity of candidate biomolecules in some implementations.

FIG. 2 presents a workflow for analyzing the potential activity of candidate biomolecules in some implementations. While many different activities may be considered, the one that will be emphasized in this embodiment is catalytic transformation of the substrate. The transformation may be enantioselective or regioselective. In such case, the variants are enzymes. In the description of this Figure, when the term "substrate" is used, the concept extends to related ligands such as reaction intermediates or transition states that are important in a rate determining step in the catalytic transformation of the substrate to a reaction product.

As shown in FIG. 2, the process begins by identifying constraints for distinguishing active from inactive poses of the substrate. See block 201. In some cases, the constraints are identified by docking. In such processes, a researcher takes into consideration the interaction of the substrate or reaction intermediate or transition state with the enzyme active site. In the process, she identifies constraints that result in the desired activity (e.g., stereospecific catalytic transformation the substrate). The researcher may do this with the aid of structure analysis, a docking program and/or quantum mechanics calculations that present a representation of an enzyme and associated substrate, intermediate, or transition state. Docking done with a docker is sometimes referred to as an "empirical" docking approach and optimization done with a quantum mechanics tool is sometimes referred to as an "ab initio" approach. In some embodiments, the docking is performed with a wild type enzyme and the native substrate, intermediate, or transition state. See block 201. As explained above, some constraints are geometrical constraints representing the relative positions of moieties in the desired substrate and moieties in the native substrate or an associated cofactor as shown in the lower left corner of FIG. 1. In some implementations, constraints can be defined as relations between desired substrates and enzyme variants, such as the geometric constraints shown in the lower middle and right corner of FIG. 1.

In some cases, constraints for active poses can be identified by techniques other than docking a native substrate in a wild type enzyme. For instance, it is possible to identify moieties relevant for a catalytic reaction and define relations between the identified moieties using quantum mechanics and molecular dynamics tools.

Returning to the process shown in FIG. 2, the virtual protein screening system creates or receives structural models for each of multiple variant biomolecules that are to be considered for activity. See block 203. As explained, the structural models are three dimensional computationally-produced representations of the active sites or other aspects of the enzyme variants. These models may be saved for later use in a database or other data repository. In some cases, at least one of the models is created for use in the work flow. In some cases, at least one of the models was previously created, in which case the process simply receives such models.

Multiple models, each for a different biomolecule sequence are used in the process shown in FIG. 2. This should be contrasted with conventional work flows utilizing docking programs. Conventional work flows focus on a single target or sequence. In some cases, a conventional work flow considers multiple instances of a receptor, but these are based on the same sequence. Each of the instances has different three-dimensional coordinates generated from NMR or molecular dynamics simulations.

The structural models used in the FIG. 2 process may vary from one another by the insertion, deletion, or replacement in the models of one or more amino acid residues at positions associated with the active site or with some other position in the enzyme's sequence. Structural models may be created by various techniques. In one embodiment, they are created by homology modeling.

With the activity constraints and structural models in place, the virtual protein screening system iterates over the variants that have been selected for consideration. Control of the iteration is illustrated by a block 205, which indicates that the next variant enzyme under consideration is selected for analysis. This operation and the remaining operations of FIG. 2 may be implemented by software or digital logic.

For the variant enzyme currently under consideration, the virtual protein screening system first attempts to dock the desired substrate to the active site of the variant. See block 207. This process may correspond to a conventional docking procedure. Therefore, a docker may be employed to determine whether or not the substrate is capable of docking with active site in the variant. This decision is represented in a block 209. Note that the desired substrate is sometimes different from the native substrate, which may have been used to generate the constraints.

If the virtual protein screening system determines that docking is unlikely to be successful, process control is directed to a block 220, where the system determines whether there are any further variants to consider. If there are no further variants to consider, the process is completed with an optional operation 223, as indicated. If, on the other hand, one or more variants remain to be considered, process control is directed back to process step 205 where the next variant for consideration is selected. This variant is then evaluated for its ability to dock the substrate under consideration as described above with reference to blocks 207 and 209.

If it turns out that the variant under consideration can successfully dock with the substrate, process control is directed to a portion of the algorithm where multiple poses are considered and each evaluated for activity. As described below, this analysis is depicted by blocks 211, 213, 215, and 217.

As shown, the process iterates over multiple available poses. In various embodiments, a docker helps select the poses. As explained, dockers may generate numerous poses of a substrate in an active site. It may also rank poses based on one or more criteria such as docking score, energetic considerations, etc. Total energy and/or interaction energy may be considered, as described elsewhere. Regardless of how poses are generated and/or ranked, the work flow may be configured to consider a specified number of poses. The number of poses to be considered can be set arbitrarily. In one embodiment, at least about the top 10 poses are considered. In another embodiment, at least about 20 poses are considered, or at least about 50 poses, or at least about 100 poses. However, it is not intended that the present invention be limited to a specific number of poses.

As depicted at block 211, the process selects the next pose for analysis. The currently selected pose is then evaluated against the constraints identified in block 201, to determine whether the pose is an active pose. As explained, such constraints may be geometric constraints that determine whether one or more moieties of the substrate are located within the active site, such that the substrate is likely to undergo a desired catalytic transformation.

If the evaluation conducted at block 213 indicates that the current pose is not an active pose, the virtual protein screening system then determines whether there are any further poses to consider for the current variant under consideration. See block 215. Assuming that there are more poses to consider, process control is directed back to block 211, where the next pose is considered.

Assuming that the virtual protein screening system determines at block 213 that the pose under consideration is active, it notes this pose for later consideration. See block 217. In some embodiments, the virtual protein screening system may keep a running tally of the number of active poses for the variant currently under consideration.

After appropriately noting that the current pose is active, process control is directed to block 215, where the virtual protein screening system determines whether there are any further poses to consider. After repeating the consideration of all available poses for the variant under consideration, the virtual protein screening system determines that there are no further poses to consider and process control is directed to a block 218, which characterizes the likely activity of the current variant. Characterization can be made by various techniques, including but not limited to the number of active poses and associated docking scores for the variant under consideration and other considerations as described herein. After the operation of block 218 is complete, process control is directed to decision operation 220, which determines whether there are any further variants to consider. If there are additional variants to consider, process control is returned to block 205, where the workflow continues as described above.

After considering all variants in the workflow, the virtual protein screening system may rank them based on one or more criteria, such as the number of active poses the variants have, one or more docking scores of the active poses, and/or one or more binding energies of the active poses. See block 223. Only the poses identified as active poses (block 217) need to be evaluated in performing the ranking of block 223. In this way, the operations in the work flow serve to filter inactive poses from active poses and save computational effort associated with ranking the variants. While not shown in FIG. 2, variants may be selected for further investigation based on their rankings.

In certain embodiments, a protocol to calculate binding energies is executed to evaluate the energetics of each active pose of a variant. In some implementations, the protocol may consider van der Waals force, electrostatic interaction, and solvation energy. Solvation is typically not considered in calculations performed by dockers. Various solvation models are available for calculating binding energies, including, but not limited to distance dependent dielectrics, Generalized Born with pairwise summation (GenBorn), Generalized Born with Implicit Membrane (GBIM), Generalized Born with Molecular Volume integration (GBMV), Generalized Born with a simple switching (GBSW), and the Poisson-Boltzmann equation with non-polar surface area (PBSA). Protocols for calculating binding energies are different or separate from docker programs. They generally produce results that are more accurate than docking scores, due in part to the inclusion of solvation effects in their calculations. In various implementations, binding energies are calculated only for poses that are deemed to be active.

A. Generation of Models of Multiple Biomolecules Each Containing an Active Site

A computer system may provide three-dimensional models for a plurality of protein variants. The three-dimensional models are computational representations of some or all of the protein variants' full length sequences. Typically, at a minimum, the computation representations cover at least the protein variants' active sites.

In some cases, the three-dimensional models are homology models prepared using an appropriately designed computer system. The three-dimensional models employ a structural template in which the protein variants vary from one another in their amino acid sequences. Generally, a structural template is a structure previously solved by X-ray crystallography or NMR for a sequence that is homologous to the model sequence. The quality of the homology model is dependent on the sequence identity and resolution of the structure template. In certain embodiments, the three-dimensional models may be stored in a database for use as needed for current or future projects.

Three-dimensional models of the protein variants may be produced by techniques other than homology modeling. One example is protein threading, which also requires a structure template. Another example is ab initio- or de novo-protein modeling which does not require a structure template and is based on underlying physical principles. Examples of ab initio techniques include molecular dynamics simulations and simulations using the Rosetta software suite.

In some embodiments, the protein variants vary from one another in their active sites. In some cases, the active sites differ from one another by at least one mutation in the amino acid sequence of the active site. The mutation(s) may be made in a wild type protein sequence or some other reference protein sequence. In some cases, two or more of the protein variants share the same amino acid sequence for the active site but differ in the amino acid sequence for another region of the protein. In some cases, two protein variants differ from one another by at least about 2 amino acids, or at least about 3 amino acids, or at least about 4 amino acids. However, it is not intended that the present invention be limited to a specific number of amino acid differences between protein variants.

In certain embodiments, the plurality of variants includes members of library produced by one or more rounds of directed evolution. Diversity generation techniques used in directed evolution include gene shuffling, mutagenesis, recombination and the like. Examples of directed evolution techniques are described in US Patent Application Publ. No. 2006/0223143, which is incorporated herein by reference in its entirety.

In some implemented processes, the plurality of variants include at least about ten different variants, or at least about 100 different variants, or at least about one thousand different variants. However, it is not intended that the present invention be limited to a specific number of protein variants.

B. Evaluating a Ligand in Multiple Different Protein Variants

As explained herein, docking is conducted by an appropriately programmed computer system that uses a computational representation of a ligand and computational representations of the active sites of the generated plurality of variants.

As an example, a docker may be configured to perform some or all of the following operations:
1. Generate a set of ligand conformations using high-temperature molecular dynamics with random seeds. The docker may generate such conformations without consideration of the ligand's environment. Hence, the docker may identify favorable conformations by considering only internal strain or other considerations specific to the ligand alone. The number of conformations to be generated can be set arbitrarily. In one embodiment, at least about 10 conformations are generated. In another embodiment, at least about 20 conformations are generated, or at least about 50 conformations, or at least about 100 conformations. However, it is not intended that the present invention be limited to a specific number of conformations.
2. Generate random orientations of the conformations by translating the center of the ligand to a specified location within the receptor active site, and performing a series of random rotations. The number of orientations to refine can be set arbitrarily. In one embodiment, at least about 10 orientations are generated. In another embodiment, at least about 20 orientations are generated, or at least about 50 orientations, or at least about 100 orientations. However, it is not intended that the present invention be limited to any specific number of orientations. In certain embodiments, the docker calculates a "softened" energy to generate further combinations of orientation and conformation. The docker calculates softened energy using physically unrealistic assumptions about the permissibility of certain orientations in an active site. For example, the docker may assume that ligand atoms and active site atoms can occupy essentially the same space, which is impossible based on Pauli repulsion and steric considerations. This softened assumption can be implemented by, for example, employing a relaxed form of the Lennard-Jones potential when exploring conformation space. By using a softened energy calculation, the docker allows a more complete exploration of conformations than available using physically realistic energy considerations. If the softened energy of a conformation in a particular orientation is less than a specified threshold, the conformation-orientation is kept. These low energy conformations are retained as "poses". In certain implementations, this process continues until either a desired number of low-energy poses is found, or a maximum number of bad poses is found.
3. Subject each retained pose from step 2 to simulated annealing molecular dynamics to refine the pose. The temperature is increased to a high value then cooled to the target temperature. The docker may do this to provide a more physically realistic orientation and/or conformation than is provided by the softened energy calculation.
4. Perform a final minimization of the ligand in the rigid receptor using non-softened potential. This provides a more accurate energy value for the retained poses. However, the calculation may provide only partial information about the poses' energies.
5. For each final pose, calculate the total energy (receptor-ligand interaction energy plus ligand internal strain) and the interaction energy alone. The calculation may be performed using CHARMm. The poses are sorted by CHARMm energy and the top scoring (most negative, thus favorable to binding) poses are retained. In some embodiments, this step (and/or step 4) removes poses that are energetically unfavorable.

The following reference provides an example of a docker's functioning: Wu et al., *Detailed Analysis of Grid-Based Molecular Docking: A Case Study of CDOCKER—A CHARMm-Based MD Docking Algorithm*, J. Computational Chem., Vol. 24, No. 13, pp 1549-62 (2003), which is incorporated herein by reference in its entirety.

A docker such as the one described here may provide one or more pieces of information used by the screening system to identify high-performing variants. Such information includes the identity of variants for which docking with the desired substrate is unlikely. Such variants need not be evaluated for activity, etc. Other information provided by the docker includes sets of poses (one set for each variant) that can be considered for activity. Still other information includes docking scores of the poses in the sets.

C. Determine Whether Poses of the Docked Ligand are Active

For a protein variant that successfully docks with the ligand, the virtual protein screening system makes the following operations: (i) consider a plurality of poses of the computational representation of the ligand in the active site of the protein variant under consideration, and (ii) determine which if any of the plurality of poses is active.

An active pose is one meeting one more constraints for the ligand to bind under defined conditions (rather than arbitrary binding condition). If the ligand is a substrate and the protein is an enzyme, active binding may be binding that allows the substrate to undergo a catalyzed chemical transformation, particularly a stereo-specific transformation. In some implementations, the constraints are geometrical constraints defining a range of relative positions of one or more atoms in the ligand and one or more atoms in the protein and/or cofactor associated with the protein.

In some cases, constraints are identified from one or more conformations of a native substrate and/or subsequent intermediate when it undergoes a catalyzed chemical transformation by a wild type enzyme. In certain embodiments, the constraints include (i) a distance between a particular moiety on the substrate and/or subsequent intermediate and a particular residue or residue moiety in the active site, (ii) a distance between a particular moiety on the substrate and/or subsequent intermediate and a particular cofactor in the active site, and/or (iii) a distance between a particular moiety on the substrate and/or subsequent intermediate and a particular moiety on an ideally positioned native substrate, and/or subsequent intermediate in the active site. In certain embodiments, the constraints can include angles between chemical bonds, torsion around axes, or strain at chemical bonds.

The plurality of poses of the computational representation of the substrate and/or subsequent intermediate may be generated with respect to a computational representation of the protein variant under consideration. The plurality of poses may be generated by various techniques. General examples of such techniques include systematic or stochastic torsional searches about rotatable bonds, molecular dynamics simulations, and genetic algorithms designed to locate low energy conformations. In one example, the poses are generated using high temperature molecular dynamics, followed by random rotation, refinement by grid-based simulated annealing, and a final grid-based or force field minimization to generate a conformation and/or orientation of the substrate and/or subsequent intermediate in the computational representation active site. Some of these operations are optional, e.g., refinement by grid-based simulated annealing, and grid-based or force field minimization.

In certain embodiments, the number of poses considered is at least about 10, or at least about 20, or at least about 50, or at least about 100, or at least about 200, or at least about 500. However, it is not intended that the present invention be limited to a specific number of poses considered.

If the project is successful, at least one of the variants is determined to have one or more poses that are active and energetically favorable. In certain embodiments, a variant selected for further consideration is one determined to have large numbers of active conformations in comparison with other variants. In certain embodiments, the variants are selected by ranking the variants based on the number of active poses they have, one or more docking scores for the active poses, and/or one or more binding energies of the active poses. As examples, the types of docking scores that may be considered include scores based on van de Waals force and/or electrostatics interaction. As examples, the types of binding energies that may be considered include van der Waals force, electrostatic interaction, and solvation energy.

A protein variant determined to support one or more active poses may be selected for further investigation, synthesis, production, etc. In one example, a selected protein variant is used to seed one or more rounds of directed evolution. As an example, a round of directed evolution may include (i) preparing a plurality of oligonucleotides containing or encoding at least a portion of the selected protein variant, and (ii) performing a round of directed evolution using the plurality of oligonucleotides. The oligonucleotides may be prepared by any suitable means, including but not limited to gene synthesis, fragmentation of a nucleic acid encoding some or all of the selected protein variant, etc. In certain embodiments, the round of directed evolution includes fragmenting and recombining the plurality of oligonucleotides. In certain embodiments, the round of directed evolution includes performing saturation mutagenesis on the plurality of oligonucleotides Catalyzed chemical transformations that may be screened using constraints include, but are not limited to for example, ketone reduction, transamination, oxidation, nitrile hydrolysis, imine reduction, enone reduction, acyl hydrolysis, and halohydrin dehalogenation. Examples of enzyme classes that may provide the multiple variants evaluated using constraints include, but are not limited to: ketone reductases, transaminases, cytochrome P450s, Baeyer-Villiger monooxygenases, monoamine oxidases, nitrilases, imine reductases, enone reductases, acylases, and halohydrin dehalogenases. In the context of rational ligand design, optimization of targeted covalent inhibition (TCI) is a type of activity that may be screened for using constraints. An example of a TCI application is described in Singh et al., *The resurgence of covalent drugs*, Nature Reviews Drug Discovery, vol. 10, pp. 307-317 (2011), which is incorporated herein by reference in its entirety. In some implementations, the TCI activity is found by identifying a nucleophilic amino acid (e.g., cysteine) in a protein. The process described herein can help identify inhibitors that satisfy constraints defining an ideal orientation of an electrophilic moiety important for the inhibition (a putative inhibitor) that can react with the biomolecule to be inhibited.

III. USING THE VIRTUAL PROTEIN SCREENING SYSTEM TO DESIGN ENZYMES

Some embodiments provide processes for virtually modeling and screening enzymes using a virtual protein screening system, thereby identifying enzymes having desired properties, e.g., catalytic activity and selectivity. In some embodiments, a family of actual enzymes can be virtually modeled and screened as an initial variant library. Some embodiments can iteratively use one or more enzymes selected by virtual screening from the initial library as parent polypeptides or reference sequences to generate a new variant library by in silico, in vitro, or in vivo techniques. In some embodiments, one or more enzymes ranked highly by the system as described herein are selected as parent polypeptide(s). The new variant library includes protein sequences that are different from the sequences of the parent polypeptides, and/or can be used as precursors to introduce subsequent variation(s).

In some embodiments, the parent polypeptides are modified in a directed evolution procedure by performing mutagenesis and/or a recombination-based diversity generation mechanism to generate the new library of protein variants. In some embodiments, the parent polypeptides are altered by at least one substitution, insertion, cross-over, deletion, and/or other genetic operation. The directed evolution may be implemented directly on the polypeptides (e.g., in an in silico process) or indirectly on the nucleic acids encoding the polypeptides (e.g., in an in vitro process). The new library may be used to generate new homology models for further screening and directed evolution.

In some embodiments, the modeling, screening, and evolution of enzymes are carried out iteratively in silico until one or more enzymes meeting certain criteria are met. For instance, the criteria may be a specified binding energy or score, or an improvement thereof. Other embodiments may combine in silico and physical (e.g., in vitro or in vivo) techniques. For instance, it is possible to start an enzyme design process using enzymes derived by in vitro screening and sequencing. In vitro sequencing may be performed by next-generation sequencing. Then, the enzyme design process may use in silico methods for directed evolution, modeling, and further screening. The process can finally use in vitro and/or in vivo techniques to validate an enzyme in a biological system. Other combinations and orders of in silico and physical techniques are suitable for various applications. Indeed, it is not intended that the present invention be limited to any specific combination and/or order of methods.

In some embodiments, preparation of polypeptide sequences is achieved in silico. In other embodiments, polypeptides are generated by synthesizing oligonucleotides or nucleic acid sequences using a nucleic acid synthesizer and translating the nucleotide sequences to obtain the polypeptides.

As stated above, in some embodiments, the selected enzyme may be modified by performing one or more recombination-based diversity generation mechanisms to generate the new library of protein variants. Such recombination mechanisms include, but are not limited to, e.g., shuffling, template switching, Gene Splicing by Overlap Extension, error-prone PCR, semi-synthetic combinatorial libraries of residues, recursive sequence recombination ("RSR") (See e.g., US Patent Application Publ. No. 2006/0223143, incorporated by reference herein in its entirety). In some embodiments, some of these recombination mechanisms may be implemented in vitro. In some embodiments, some of these recombination mechanisms may be implemented computationally in silico to mimic the biological mechanisms.

Some embodiments include selecting one or more positions in a protein sequence and conducting site-directed mutation methods such as saturation mutagenesis at the one or more positions so selected. In some embodiments, the positions are selected by evaluating the structure of the active site and/or constraints related to the catalytic reaction as discussed elsewhere in the document. Combining virtual screening with sequence-activity modeling finds use in some embodiments. In these embodiments, the process of directed evolution may select the positions by evaluating the coefficients of the terms of a sequence-activity model, thereby identifying one or more of residuals that contribute to the activity of interest. U.S. Pat. No. 7,783,428 (herein incorporated by reference in its entirety) provides examples of sequence activity models that can be used to identify amino acids for mutagenesis.

In some embodiments, the method involves selecting one or more members of the new protein variant library for production. One or more of these variants may then be synthesized and/or expressed in an expression system. In a specific embodiment, the method continues in the following manner: (i) providing an expression system from which a selected member of the new protein variant library can be expressed; and (ii) expressing the selected member of the new protein variant library.

Figure 3A:
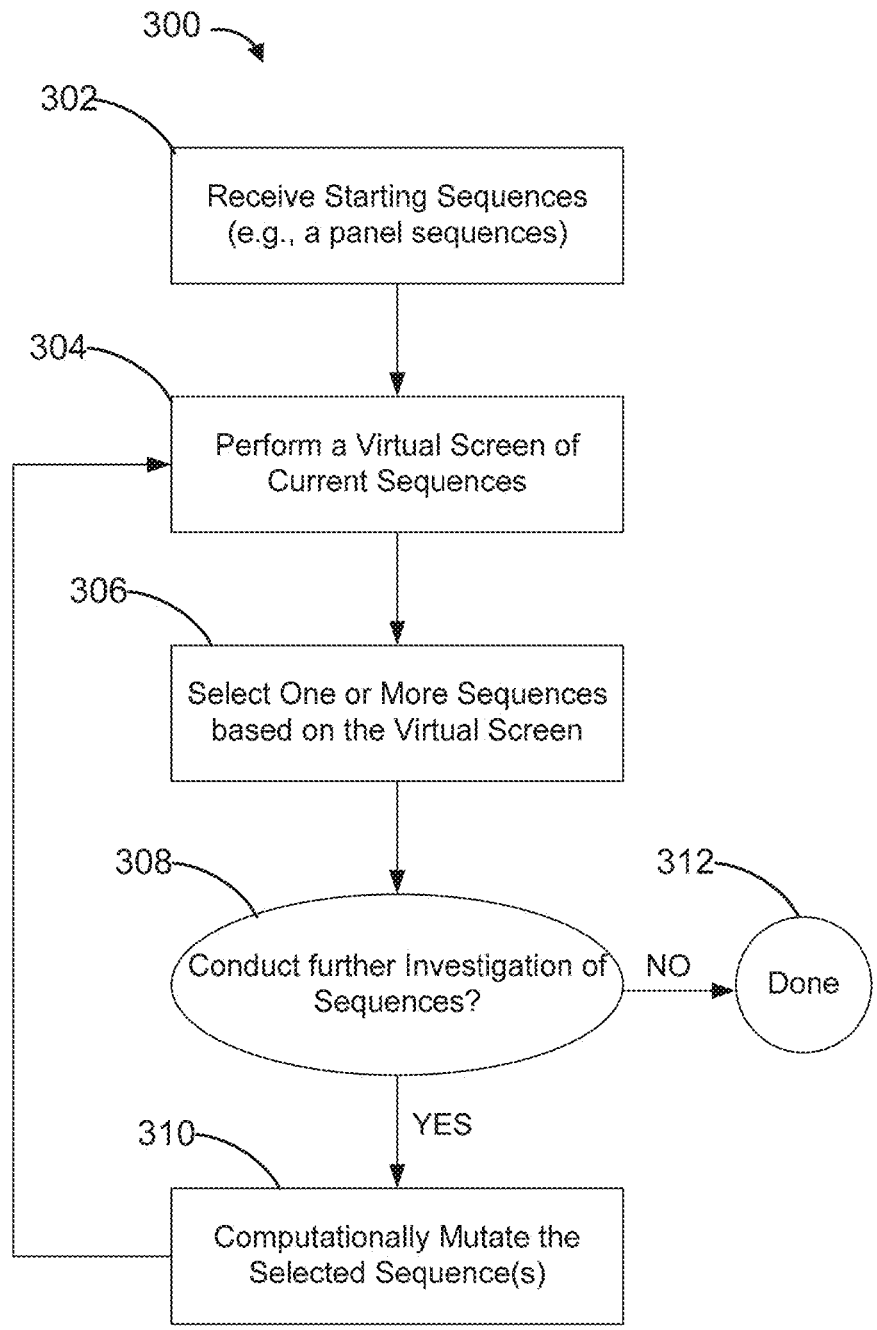
FIG. 3A is a flowchart showing an example of a workflow for designing biomolecule sequences according to some embodiments of the disclosure.
Figure 3B:
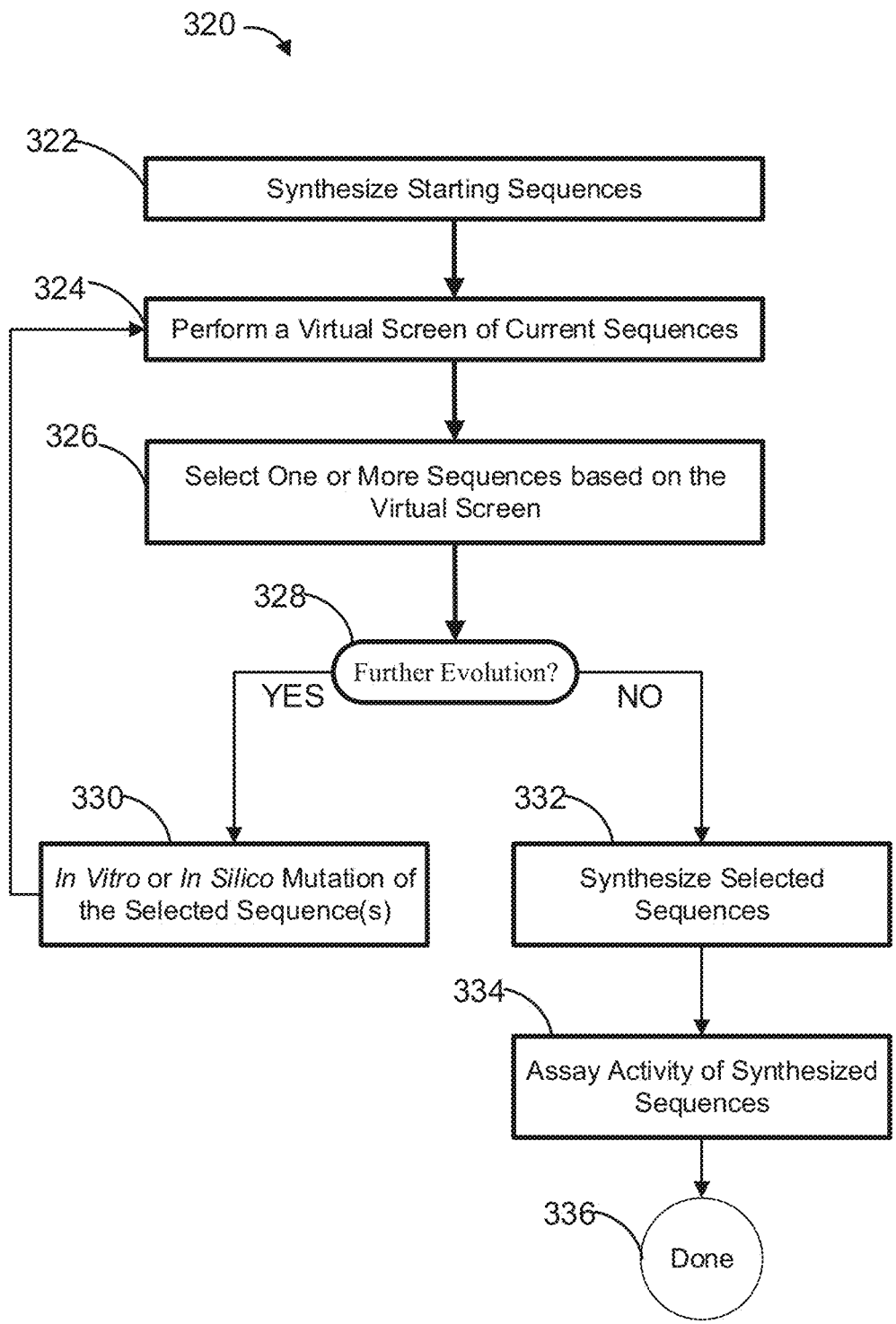
FIG. 3B is a flowchart showing an example of a workflow for designing biomolecule sequences, which involves synthesizing and assaying sequences obtained from virtual screening.
Figure 3C:
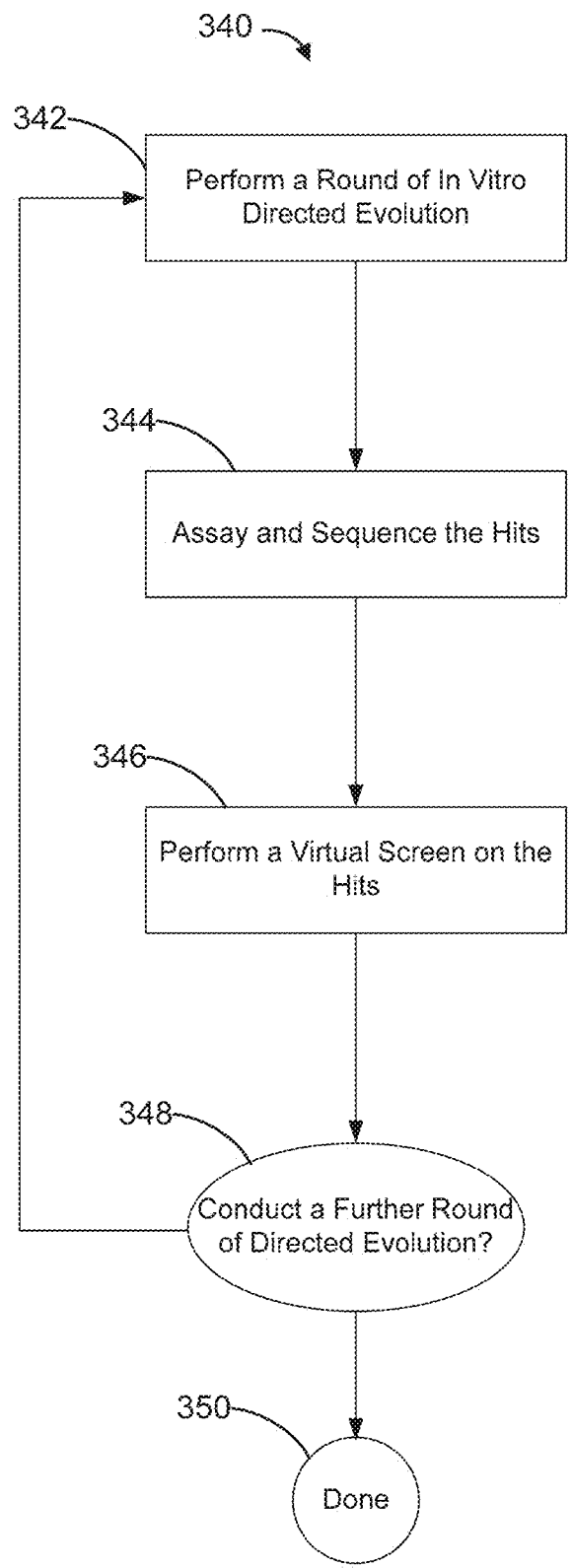
FIG. 3C is a flowchart showing an example of a workflow for designing biomolecule sequences, which combines in vitro directed evolution and virtual screening in each round of multiple iterations.

FIGS. 3A-3C are flowcharts showing examples of workflows for designing biomolecule sequences, which implement various combinations of elements described elsewhere herein. FIG. 3A shows a flowchart for a process 300 that starts by receiving sequence information of multiple starting sequences from a panel of biomolecules, such as a panel of enzymes. See block 302. The process then performs a virtual screening of the currently received sequences using a virtual protein screening system. See block 304. In some embodiments, the virtual protein screening system can create three-dimensional homology models of the starting sequences, and dock one or more substrates with the homology models by considering poses of the substrates as described above, thereby generating docking scores for the starting sequences. The virtual protein screening system can also calculate interaction energy and internal energy of the docking participants (the enzymes and the substrates). Moreover, the virtual protein screening system can evaluate various constraints of poses to determine whether the poses are active, i.e. the substrates bind with the enzyme in a manner that is likely to cause a catalytic conversion of the substrate. Furthermore, in some embodiments, evaluation of the constraints also provides inference regarding whether the products of the catalytic reaction is enantioselective and/or regioselective. In some embodiments, the process selects one or more sequences based on the binding energy, activity, and selectivity determined by the virtual screening system. See block 306. The process then evaluates whether it is necessary to conduct further investigation of the selected sequences in step 308. If so, the process in this example computationally mutates the selected sequences. The mutations are based on the various diversity generation mechanisms described above, such as mutagenesis or recombination. See block 310. The computationally mutated sequences are then provided for a new round of virtual screening by the virtual protein screening system. See block 304. The virtual screening and selection may carry on for iterations, until no further investigation of sequences are necessary, which may be determined by preset criteria such as a specific number of iterations and/or a particular level of desired activity. At which point, the process of designing biomolecules (e.g., enzymes) is finished at step 312.

FIG. 3B shows a flowchart for a process 320 for directed evolution of biomolecules such as enzymes, which process has some similar and some different elements compared to process of 300. Process 320 starts by in vitro synthesis of multiple starting sequences of biomolecules (e.g., enzymes), which may be necessary or useful when a pre-existing panel of biomolecules is not available. See block 322. The synthesized sequences may also be assayed to collect data for the sequences, which data may be useful for designing biomolecules of desired properties, in which data cannot be obtained by the virtual screening system. The process then performs a virtual screening of the synthesized sequences using a virtual protein screening system, depicted in block 324, which is similar to step 304 in process 300. The process then selects one or more sequences based on the binding energy, activity, and selectivity determined by the virtual screening system. See block 326. The process then evaluates whether it is necessary to perform further directed evolution of the selected sequences in step 328. If so, the process in this example mutates the selected sequences in silico or in vitro. The mutations are based on the various diversity generation mechanisms described above. See block 330. The mutated sequences are then provided for a new round of virtual screening by the virtual protein screening system. See block 324. The virtual screening and selection may carry on for iterations, until no further evolution of sequences are necessary, which may be determined by preset criteria such as a specific number of iterations and/or a particular level of desired activity. At which point, the sequences selected by the virtual screening system are synthesized and expressed to produce actual enzymes. See block 332. The produced enzymes can be assayed for activities of interest, which can be used to validate the results of the virtual screening process. See block 334. After the assay, the directed evolution process is concluded at step 336.

FIG. 3C shows a flowchart for a process 340 for directed evolution of biomolecules such as enzymes. Process 340 starts by in vitro directed evolution to derive multiple starting sequences of biomolecules (e.g., enzymes). See block 342. As in process 320, the derived sequences are assayed to determine whether the sequences meet certain criteria, such as desired activity or selectivity. Sequences meeting the criteria are determined as hits for further development. See block 344. The process then performs a virtual screening of the hits using a virtual protein screening system, depicted in block 346, which is similar to step 304 in process 300. In some embodiments, the process also selects one or more sequences based on the binding energy, activity, and selectivity determined by the virtual screening system as described above. The process then evaluates whether it is necessary to perform further round of directed evolution of the selected sequences in step 348. If so, the process in provides the selected sequences for a further round of in vitro directed evolution in a new iteration, see block 342. The virtual screening and selection may carry on for iterations, until no further evolution of sequences are necessary, which may be determined by preset criteria. At which point, the process of designing biomolecules (e.g., enzymes) is finished at step 350.

IV. GENERATING A PROTEIN VARIANT LIBRARY

Protein variant libraries comprise groups of multiple proteins having one or more residues that vary from member to member in a library. These libraries may be generated using the methods described herein and/or any suitable means known in the art. In various embodiments, these libraries provide candidate enzymes for the virtual protein screening system. In some embodiments, the libraries may be provided and screened in silico in initial rounds, and resulting proteins selected by the virtual screening system from a later or final round may be sequenced and/or screened in vitro. Because the initial rounds of screening are performed in silico, the time and cost for screening can be reduced significantly. The number of proteins included in a protein variant library can be easily increased in the initial rounds of screening in some implementations compared to conventional physical screening. It is not intended that the present disclosure be limited to any particular number of proteins in the protein libraries used in the methods of the present disclosure. It is further not intended that the present disclosure be limited to any particular protein variant library or libraries.

In one example, the protein variant library is generated from one or more naturally occurring proteins, which may be encoded by a single gene family in some embodiments, or a panel of enzymes in other embodiments. Other starting points include, but are not limited to recombinants of known proteins and/or novel synthetic proteins. From these "seed" or "starting" proteins, the library may be generated by various techniques. In one case, the library is generated by virtual processes that reflect biological or chemical techniques, e.g., DNA fragmentation-mediated recombination as described in Stemmer (1994) Proceedings of the National Academy of Sciences, USA, 10747-10751 and WO 95/22625 (both of which are incorporated herein by reference), synthetic oligonucleotide-mediated recombination as described in Ness et al. (2002) Nature Biotechnology 20:1251-1255 and WO 00/42561 (both of which are incorporated herein by reference), or nucleic acids encoding part or all of one or more parent proteins. Combinations of these methods may be used (e.g., recombination of DNA fragments and synthetic oligonucleotides) as well as other recombination-based methods known in the art, for example, WO97/20078 and WO98/27230, both of which are incorporated herein by reference. Any suitable methods used to generate protein variant libraries find use in the present disclosure. Indeed, it is not intended that the present disclosure be limited to any particular method for producing variant libraries.

In some embodiments, a single "starting" sequence (which may be an "ancestor" sequence) may be employed for purposes of defining a group of mutations used in the modeling process. In some embodiments, there is more than one starting sequence. In some additional embodiments, at least one of the starting sequences is a wild-type sequence. In certain embodiments, the mutations are (a) identified in the literature as affecting substrate specificity, selectivity, stability, and/or any other property of interest and/or (b) computationally predicted to improve protein folding patterns (e.g., packing the interior residues of a protein), improve ligand binding, improve subunit interactions, or improve family shuffling methods between multiple diverse homologs, etc. It is not intended that the present invention be limited to any specific choice of property/ies of interest or function(s).

In some embodiments, the mutations may be virtually introduced into the starting sequence and the proteins may be virtually screened for beneficial properties. Site-directed mutagenesis is one example of a useful technique for introducing mutations, although any suitable method finds use. Thus, alternatively or in addition, the mutants may be provided by gene synthesis, saturating random mutagenesis, semi-synthetic combinatorial libraries of residues, directed evolution, recursive sequence recombination ("RSR") (See e.g., US Patent Application Publ. No. 2006/0223143, incorporated by reference herein in its entirety), gene shuffling, error-prone PCR, and/or any other suitable method. One example of a suitable saturation mutagenesis procedure is described in US Patent Application Publ. No. 2010/0093560, which is incorporated herein by reference in its entirety.

The starting sequence need not be identical to the amino acid sequence of a wild type protein. However, in some embodiments, the starting sequence is the sequence of a wild type protein. In some embodiments, the starting sequence includes mutations not present in the wild-type protein. In some embodiments, the starting sequence is a consensus sequence derived from a group of proteins having a common property, e.g., a family of proteins.

In some embodiments, catalyzed chemical transformations that may be screened using the virtual screening system include but are not limited to, for example, ketone reduction, transamination, oxidation, nitrile hydrolysis, imine reduction, enone reduction, acyl hydrolysis, and halohydrin dehalogenation. Examples of enzyme classes that may provide the multiple variants evaluated include, but are not limited to, ketone reductases, transaminases, cytochrome P450s, Baeyer-Villiger monooxygenases, monoamine oxidases, nitrilases, imine reductases, enone reductases, acylases, and halohydrin dehalogenases.

A non-limiting representative list of families or classes of enzymes which may serve as sources of parent sequences includes, but is not limited to, the following: oxidoreductases (E.C.1); transferases (E.C.2); hydrolyases (E.C.3); lyases (E.C.4); isomerases (E.C.5) and ligases (E.C. 6). More specific but non-limiting subgroups of oxidoreductases include dehydrogenases (e.g., alcohol dehydrogenases (carbonyl reductases), xylulose reductases, aldehyde reductases, farnesol dehydrogenase, lactate dehydrogenases, arabinose dehydrogenases, glucose dehyrodgenase, fructose dehydrogenases, xylose reductases and succinate dehyrogenases), oxidases (e.g., glucose oxidases, hexose oxidases, galactose oxidases and laccases), monoamine oxidases, lipoxygenases, peroxidases, aldehyde dehydrogenases, reductases, long-chain acyl-[acyl-carrier-protein] reductases, acyl-CoA dehydrogenases, ene-reductases, synthases (e.g., glutamate synthases), nitrate reductases, mono and di-oxygenases, and catalases. More specific but non-limiting subgroups of transferases include methyl, amidino, and carboxyl transferases, transketolases, transaldolases, acyltransferases, glycosyltransferases, transaminases, transglutaminases and polymerases. More specific but non-limiting subgroups of hydrolases include ester hydrolases, peptidases, glycosylases, amylases, cellulases, hemicellulases, xylanases, chitinases, glucosidases, glucanases, glucoamylases, acylases, galactosidases, pullulanases, phytases, lactases, arabinosidases, nucleosidases, nitrilases, phosphatases, lipases, phospholipases, proteases, ATPases, and dehalogenases. More specific but non-limiting subgroups of lyases include decarboxylases, aldolases, hydratases, dehydratases (e.g., carbonic anhydrases), synthases (e.g., isoprene, pinene and farnesene synthases), pectinases (e.g., pectin lyases) and halohydrin dehydrogenases. More specific, but non-limiting subgroups of isomerases include racemases, epimerases, isomerases (e.g., xylose, arabinose, ribose, glucose, galactose and mannose isomerases), tautomerases, and mutases (e.g. acyl transferring mutases, phosphomutases, and aminomutases. More specific but non-limiting subgroups of ligases include ester synthases. Other families or classes of enzymes which may be used as sources of parent sequences include transaminases, proteases, kinases, and synthases. This list, while illustrating certain specific aspects of the possible enzymes of the disclosure, is not considered exhaustive and does not portray the limitations or circumscribe the scope of the disclosure.

In some cases, the candidate enzymes useful in the methods described herein are capable of catalyzing an enantioselective reaction such as an enantioselective reduction reaction, for example. Such enzymes can be used to make intermediates useful in the synthesis of pharmaceutical compounds for example.

In some embodiments, the candidate enzymes are selected from endoxylanases (EC 3.2.1.8); β-xylosidases (EC 3.2.1.37); alpha-L-arabinofuranosidases (EC 3.2.1.55); alpha-glucuronidases (EC 3.2.1.139); acetylxylanesterases (EC 3.1.1.72); feruloyl esterases (EC 3.1.1.73); coumaroyl esterases (EC 3.1.1.73); alpha-galactosidases (EC 3.2.1.22); beta-galactosidases (EC 3.2.1.23); beta-mannanases (EC 3.2.1.78); beta-mannosidases (EC 3.2.1.25); endo-polygalacturonases (EC 3.2.1.15); pectin methyl esterases (EC 3.1.1.11); endo-galactanases (EC 3.2.1.89); pectin acetyl esterases (EC 3.1.1.6); endo-pectin lyases (EC 4.2.2.10); pectate lyases (EC 4.2.2.2); alpha rhamnosidases (EC 3.2.1.40); exo-poly-alpha-galacturonosidase (EC 3.2.1.82); 1,4-alpha-galacturonidase (EC 3.2.1.67); exopolygalacturonate lyases (EC 4.2.2.9); rhamnogalacturonan endolyases EC (4.2.2.B3); rhamnogalacturonan acetylesterases (EC 3.2.1.B11); rhamnogalacturonan galacturonohydrolases (EC 3.2.1.B11); endo-arabinanases (EC 3.2.1.99); laccases (EC 1.10.3.2); manganese-dependent peroxidases (EC 1.10.3.2); amylases (EC 3.2.1.1), glucoamylases (EC 3.2.1.3), proteases, lipases, and lignin peroxidases (EC 1.11.1.14). Any combination of one, two, three, four, five, or more than five enzymes find use in the compositions of the present disclosure. It is not intended that the present invention be limited to any particular number of enzymes and/or enzyme classes.

It is not intended that the present invention be limited to any particular method for generating systematically varied sequences, as any suitable method finds use. In one or more embodiments of the disclosure, a single starting sequence is modified in various ways to generate the library. In some embodiments, the library is generated by systematically varying the individual residues of the starting sequence. The set of systematically varied sequences of a library can be designed a priori using design of experiment (DOE) methods to define the sequences in the data set. A description of DOE methods can be found in Diamond, W. J. (2001) Practical Experiment Designs: for Engineers and Scientists, John Wiley & Sons and in "Practical Experimental Design for Engineers and Scientists" by William J Drummond (1981) Van Nostrand Reinhold Co New York, "Statistics for experimenters" George E. P. Box, William G Hunter and J. Stuart Hunter (1978) John Wiley and Sons, New York, or, e.g., on the World Wide Web at itl.nist.gov/div898/handbook/. There are several computational packages available to perform the relevant mathematics, including Statistics Toolbox (MATLAB®), JMP®, STATISTICA®, and STAT-EASE® DESIGN EXPERT®. The result is a systematically varied and orthogonal dispersed data set of sequences that is suitable for screening by the virtual protein screening system disclosed herein. DOE-based data sets can also be readily generated using either Plackett-Burman or Fractional Factorial Designs, as known in the art. Diamond, W. J. (2001).

Because initial rounds of screening can be performed in silico with high efficiency, some embodiments may use some or all available sequences to provide the protein variant library when the number of variants is usually too large to be screened with conventional physical methods. For instance, for a sequence with 15 positions, each having 20 possible amino acids, there are 300 possible positions vs. amino acid pairs, and $\Sigma_{r=1}^{300}(_{r}^{300})$ different variant sequences. In some implementations, a library can include hundreds, thousands, tens of thousands, hundreds of thousands, or more variants from this possible pool depending on the available computing power and application needs. It is not intended that the present disclosure be limited to any particular number of variant in the libraries.

V. SEQUENCING PROTEIN VARIANTS

In some embodiments, physical protein variants are used to generate computational models of active sites of the protein variants used in virtual screening as described above. In some embodiments, protein variants obtained from virtual screening are physically generated using various methods described above. In some embodiments, the physically generated protein variants are assayed for their reaction against one or more ligands of interest. In various embodiments, the sequences of the physical protein variants are ascertained by protein sequencing methods, some of which methods are further described below.

Protein sequencing involves determining the amino acid sequence of a protein. Some protein sequencing techniques also determine conformation the protein adopts, and the extent to which it is complexed with any non-peptide molecules. Mass spectrometry and the Edman degradation reaction may be used to directly determine the sequence of amino acids of a protein.

The Edman degradation reaction allows the ordered amino acid composition of a protein to be discovered. In some embodiments, automated Edman sequencers can be used to determine the sequence of protein variants. Automated Edman sequencers are able to sequence peptides of increasingly longer sequences, e.g., up to approximately 50 amino acids long. In some embodiments, a protein sequencing process implementing Edman degradation involves one or more of the following:

- Break disulfide bridges in the protein with a reducing agent, e.g., 2-mercaptoethanol. A protecting group such as iodoacetic acid may be used to prevent bonds from re-forming
- Separate and purify individual chains of the protein complex if there are more than one
- Determine the amino acid composition of each chain
- Determine the terminal amino acids of each chain
- Break each chain into fragments, e.g., fragments under 50 amino acids long.
- Separate and purify the fragments
- Determine the sequence of each fragment using the Edman degradation reaction
- Repeat the above steps applying a different pattern of cleavage to provide additional read(s) of amino acid sequences
- Construct the sequence of the overall protein from amino acid sequence reads In various implementations, peptides longer than about 50-70 amino acids are to be broken up into small fragments to facilitate sequencing by Edman reactions. Digestion of longer sequences can be performed by endopeptidases such as trypsin or pepsin, or by chemical reagents such as cyanogen bromide. Different enzymes give different cleavage patterns, and the overlap between fragments can be used to construct an overall sequence.

During the Edman degradation reaction, the peptide to be sequenced is adsorbed onto a solid surface of a substrate. In some embodiments, one suitable substrate is glass fiber coated with polybrene, a cationic polymer. The Edman reagent, phenylisothiocyanate (PITC), is added to the adsorbed peptide, together with a mildly basic buffer solution of trimethylamine. This reaction solution reacts with the amine group of the N-terminal amino acid. The terminal amino acid can then be selectively detached by the addition of anhydrous acid. The derivative then isomerises to give a substituted phenylthiohydantoin, which can be washed off and identified by chromatography. Then the cycle can be repeated.

In some embodiments, mass spectrometry can be used to determine an amino acid sequence by determining the mass-to-charge ratios of fragments of the amino acid sequence. The mass spectrum including peaks corresponding to multiply charged fragments can be determined, where the distance between the peaks corresponding to different isotope is inversely proportional to the charge on the fragment. The mass spectrum is analyzed, e.g., by comparison against a database of previously sequenced proteins to determine the sequences of the fragments. This process is then repeated with a different digestion enzyme, and the overlaps in the sequences are used to construct a complete amino acid sequence.

Peptides are often easier to prepare and analyze for mass spectrometry than whole proteins. In some embodiments, electrospray ionization is used for delivering the peptides to the spectrometer. The protein is digested by an endoprotease, and the resulting solution is passed through a high-pressure liquid chromatography column. At the end of this column, the solution is sprayed into the mass spectrometer, the solution being charged with a positive potential. The charge on solution droplets causes them to fragment into single ions. The peptides are then fragmented and the mass-to-charge ratios of the fragments measured.

It is also possible to indirectly determine an amino acid sequence from the DNA or mRNA sequence encoding the protein. Nucleic acid sequencing methods, e.g., various next generation sequencing methods, may be used to determine DNA or RNA sequences. In some implementations, a protein sequence is newly isolated without knowledge of the nucleotides encoding the protein. In such implementations, one may first determine a short polypeptide sequence using one of the direct protein sequencing methods. A complementary marker for the protein's RNA can be determined from this short sequence. This can then be used to isolate the mRNA coding for the protein, which can then be replicated in a polymerase chain reaction to yield a significant amount of DNA, which can then be sequenced using DNA sequencing methods. The amino acid sequence of the protein can then be deduced from the DNA sequence. In the deduction, it is necessary to take into account the amino acids removed after the mRNA has been translated.

In one or more embodiments, nucleic acid sequence data can be used in various stages in the process of directed evolution of proteins. In one or more embodiments, sequence data can be obtained using bulk sequencing methods including, for example. Sanger sequencing or Maxam-Gilbert sequencing, which are considered the first generation sequencing methods. Sanger sequencing, which involves using labeled dideoxy chain terminators, is well known in the art; see, e.g., Sanger et al., Proceedings of the National Academy of Sciences of the United States of America 74, 5463-5467 (1997). Maxam-Gilbert sequencing, which involves performing multiple partial chemical degradation reactions on fractions of the nucleic acid sample followed by detection and analysis of the fragments to infer the sequence, is also well known in the art; see, e.g., Maxam et al., Proceedings of the National Academy of Sciences of the United States of America 74, 560-564 (1977). Another bulk sequencing method is sequencing by hybridization, in which the sequence of a sample is deduced based on its hybridization properties to a plurality of sequences, e.g., on a microarray or gene chip; see, e.g. Drmariac, et al., Nature Biotechnology 16, 54-58 (1998).

In one or more embodiments, nucleic acid sequence data is obtained using next-generation sequencing methods. Next-generation sequencing is also referred to as high-throughput sequencing. The techniques parallelize the sequencing process, producing thousands or millions of sequences at once. Examples of suitable next-generation sequencing methods include, but are not limited to, single molecule real-time sequencing (e.g., Pacific Biosciences of Menlo Park, Calif.), Ion semiconductor sequencing (e.g., Ion Torrent of South San Francisco, Calif.), pyrosequencing (e.g., 454 of Branford, Conn.), sequencing by ligation (e.g., SOLiD sequencing owned by Life Technologies of Carlsbad, Calif.), sequencing by synthesis and reversible terminator (e.g., Illumina of San Diego, Calif.), nucleic acid imaging technologies such as transmission electron microscopy, and the like.

In general, next-generation sequencing methods typically use an in vitro cloning step to amplify individual DNA molecules. Emulsion PCR (emPCR) isolates individual DNA molecules along with primer-coated beads in aqueous droplets within an oil phase. PCR produces copies of the DNA molecule, which bind to primers on the bead, followed by immobilization for later sequencing. emPCR is used in the methods by Marguilis et al. (commercialized by 454 Life Sciences, Branford, Conn.), Shendure and Porreca et al. (also known as "polony sequencing") and SOLiD sequencing, (Applied Biosystems Inc., Foster City, Calif.). See M. Margulies, et al. (2005) "Genome sequencing in microfabricated high-density picolitre reactors" Nature 437: 376-380; J. Shendure, et al. (2005) "Accurate Multiplex Polony Sequencing of an Evolved Bacterial Genome" Science 309 (5741): 1728-1732. In vitro clonal amplification can also be carried out by "bridge PCR," where fragments are amplified upon primers attached to a solid surface. Braslavsky et al. developed a single-molecule method (commercialized by Helicos Biosciences Corp., Cambridge, Mass.) that omits this amplification step, directly fixing DNA molecules to a surface. I. Braslavsky, et al. (2003) "Sequence information can be obtained from single DNA molecules" Proceedings of the National Academy of Sciences of the United States of America 100: 3960-3964.

DNA molecules that are physically bound to a surface can be sequenced in parallel. In "sequencing by synthesis," a complementary strand is built based on the sequence of a template strand using a DNA polymerase. like dye-termination electrophoretic sequencing, Reversible terminator methods (commercialized by Illumina, Inc., San Diego, Calif. and Helicos Biosciences Corp., Cambridge, Mass.) use reversible versions of dye-terminators, adding one nucleotide at a time, and detect fluorescence at each position in real time, by repeated removal of the blocking group to allow polymerization of another nucleotide. "Pyrosequencing" also uses DNA polymerization, adding one nucleotide at a time and detecting and quantifying the number of nucleotides added to a given location through the light emitted by the release of attached pyrophosphates (commercialized by 454 Life Sciences, Branford, Conn.). See M. Ronaghi, et al. (1996). "Real-time DNA sequencing using detection of pyrophosphate release" Analytical Biochemistry 242: 84-89.

Specific examples of next-generation sequencing methods are described in further details below. One or more implementations of the current invention may use one or more of the following sequencing methods without deviating from the principles of the invention.

Single molecule real time sequencing (also known as SMRT) is a parallelized single molecule DNA sequencing by synthesis technology developed by Pacific Biosciences. Single molecule real time sequencing utilizes the zero-mode waveguide (ZMW). A single DNA polymerase enzyme is affixed at the bottom of a ZMW with a single molecule of DNA as a template. The ZMW is a structure that creates an illuminated observation volume that is small enough to observe only a single nucleotide of DNA (also known as a base) being incorporated by DNA polymerase. Each of the four DNA bases is attached to one of four different fluorescent dyes. When a nucleotide is incorporated by the DNA polymerase, the fluorescent tag is cleaved off and diffuses out of the observation area of the ZMW where its fluorescence is no longer observable. A detector detects the fluorescent signal of the nucleotide incorporation, and the base call is made according to the corresponding fluorescence of the dye.

Another single molecule sequencing technology applicable is the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

Ion Semiconductor Sequencing is a method of DNA sequencing based on the detection of hydrogen ions that are released during the polymerization of DNA. This is a method of "sequencing by synthesis," during which a complementary strand is built based on the sequence of a template strand. A microwell containing a template DNA strand to be sequenced is flooded with a single species of deoxyribonucleotide triphosphate (dNTP). If the introduced dNTP is complementary to the leading template nucleotide, it is incorporated into the growing complementary strand. This causes the release of a hydrogen ion that triggers an ISFET ion sensor, which indicates that a reaction has occurred. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. Ion semiconductor sequencing may also be referred to as ion torrent sequencing, pH-mediated sequencing, silicon sequencing, or semiconductor sequencing.

In pyrosequencing, the pyrophosphate ion released by the polymerization reaction is reacted with adenosine 5' phosphosulfate by ATP sulfurylase to produce ATP; the ATP then drives the conversion of luciferin to oxyluciferin plus light by luciferase. As the fluorescence is transient, no separate step to eliminate fluorescence is necessary in this method. One type of deoxyribonucleotide triphosphate (dNTP) is added at a time, and sequence information is discerned according to which dNTP generates significant signal at a reaction site. The commercially available Roche GS FLX instrument acquires sequence using this method. This technique and applications thereof are discussed in detail, for example, in Ronaghi et al., Analytical Biochemistry 242, 84-89 (1996) and Margulies et al., Nature 437, 376-380 (2005) (corrigendum at Nature 441, 120 (2006)). A commercially available pyrosequencing technology is 454 sequencing (Roche) (e.g. as described in Margulies, M. et al. Nature 437:376-380 [2005]).

In ligation sequencing, a ligase enzyme is used to join a partially double-stranded oligonucleotide with an overhang to the nucleic acid being sequenced, which has an overhang; in order for ligation to occur, the overhangs must be complementary. The bases in the overhang of the partially double-stranded oligonucleotide can be identified according to a fluorophore conjugated to the partially double-stranded oligonucleotide and/or to a secondary oligonucleotide that hybridizes to another part of the partially double-stranded oligonucleotide. After acquisition of fluorescence data, the ligated complex is cleaved upstream of the ligation site, such as by a type IIs restriction enzyme, for example, Bbvl, which cuts at a site a fixed distance from its recognition site (which was included in the partially double stranded oligonucleotide). This cleavage reaction exposes a new overhang just upstream of the previous overhang, and the process is repeated. This technique and applications thereof are discussed in detail, for example, in Brenner et al., Nature Biotechnology 18, 630-634 (2000). In some embodiments, ligation sequencing is adapted to the methods of the invention by obtaining a rolling circle amplification product of a circular nucleic acid molecule, and using the rolling circle amplification product as the template for ligation sequencing.

A commercially available example of ligation sequencing technology is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In reversible terminator sequencing, a fluorescent dye-labeled nucleotide analog that is a reversible chain terminator due to the presence of a blocking group is incorporated in a single-base extension reaction. The identity of the base is determined according to the fluorophore: in other words, each base is paired with a different fluorophore. After fluorescence/sequence data is acquired, the fluorophore and the blocking group are chemically removed, and the cycle is repeated to acquire the next base of sequence information. The Illumina GA instrument operates by this method. This technique and applications thereof are discussed in detail, for example, in Ruparel et al., Proceedings of the National Academy of Sciences of the United States of America 102, 5932-5937 (2005), and Harris et al., Science 320, 106-109 (2008).

A commercially available example of reversible terminator sequencing method is Illumina's sequencing-by-synthesis and reversible terminator-based sequencing (e.g. as described in Bentley et al., Nature 6:53-59 [2009]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp e.g. 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length e.g. 36 bp, are mapped to a known reference genome are counted.

In nanopore sequencing, a single stranded nucleic acid molecule is threaded through a pore, e.g., using an electrophoretic driving force, and sequence is deduced by analyzing data obtained as the single stranded nucleic acid molecule passes through the pore. The data can be ion current data, wherein each base alters the current, e.g., by partially blocking the current passing through the pore to a different, distinguishable degree.

In another illustrative, but non-limiting, embodiment, the methods described herein comprises obtaining sequence information using transmission electron microscopy (TEM). The method comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445.

In another illustrative, but non-limiting, embodiment, the methods described herein comprises obtaining sequence information using third-generation sequencing. In third-generation sequencing, a slide with an aluminum coating with many small (50 nm) holes is used as a zero mode waveguide (see, e.g., Levene et al., Science 299, 682-686 (2003)). The aluminum surface is protected from attachment of DNA polymerase by polyphosphonate chernistry, e.g, polyvinylphosphonate chemistry (see, e.g., Korlach et al., Proceedings of the National Academy of Sciences of the United States of America 105, 1176-1181 (2008)). This results in preferential attachment of the DNA polymerase molecules to the exposed silica in the holes of the aluminum coating. This setup allows evanescent wave phenomena to be used to reduce fluorescence background, allowing the use of higher concentrations of fluorescently labeled dNTPs. The fluorophore is attached to the terminal phosphate of the dNTPs, such that fluorescence is released upon incorporation of the dNTP, but the fluorophore does not remain attached to the newly incorporated nucleotide, meaning that the complex is immediately ready for another round of incorporation. By this method, incorporation of dNTPs into an individual primer-template complexes present in the holes of the aluminum coating can be detected. See, e.g., Eid et al., Science 323, 133-138 (2009).

VI. ASSAYING GENE AND PROTEIN VARIANTS

In some embodiments, polynucleotides generated in connection with methods of the present invention are optionally cloned into cells to express protein variants for activity screening (or used in in vitro transcription reactions to make products which are screened). Furthermore, the nucleic acids encoding protein variants can be enriched, sequenced, expressed, amplified in vitro or treated in any other common recombinant method.

General texts that describe molecular biological techniques useful herein, including cloning, mutagenesis, library construction, screening assays, cell culture and the like include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (2nd Ed.), Vol. 1-3, Cold Spring Harbor Laboratory, Cold Spring Harbor, N.Y., 1989 (Sambrook) and Current Protocols in Molecular Biology, F. M. Ausubel et al., eds., Current Protocols, a joint venture between Greene Publishing Associates, Inc. and John Wiley & Sons, Inc., New York (supplemented through 2000) (Ausubel). Methods of transducing cells, including plant and animal cells, with nucleic acids are generally available, as are methods of expressing proteins encoded by such nucleic acids. In addition to Berger, Ausubel and Sambrook, useful general references for culture of animal cells include Freshney (Culture of Animal Cells, a Manual of Basic Technique, third edition Wiley-Liss, New York (1994)) and the references cited therein, Humason (Animal Tissue Techniques, fourth edition W.H. Freeman and Company (1979)) and Ricciardelli, et al., In Vitro Cell Dev. Biol. 25:1016-1024 (1989). References for plant cell cloning, culture and regeneration include Payne et al. (1992) Plant Cell and Tissue Culture in Liquid Systems John Wiley & Sons, Inc. New York, N.Y. (Payne); and Gamborg and Phillips (eds) (1995) Plant Cell, Tissue and Organ Culture; Fundamental Methods Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS).

Examples of techniques sufficient to direct persons of skill through in vitro amplification methods, useful e.g., for amplifying oligonucleotide recombined nucleic acids including polymerase chain reactions (PCR), ligase chain reactions (LCR), Qβ-replicase amplifications and other RNA polymerase mediated techniques (e.g., NASBA). These techniques are found in Berger, Sambrook, and Ausubel, supra, as well as in Mullis et al., (1987) U.S. Pat. No. 4,683,202; PCR Protocols A Guide to Methods and Applications (Innis et al. eds) Academic Press Inc. San Diego, Calif. (1990) (Innis); Amheim & Levinson (Oct. 1, 1990) C&EN 36-47; The Journal Of NIH Research (1991) 3, 81-94; Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem 35, 1826; Landegren et al., (1988) Science 241, 1077-1080; Van Brunt (1990) Biotechnology 8, 291-294; Wu and Wallace, (1989) Gene 4, 560; Barringer et al. (1990) Gene 89, 117, and Sooknanan and Malek (1995) Biotechnology 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

In one preferred method, reassembled sequences are checked for incorporation of family-based recombination oligonucleotides. This can be done by cloning and sequencing the nucleic acids, and/or by restriction digestion, e.g., as essentially taught in Sambrook, Berger and Ausubel, supra. In addition, sequences can be PCR amplified and sequenced directly. Thus, in addition to, e.g., Sambrook, Berger, Ausubel and Innis (supra), additional PCR sequencing methodologies are also particularly useful. For example, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8):1611-1617). In the methods, four PCR reactions on a template are performed, in each of which one of the nucleotide triphosphates in the PCR reaction mixture is partially substituted with a 2' deoxynucleoside 5'-[P-borano]-triphosphate. The boronated nucleotide is stochastically incorporated into PCR products at varying positions along the PCR amplicon in a nested set of PCR fragments of the template. An exonuclease that is blocked by incorporated boronated nucleotides is used to cleave the PCR amplicons. The cleaved amplicons are then separated by size using polyacrylamide gel electrophoresis, providing the sequence of the amplicon. An advantage of this method is that it uses fewer biochemical manipulations than performing standard Sanger-style sequencing of PCR amplicons.

Synthetic genes are amenable to conventional cloning and expression approaches; thus, properties of the genes and proteins they encode can readily be examined after their expression in a host cell. Synthetic genes can also be used to generate polypeptide products by in vitro (cell-free) transcription and translation. Polynucleotides and polypeptides can thus be examined for their ability to bind a variety of predetermined ligands, small molecules and ions, or polymeric and heteropolymeric substances, including other proteins and polypeptide epitopes, as well as microbial cell walls, viral particles, surfaces and membranes.

For example, many physical methods can be used for detecting polynucleotides encoding phenotypes associated with catalysis of chemical reactions by either polynucleotides directly, or by encoded polypeptides. Solely for the purpose of illustration, and depending on the specifics of particular pre-determined chemical reactions of interest, these methods may include a multitude of techniques known in the art which account for a physical difference between substrate(s) and product(s), or for changes in the reaction media associated with chemical reaction (e.g. changes in electromagnetic emissions, adsorption, dissipation, and fluorescence, whether UV, visible or infrared (heat)). These methods also can be selected from any combination of the following: mass-spectrometry; nuclear magnetic resonance; isotopically labeled materials, partitioning and spectral methods accounting for isotope distribution or labeled product formation; spectral and chemical methods to detect accompanying changes in ion or elemental compositions of reaction product(s) (including changes in pH, inorganic and organic ions and the like). Other methods of physical assays, suitable for use in the methods herein, can be based on the use of biosensors specific for reaction product(s), including those comprising antibodies with reporter properties, or those based on in vivo affinity recognition coupled with expression and activity of a reporter gene. Enzyme-coupled assays for reaction product detection and cell life-death-growth selections in vivo can also be used where appropriate. Regardless of the specific nature of the physical assays, they all are used to select a desired activity, or combination of desired activities, provided or encoded by a biomolecule of interest.

The specific assay used for the selection will depend on the application. Many assays for proteins, receptors, ligands, enzymes, substrates and the like are known. Formats include binding to immobilized components, cell or organismal viability, production of reporter compositions, and the like.

High throughput assays are particularly suitable for screening libraries employed in the present invention. In high throughput assays, it is possible to screen up to several thousand different variants in a single day. For example, each well of a microtiter plate can be used to run a separate assay, or, if concentration or incubation time effects are to be observed, every 5-10 wells can test a single variant (e.g., at different concentrations). Thus, a single standard microtiter plate can assay about 100 (e.g., 96) reactions. If 1536 well plates are used, then a single plate can easily assay from about 100 to about 1500 different reactions. It is possible to assay several different plates per day; assay screens for up to about 6,000-20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.) which can provide very high throughput microfluidic assay methods.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay.

These configurable systems provide high throughput and rapid start up as well as a high degree of flexibility and customization.

The manufacturers of such systems provide detailed protocols for various high throughput screening assays. Thus, for example, Zymark Corp. provides technical bulletins describing screening systems for detecting the modulation of gene transcription, ligand binding, and the like.

A variety of commercially available peripheral equipment and software is available for digitizing, storing and analyzing a digitized video or digitized optical or other assay images, e.g., using PC (Intel x86 or pentium chip-compatible MAC OS, WINDOWS™ family, or UNIX based (e.g., SUN™ work station) computers.

Systems for analysis typically include a digital computer specifically programmed to perform specialized algorithms using software for directing one or more steps of one or more of the methods herein, and, optionally, also include, e.g., a next generation sequencing platform control software, high-throughput liquid control software, image analysis software, data interpretation software, a robotic liquid control armature for transferring solutions from a source to a destination operably linked to the digital computer, an input device (e.g., a computer keyboard) for entering data to the digital computer to control operations or high throughput liquid transfer by the robotic liquid control armature and, optionally, an image scanner for digitizing label signals from labeled assay components. The image scanner can interface with image analysis software to provide a measurement of probe label intensity. Typically, the probe label intensity measurement is interpreted by the data interpretation software to show whether the labeled probe hybridizes to the DNA on the solid support.

In some embodiments, cells, viral plaques, spores or the like, comprising in vitro oligonucleotide-mediated recombination products or physical embodiments of in silico recombined nucleic acids, can be separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each parameter can be controlled and optimized.

The uniform process of automated colony picking such as the Q-bot decreases human handling error and increases the rate of establishing cultures (roughly 10,000/4 hours). These cultures are optionally shaken in a temperature and humidity controlled incubator. Optional glass balls in the microtiter plates act to promote uniform aeration of cells and the dispersal of cellular (e.g., mycelial) fragments similar to the blades of a fermentor. Clones from cultures of interest can be isolated by limiting dilution. As also described supra, plaques or cells constituting libraries can also be screened directly for the production of proteins, either by detecting hybridization, protein activity, protein binding to antibodies, or the like. To increase the chances of identifying a pool of sufficient size, a prescreen that increases the number of mutants processed by 10-fold can be used. The goal of the primary screen is to quickly identify mutants having equal or better product titers than the parent strain(s) and to move only these mutants forward to liquid cell culture for subsequent analysis.

One approach to screening diverse libraries is to use a massively parallel solid-phase procedure to screen cells expressing polynucleotide variants, e.g., polynucleotides that encode enzyme variants. Massively parallel solid-phase screening apparatus using absorption, fluorescence, or FRET are available. See, e.g., U.S. Pat. No. 5,914,245 to Bylina, et al. (1999); see also, http://wwwl.lkairos-scientific.com/; Youvan et al. (1999) "Fluorescence Imaging Micro-Spectrophotometer (FIMS)" Biotechnology et alia, <wwwl.let-al.com>1:1-16; Yang et al. (1998) "High Resolution Imaging Microscope (HIRIM)" Biotechnology et alia, <www.et-al.com>4:1-20; and Youvan et al. (1999) "Calibration of Fluorescence Resonance Energy Transfer in Microscopy Using Genetically Engineered GFP Derivatives on Nickel Chelating Beads" posted at wwwl.lkairos-scientific.com. Following screening by these techniques, molecules of interest are typically isolated, and optionally sequenced using methods that are known in the art. The sequence information is then used as set forth herein to design a new protein variant library.

Similarly, a number of well-known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual synthetic operations performed by a scientist. Any of the above devices are suitable for use with the present invention, e.g., for high-throughput screening of molecules encoded by nucleic acids evolved as described herein. The nature and implementation of modifications to these devices (if any) so that they can operate as discussed herein will be apparent to persons skilled in the relevant art.

VII. DIGITAL APPARATUS AND SYSTEMS

As should be apparent, embodiments described herein employ processes acting under control of instructions and/or data stored in or transferred through one or more computer systems. Embodiments disclosed herein also relate to systems and apparatus (e.g., equipment) for performing these operations. In some embodiments, the apparatus is specially designed and/or constructed for the required purposes, or it may be a general-purpose computer selectively activated or reconfigured by a computer program and/or data structure stored in the computer. The processes provided by the present disclosure are not inherently related to any particular computer or other specific apparatus. In particular, various general-purpose machines find use with programs written in accordance with the teachings herein. However, in some embodiments, a specialized apparatus is constructed to perform the required method operations. One embodiment of a particular structure for a variety of these machines is described below.

In addition, certain embodiments of the present disclosure relate to computer-readable media or computer program products that include program instructions and/or data (including data structures) for performing various computer-implemented operations. Examples of computer-readable media include, but are not limited to, magnetic media such as hard disks; optical media such as CD-ROM devices and holographic devices; magneto-optical media; and semiconductor memory devices, such as flash memory. Hardware devices such as read-only memory devices (ROM) and random access memory devices (RAM) may be configured to store program instructions. Hardware devices such as application-specific integrated circuits (ASICs) and programmable logic devices (PLDs) may be configured to execute and store program instructions. It is not intended that the present disclosure be limited to any particular computer-readable media or any other computer program products that include instructions and/or data for performing computer-implemented operations.

Examples of program instructions include, but are not limited to low-level code such as produced by a compiler, and files containing higher level code that may be executed by the computer using an interpreter. Further, the program instructions include, but are not limited to machine code, source code and any other code that directly or indirectly controls operation of a computing machine in accordance with the present disclosure. The code may specify input, output, calculations, conditionals, branches, iterative loops, etc.

Figure 4:
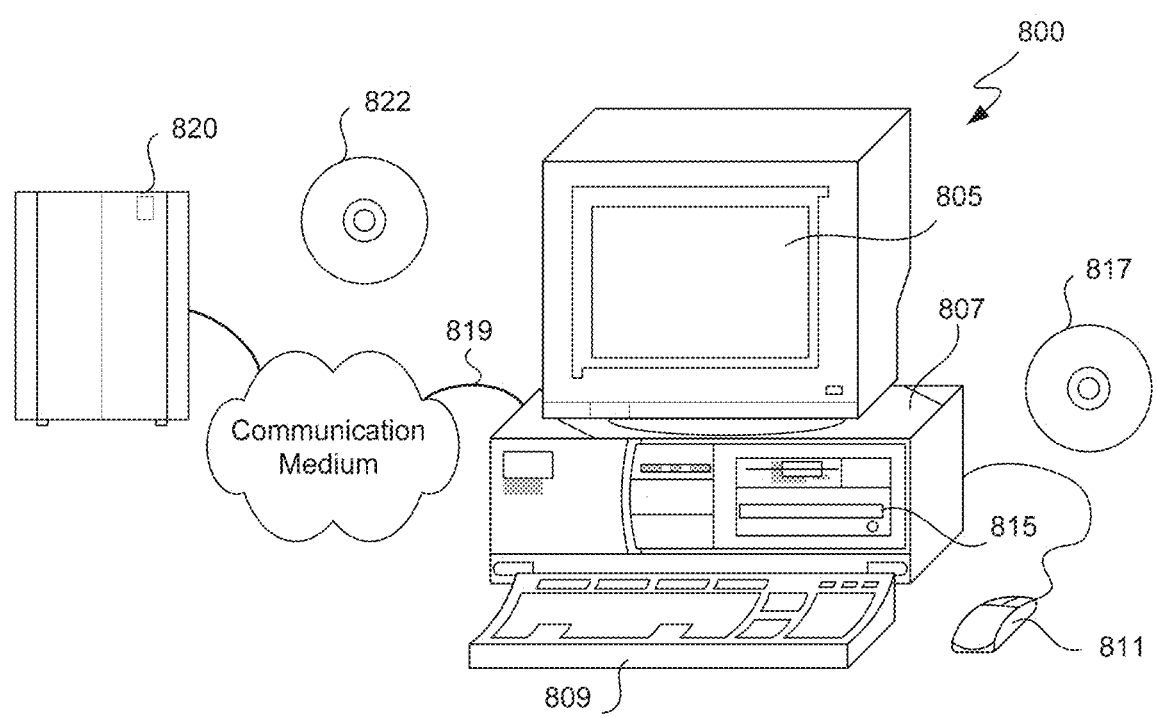
FIG. 4 shows an exemplary digital device that can be implemented according to some embodiments of the current disclosure.

In one illustrative example, code embodying methods disclosed herein are embodied in a fixed media or transmissible program component containing logic instructions and/or data that when loaded into an appropriately configured computing device causes the device to perform virtual screening of one or more biomolecule variants interacting with one or more ligands. FIG. 4 shows an example digital device 800 that is a logical apparatus that can read instructions from media 817, network port 819, user input keyboard 809, user input 811, or other inputting means. Apparatus 800 can thereafter use those instructions to direct statistical operations in data space, e.g., to evaluate a geometric relation between a ligand moiety and one or more features of an active site, cofactor, etc. (e.g., to determine a distance between the position of a native substrate in an active site and the position of a substrate under consideration in the active site of a protein variant). One type of logical apparatus that can embody disclosed embodiments is a computer system as in computer system 800 comprising CPU 807, optional user input devices keyboard 809, and GUI pointing device 811, as well as peripheral components such as disk drives 815 and monitor 805 (which displays GO modified character strings and provides for simplified selection of subsets of such character strings by a user. Fixed media 817 is optionally used to program the overall system and can include, e.g., a disk-type optical or magnetic media or other electronic memory storage element. Communication port 819 can be used to program the system and can represent any type of communication connection.

Certain embodiments can also be embodied within the circuitry of an application specific integrated circuit (ASIC) or programmable logic device (PLD). In such a case, the embodiments are implemented in a computer readable descriptor language that can be used to create an ASIC or PLD. Some embodiments of the present disclosure are implemented within the circuitry or logic processors of a variety of other digital apparatus, such as PDAs, laptop computer systems, displays, image editing equipment, etc.

In some embodiments, the present disclosure relates to a computer program product comprising one or more computer-readable storage media having stored thereon computer-executable instructions that, when executed by one or more processors of a computer system, cause the computer system to implement a method for virtual screening of protein variants and/or in silico directed evolution of proteins having desired activity. Such a method may be any method described herein such as those encompassed by the figures and pseudocode. In some embodiments, for example, the method receives sequence data for a plurality of enzymes, creates three-dimensional homology models of biological molecules, dock the homology models of enzymes with one or more computational representations of substrates, and select enzymes having desired catalytic activity and selectivity. In some embodiments, the method can further develop variant libraries from variants that have been highly ranked by the screening process. The variant libraries can be used in re-iterative directed evolution and screening, which can result in enzymes of desired beneficial properties.

In some embodiments, the docking of the homology models of enzymes with one or more computational representations of substrates is conducted by a docking program on a computer system that uses a computational representation of a ligand and computational representations of the active sites of a plurality of variants as described herein. In various embodiments, methods for determining docking involve evaluating the binding energy between a pose of the substrate and the enzyme. For a protein variant that successfully docks with the ligand, the virtual protein screening system considers a plurality of poses of the computational representation of the ligand in the active site of the protein variant under consideration, and determines which if any of the plurality of poses is active. In various embodiments, methods for determining active poses involve evaluating the geographical constraints defining a range of relative positions of one or more atoms in the ligand and one or more atoms in the protein and/or cofactor associated with the protein.

VIII. EMBODIMENTS IN WEBSITES AND CLOUD COMPUTING

The Internet includes computers, information appliances, and computer networks that are interconnected through communication links. The interconnected computers exchange information using various services, such as electronic mail, ftp, the World Wide Web ("WWW") and other services, including secure services. The WWW service can be understood as allowing a server computer system (e.g., a Web server or a Web site) to send web pages of information to a remote client information appliance or computer system. The remote client computer system can then display the web pages. Generally, each resource (e.g., computer or web page) of the WWW is uniquely identifiable by a Uniform Resource Locator ("URL"). To view or interact with a specific web page, a client computer system specifies a URL for that web page in a request. The request is forwarded to a server that supports that web page. When the server receives the request, it sends that web page to the client information system. When the client computer system receives that web page, it can display the web page using a browser or can interact with the web page or interface as otherwise provided. A browser is a logic module that effects the requesting of web pages and displaying or interacting with web pages.

Currently, displayable web pages are typically defined using a Hyper Text Markup Language ("HTML"). HTML provides a standard set of tags that define how a web page is to be displayed. An HTML document contains various tags that control the displaying of text, graphics, controls, and other features. The HTML document may contain URLs of other Web pages available on that server computer system or other server computer systems. URLs can also indicate other types of interfaces, including such things as CGI scripts or executable interfaces, that information appliances use to communicate with remote information appliances or servers without necessarily displaying information to a user.

The Internet is especially conducive to providing information services to one or more remote customers. Services can include items (e.g., music or stock quotes) that are delivered electronically to a purchaser over the Internet. Services can also include handling orders for items (e.g., groceries, books, or chemical or biologic compounds, etc.) that may be delivered through conventional distribution channels (e.g., a common carrier). Services may also include handling orders for items, such as airline or theater reservations, that a purchaser accesses at a later time. A server computer system may provide an electronic version of an interface that lists items or services that are available. A user or a potential purchaser may access the interface using a browser and select various items of interest. When the user has completed selecting the items desired, the server computer system may then prompt the user for information needed to complete the service. This transaction-specific order information may include the purchaser's name or other identification, an identification for payment (such as a corporate purchase order number or account number), or additional information needed to complete the service, such as flight information.

Among services of particular interest that can be provided over the internet and over other networks are biological data and biological databases. Such services include a variety of services provided by the National Center for Biotechnology Information (NCBI) of the National Institutes of Health (NIH). NCBI is charged with creating automated systems for storing and analyzing knowledge about molecular biology, biochemistry, and genetics; facilitating the use of such databases and software by the research and medical community; coordinating efforts to gather biotechnology information both nationally and internationally; and performing research into advanced methods of computer-based information processing for analyzing the structure and function of biologically important molecules.

NCBI holds responsibility for the GenBank® DNA sequence database. The database has been constructed from sequences submitted by individual laboratories and by data exchange with the international nucleotide sequence databases, the European Molecular Biology Laboratory (EMBL) and the DNA Database of Japan (DDBJ), and includes patent sequence data submitted to the U.S. Patent and Trademark Office. In addition to GenBank®, NCBI supports and distributes a variety of databases for the medical and scientific communities. These include the Online Mendelian Inheritance in Man (OMIM), the Molecular Modeling Database (MMDB) of 3D protein structures, the Unique Human Gene Sequence Collection (UniGene), a Gene Map of the Human Genome, the Taxonomy Browser, and the Cancer Genome Anatomy Project (CGAP), in collaboration with the National Cancer Institute. Entrez is NCBI's search and retrieval system that provides users with integrated access to sequence, mapping, taxonomy, and structural data. Entrez also provides graphical views of sequences and chromosome maps. A feature of Entrez is the ability to retrieve related sequences, structures, and references. BLAST, as described herein, is a program for sequence similarity searching developed at NCBI for identifying genes and genetic features that can execute sequence searches against the entire DNA database. Additional software tools provided by NCBI include: Open Reading Frame Finder (ORF Finder), Electronic PCR, and the sequence submission tools, Sequin and BankIt. NCBI's various databases and software tools are available from the WWW or by FTP or by e-mail servers. Further information is available at wwwl.lncbi.nlm.nih.gov.

Some biological data available over the internet is data that is generally viewed with a special browser "plug-in" or other executable code. One example of such a system is CHIME, a browser plug-in that allows an interactive virtual 3-dimensional display of molecular structures, including biological molecular structures. Further information regarding CHIME is available at wwwl.lmdlchime.com/chime/.

A variety of companies and institutions provide online systems for ordering biological compounds. Examples of such systems can be found at wwwl.lgenosys.com/oligo-_custinfo.cfm or wwwl.lgenomictechnologies.com/Qbrowser2_FP.html. Typically, these systems accept any descriptor of a desired biological compound (such as an oligonucleotide, DNA strand, RNA strand, amino acid sequence, etc.) and then the requested compound is manufactured and is shipped to the customer in a liquid solution or other appropriate form.

As the methods provides herein may be implemented on a website as further described below, the computational results or physical results involving polypeptides or polynucleotides produced by some embodiments of the disclosure may be provided through the internet in ways similar to the biological information and compounds described above.

To further illustrate, the methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an Intranet or an Internet.

In one internet embodiment, a client system typically executes a Web browser and is coupled to a server computer executing a Web server. The Web browser is typically a program such as IBM's Web Explorer, Microsoft's Internet explorer, NetScape, Opera, or Mosaic. The Web server is typically, but not necessarily, a program such as IBM's HTTP Daemon or other www daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention.

As mentioned, a user of a client connected to the Intranet or Internet may cause the client to request resources that are part of the web site(s) hosting the application(s) providing an implementation of the methods of this invention. Server program(s) then process the request to return the specified resources (assuming they are currently available). The standard naming convention (i.e., Uniform Resource Locator ("URL")) encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

The software implementing the method(s) of this invention can run locally on the server hosting the website in a true client-server architecture. Thus, the client computer posts requests to the host server which runs the requested process(es) locally and then downloads the results back to the client. Alternatively, the methods of this invention can be implemented in a "multi-tier" format in which a component of the method(s) are performed locally by the client. This can be implemented by software downloaded from the server on request by the client (e.g. a Java application) or it can be implemented by software "permanently" installed on the client.

In one embodiment the application(s) implementing the methods of this invention are divided into frames. In this paradigm, it is helpful to view an application not so much as a collection of features or functionality but, instead, as a collection of discrete frames or views. A typical application, for instance, generally includes a set of menu items, each of with invokes a particular frame—that is, a form which manifest certain functionality of the application. With this perspective, an application is viewed not as a monolithic body of code but as a collection of applets, or bundles of functionality. In this manner from within a browser, a user would select a Web page link which would, in turn, invoke a particular frame of the application (i.e., a sub-application). Thus, for example, one or more frames may provide functionality for inputting and/or encoding biological molecule(s) into one or more data spaces, while another frame provides tools for refining a model of the data space.

In certain embodiments, the methods of this invention are implemented as one or more frames providing, e.g., the following functionalit(ies): function(s) to encode two or more biological molecules into character strings to provide a collection of two or more different initial character strings wherein each of said biological molecules comprises a selected set of subunits; functions to select at least two substrings from the character strings; functions to concatenate the substrings to form one or more product strings about the same length as one or more of the initial character strings; functions to add (place) the product strings to a collection of strings; functions to create and manipulate computational representation/models of enzymes and substrates, functions to dock a computational representation of a substrate (e.g., a ligand) with the computational representation of an enzyme (e.g., a protein); functions to apply molecular dynamics to molecular models; functions to calculate various constraints between molecules that affect chemical reactions involving the molecules (e.g., distance or angle between a substrate moiety and an enzyme active site); and functions to implement any feature set forth herein.

One or more of these functionalities may also be implemented exclusively on a server or on a client computer. These functions, e.g., functions for creating or manipulating computational models of biological molecules, can provide one or more windows wherein the user can insert or manipulate representation(s) of biological molecules. In addition, the functions also, optionally, provides access to private and/or public databases accessible through a local network and/or the intranet whereby one or more sequences contained in the databases can be input into the methods of this invention. Thus, for example, in one embodiment, the user can, optionally, have the ability to request a search of GenBank® and input one or more of the sequences returned by such a search into an encoding and/or a diversity generating function.

Methods of implementing Intranet and/or Intranet embodiments of computational and/or data access processes are well known to those of skill in the art and are documented in great detail (see, e.g., Cluer et al. (1992) "A General Framework for the Optimization of Object-Oriented Queries," Proc SIGMOD International Conference on Management of Data, San Diego, Calif., Jun. 2-5, 1992, SIGMOD Record, vol. 21, Issue 2, June, 1992; Stonebraker, M., Editor; ACM Press, pp. 383-392; ISO-ANSI, Working Draft, "Information Technology-Database Language SQL," Jim Melton, Editor, International Organization for Standardization and American National Standards Institute, July 1992; Microsoft Corporation, "ODBC 2.0 Programmer's Reference and SDK Guide. The Microsoft Open Database Standard for Microsoft Windows™ and Windows NT™, Microsoft Open Database Connectivity™ Software Development Kit," 1992, 1993, 1994 Microsoft Press, pp. 3-30 and 41-56; ISO Working Draft, "Database Language SQL-Part 2:Foundation (SQL/Foundation)," CD9075-2:199.chi.SQL, Sep. 11, 1997, and the like). Additional relevant details regarding web-based applications are found in WO 00/42559, entitled "METHODS OF POPULATING DATA STRUCTURES FOR USE IN EVOLUTIONARY SIMULATIONS," by Selifonov and Stemmer.

In some embodiments, the methods for exploring, screening, and/or developing polynucleotide or polypeptide sequences can be implemented as a multi-user system on a computer system with a plurality of processing units and memories distributed over a computer network, wherein the network may include intranet on LAN and/or the Internet. In some embodiments, the distributed computing architecture involves a "cloud," which is a collection of computer systems available over a computer network for computation and data storage. The computing environment involving a cloud is referred to as a cloud computing environment. In some embodiments, one or more users can access the computers of the cloud distributed over an intranet and/or the Internet. In some embodiments, a user may remotely access, through a web client, server computers that implement the methods for screening and/or developing protein variants described above.

In some embodiments involving a cloud computing environment, virtual machines (VMs) are provisioned on the server computers, and the results of the virtual machines can be sent back to the user. A virtual machine (VM) is a software-based emulation of a computer. Virtual machines may be based on specifications of a hypothetical computer or emulate the computer architecture and functions of a real world computer. The structure and functions of VMs are well known in the art. Typically, a VM is installed on a host platform that includes system hardware, and the VM itself includes virtual system hardware and guest software.

The host system hardware for a VM includes one or more Central Processing Units (CPUs), memory, one or more hard disks and various other devices. The VM's virtual system hardware includes one or more virtual CPUs, virtual memory, one or more virtual hard disks and one or more virtual devices. The VM's guest software includes guest system software and guest applications. In some implementations, guest system software includes a guest operating system with drivers for virtual devices. In some implementations, the VM's guest applications include at least one instance of a virtual protein screening system as described above.

In some embodiments, the number of provisioned VMs can be scaled to the computational load of the problem to be solved. In some embodiments, a user can request a virtual machine from a cloud, the VM including a virtual screening system. In some embodiments, the cloud computing environment can provision a VM based on the user request. In some embodiments a VM may exist in a previously stored VM image, which can be stored in an image repository. The cloud computing environment can search and transfer the image to a server or a user system. The cloud computing environment can then boot the image on the server or user system.

IX. EXAMPLES

Example 1

The following example illustrates a process of virtually screening enzyme variants and developing enzymes of desired catalytic activity and selectivity implementing various embodiments.

In summary, the process involved creating 3-dimensional homology models of an actual panel of enzymes and virtually screening the members of the enzyme panel to select a first variant that (a) docked with the substrate in an active pose, (b) docked in a pro-S conformation, and (c) had the lowest total binding energy (or docking score) among those that docked in active poses and in a pro-S conformation. The process then used the first variant as a round-1 backbone, or parental sequence, to create a round-1 virtual variant library using virtual mutagenesis techniques for virtual directed evolution. Then, the process created models of members of the round-1 virtual variant library, screened the round-1 virtual variant library, and selected a second variant as a round-2 backbone using similar selection methods as in selecting the round-1 backbone. The process also selected additional variants from the round-1 virtual variant library. The additional variants (a) docked with the substrate in active poses, and (b) had low total binding energy (or docking score) among those that dock in active poses. The process then recombined the round-2 backbone with the additional variants to introduce diversity into a round-2 variant library. Finally, the process computationally modeled, screened and selected variants, yielding virtual enzyme variants with improved activity and selectivity compared to the round-1 and round-2 backbones.

More specifically, the example process started by creating 194 homology models of an actual panel of enzymes. These enzymes catalyze a native substrate that is structurally or functionally related to a desired substrate. The process docked the desired substrate to the homology models, and virtually screened members of the actual enzyme panel to find only one variant that (a) docked with the desired substrate in an active pose, and (b) docked in a pro-S conformation. Successful binding in an active pose suggested that the ligand was likely to undergo a catalytic transformation or perform some desired role such as covalently binding with the binding site. The docking of the desired substrate and the panel members was performed by docking methods described in details above. The functionally relevant moieties of the desired substrate were compared to the native substrate by placing the two substrates in the same X, Y, Z coordinates in a docking space. Whether a pose of the desired substrate was active, pro-S, or pro-R, was determined by the distance between the moieties of the desired substrate and the native substrate. The distance criterion was set at 1.25 Å for this example. The criterion value and rules (requiring the mean, min, max, etc. of the distances to be smaller than the criterion) may be adjusted in different applications and at various rounds of directed evolution.

It was found that this variant could bind the substrate in both pro-S and pro-R conformations. It was suspected that the variant might not be very selective. To derive an active and S selective enzyme for the desired substrate, this variant was selected as a round-1 backbone to create a round-1 variant library by mutagenesis in the first round of directed evolution in silico. There were 15 active site positions identified in this round-1 backbone, and 19 amino acids possible for each position that would be different from the round-1 backbone variant, amounting to 285 different possible point mutations. In round-1 evolution, 1000 mutants were generated for the round-1 variant library, each mutant having a random number of mutations, wherein the random number was selected from a Gaussian distribution of mean=4 and SD=2. The mutations were randomly chosen from the 285 possible point mutations.

Then, the process used docking and screening methods similar to those described above for the actual enzyme panel, with the exception that the criterion for determining activity and selectivity of poses was set at a more stringent value of 1 Å as opposed to 1.25 Å. The process identified one variant as comprising the mutation having the lowest total binding energy among all mutants that would bind in active and pro-S poses. In fact, the mutation in this variant prevented the substrate from binding in an undesired pro-R conformation, representing a beneficial mutation for selectivity. The process thus selected this variant as the backbone for a round-2 directed evolution.

However, the binding energy of the round-2 backbone at 0.38303 kcal/mol was relatively high even compared to that determined for the round-1 backbone (−4.005 kcal/mol), suggesting that evolution could further improve the beneficial properties of the enzyme. A round-2 directed evolution was carried out in silico by introducing 29 mutations into the round-2 backbone. The 29 mutations were derived from 29 variants of the round-1 library having the lowest binding energy among all variants obtained from the round-1 evolution. In round-2 evolution, 1000 mutants were generated to produce the round-2 variant library, each mutant having a random number of mutations, wherein the random number was selected from a Gaussian distribution of mean=6 and SD=4. The mutations were randomly chosen from the 29 possible mutations derived from 29 variants.

Figure 5:
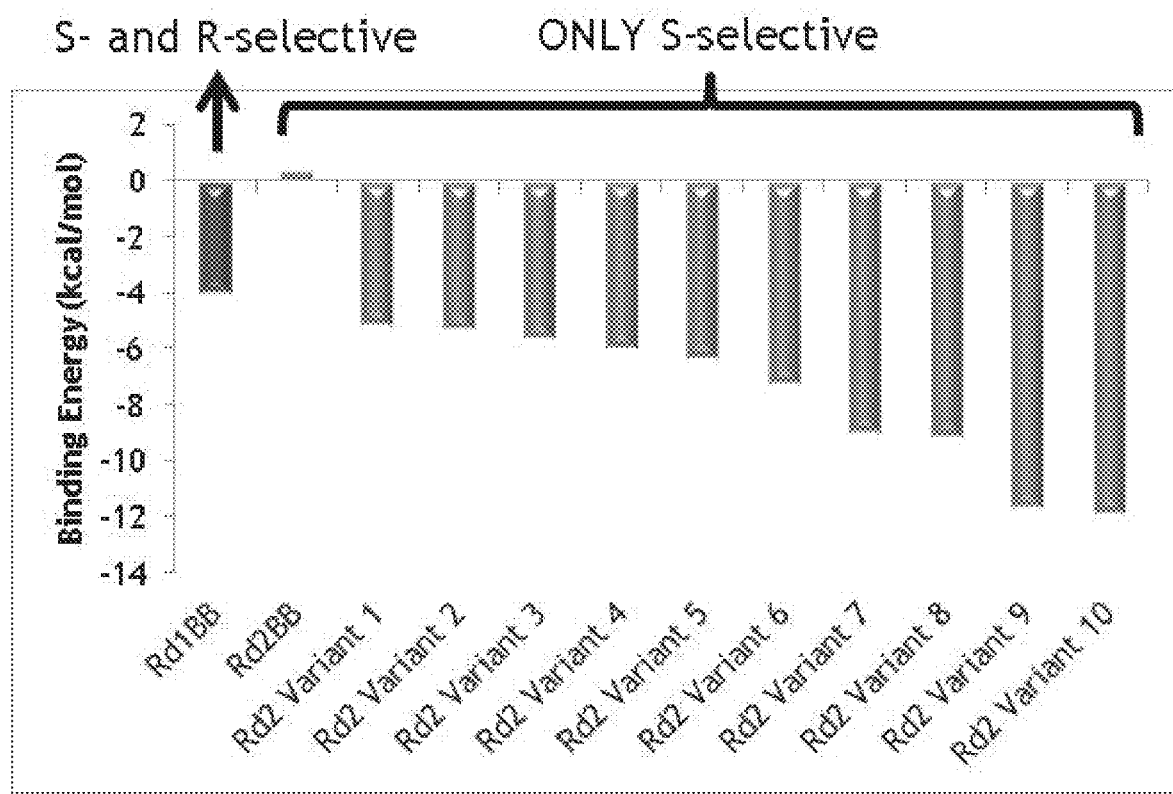
FIG. 5 provides a plot of data showing the binding energy and selectivity of 10 best variants from a second round of directed evolution and the backbones for round 1 (Rd1BB) and round 2 (Rd2BB).

Then, the process used docking and screening methods similar to those described above to determine that most variants favored binding the substrate in a desired pro-S conformation only, and at least 10 variants had better binding energy than round 1 and round-2 backbones. See Table 1 for the binding energies of the improved variants from round-2 evolution and the round-1 and round-2 backbones. In addition to showing the data of Table 1, FIG. 5 shows the selectivity of the 10 improved variants from round-2 evolution, as well as the round-1 and round-2 backbones. The Figure illustrates that virtual screening of enzyme panel first identified the round-1 backbone that had a low binding energy, but was not S-selective. The process then improved S-selectivity using in silico directed evolution (mutagenesis), to obtain the round-2 backbone. The process finally improved substrate binding in round-2 evolution through recombination, yielding enzyme variants that had high affinity with the desired substrate and were enantioselective.

TABLE 1

Binding Energies of Variants from Round-2 Evolution

| Variants | Binding Energy (kcal/mol) |
|---|---|
| Rd2 Variant 10 | −11.9 |
| Rd2 Variant 9 | −11.7 |
| Rd2 Variant 8 | −9.2 |
| Rd2 Variant 7 | −9.0 |
| Rd2 Variant 6 | −7.3 |
| Rd2 Variant 5 | −6.4 |
| Rd2 Variant 4 | −6.0 |
| Rd2 Variant 3 | −5.7 |
| Rd2 Variant 2 | −5.3 |
| Rd2 Variant 1 | −5.2 |
| Rd2BB | 0.4 |
| Rd1BB | −4.0 |

Figure 6A:
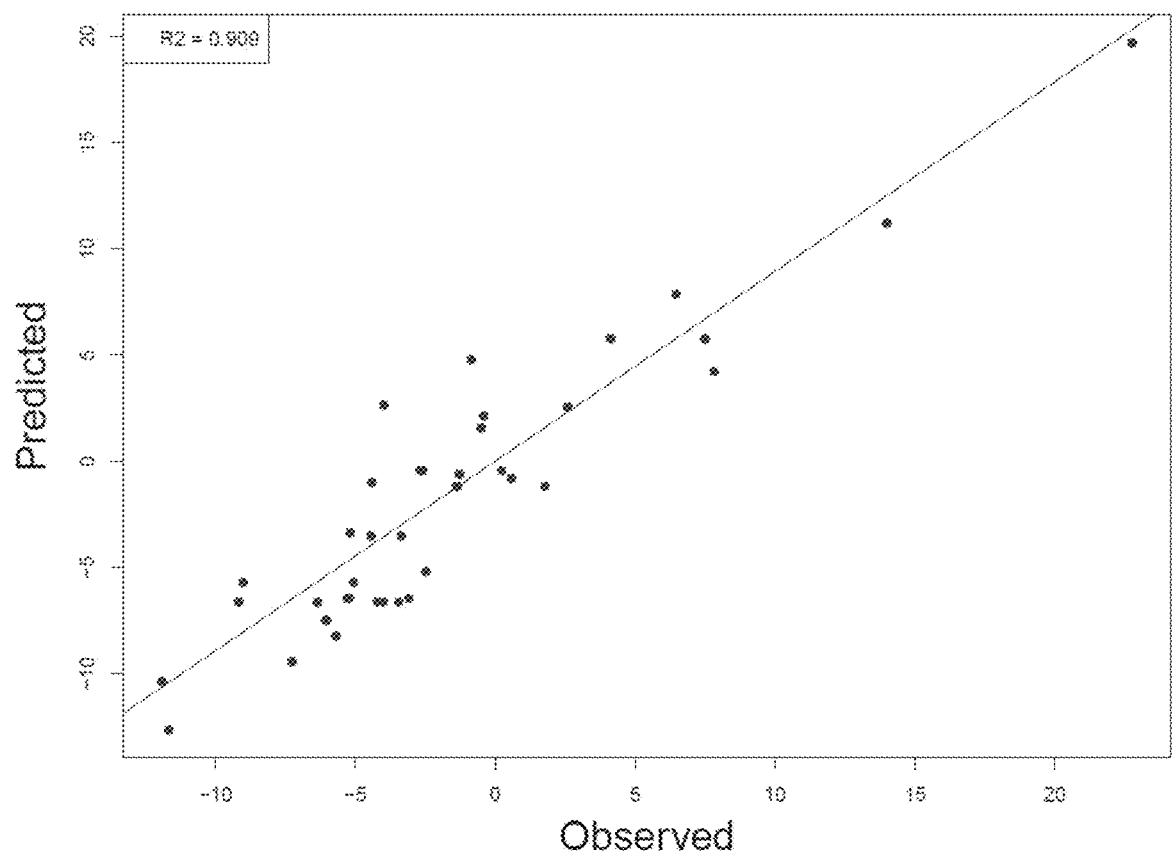
FIG. 6A shows model fitness of a sequence activity model built using data from a virtual protein screening system according to some embodiments.
Figure 6B:
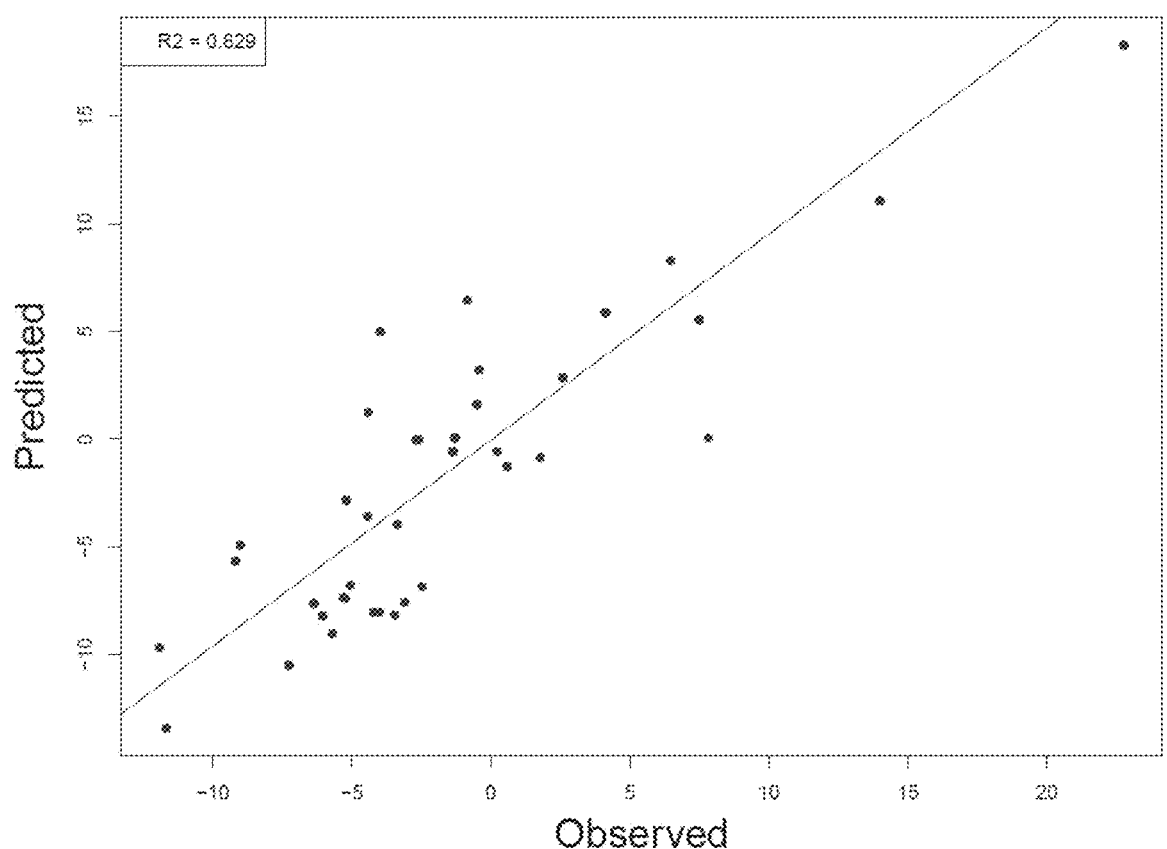
FIG. 6B shows cross validation data indicating that the sequence activity model as constructed in FIG. 6A was accurate in predicting binding energy.

The diversity provided in the two rounds of evolution was generated by mutagenesis and recombination, inspired by biological genetic operations. In some applications, the virtual protein screening method may be combined with sequence-activity models that guide directed evolution methods. A sequence activity model was built with multiple linear regression techniques according to methods described in U.S. Pat. No. 7,783,428. In FIG. 6A, the sequence activity model's predicted binding energy are plotted against the observed energy obtained by the virtual screening system for a test set of sequences. Cross validation of the sequence activity model was performed by testing a validation set of sequences left out from the test set. The model accounts for 90.9% of the variance in the test set ($R^2$=0.909). Cross validation data in FIG. 6B show that the sequence activity model was accurate in predicting binding energy from the sequences of particular mutations at particular positions, accounting for 82.9% of the variance in the validation set ($R^2$=.829).

Figure 6C:
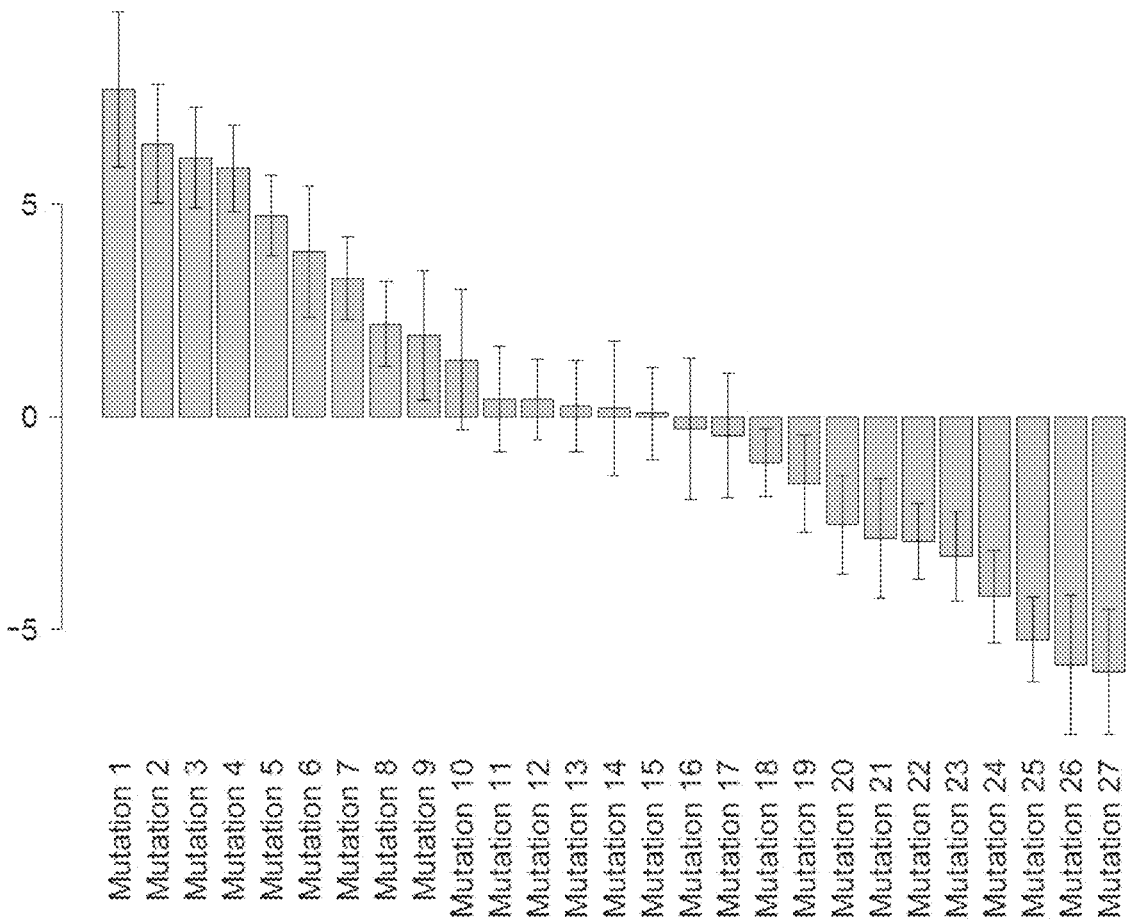
FIG. 6C shows the coefficients for various mutations according to the sequence activity model as constructed in FIG. 6A.

The model may be used to identify amino acids for mutagenesis. Among other ways to use a sequence activity model to guide directed evolution, one way relies on the regression coefficients for a particular mutation of a specific residue at a specific position, which reflect the mutation's contribution to protein activity. Specifically, a process of directed evolution could select the positions for mutation by evaluating the coefficients of the terms of the sequence-activity model to identify one or more of amino acids that contribute to substantial binding energy calculated by the virtual screening system. For instance, in this example, mutation 1 has a large positive coefficient, indicating that mutation 1 increases the activity to a large extent. See FIG. 6C. On the contrary, mutation 27 has a large negative coefficient, suggesting this mutation should be avoided in order to obtain a high activity as measured in FIG. 6C.

Example 2

Figure 7:
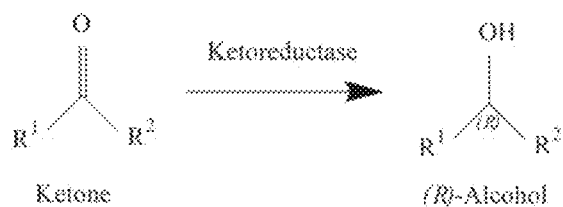
FIG. 7 shows quantities indicating conversion on X axis and selectivity on Y axis from virtually screening ketoreductase variants for enantioseletive production of (R)-1,1,1-trifluropropan-2-ol from 1,1,1-trifluropropan-2-one.
Figure 7:
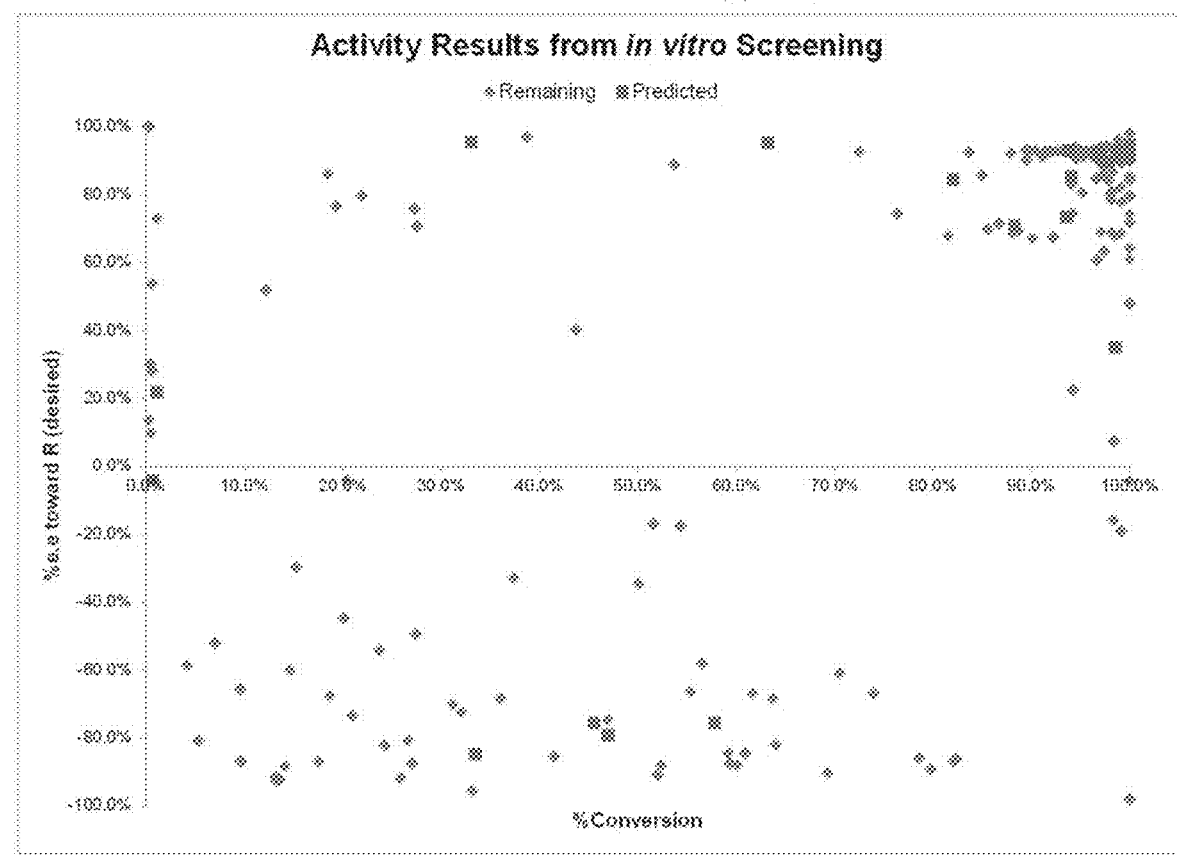

Example 2 provides an experimental validation of virtually screening ketoreductase variants for the R-enantiomer of a chiral alcohol from a pro-chiral ketone, as the reaction shown at the top of FIG. 7.

The process involved creating 3-dimensional homology models of two existing Panels of ketoreductase enzyme variants (96 wells format for each Panel) and virtually screening the 192 members of the ketoreductase Panels to select variants that (a) docked with the substrate in an active pose, (b) docked in a pro-R conformation, and (c) had favorable docking score.

The process identified 24 variants that can lead to active and energetically favorable poses, which may be prioritized for further development and screening. To validate the utility and validity of the virtual in silico screening results, the process also performed in vitro screening for all 192 members with a standard protocol, and substrate/products were detected with high-performance liquid chromatography (HPLC).

The results are shown in FIG. 7, where x-axis is % conversion calculated as (PeakArea$_{(R)-alcohol}$+PeakArea$_{(S)-alcohol}$)+(PeakArea$_{(R)-alcohol}$+PeakArea$_{(S)-alcohol}$+PeakArea$_{ketone}$)×100% and y-axis is % e.e. toward desired R product (an index of enantioselectivity) calculated as (Peak Area$_{(R)-alcohol}$−Peak Area$_{(S)-alcohol}$)+(Peak Area$_{(R)-alcohol}$+Peak Area$_{(S)-alcohol}$)×100%. The 24 variants prioritized by virtual screening were emphasized as Red Square and the remaining variants were highlighted as Blue Diamond. The results suggest: 1) virtual screening can help determine if a desired conversion is feasible with a set of enzyme variants before any in vitro screening; 2) a good amount of predicted variants indeed gave high activity (% Conversion) and enantioselectivity (% e.e.), despite the fact that such a small and flexible substrate is usually considered to be a challenge for modeling. Virtual screening can therefore filter out very unlikely reactions for in vitro screening and select less samples to test (24 vs. 192 in this case), which can lead to significant time- and cost-savings.

Example 3

Figure 8:
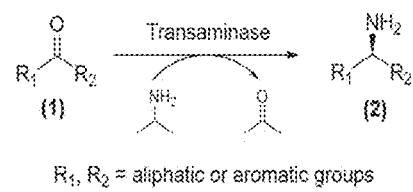
FIG. 8 shows quantities indicating conversion and hits (variants with certain level of improvement) from virtual directed evolution of P450 for regioseletive CH oxidation to C—OH.
Figure 8:
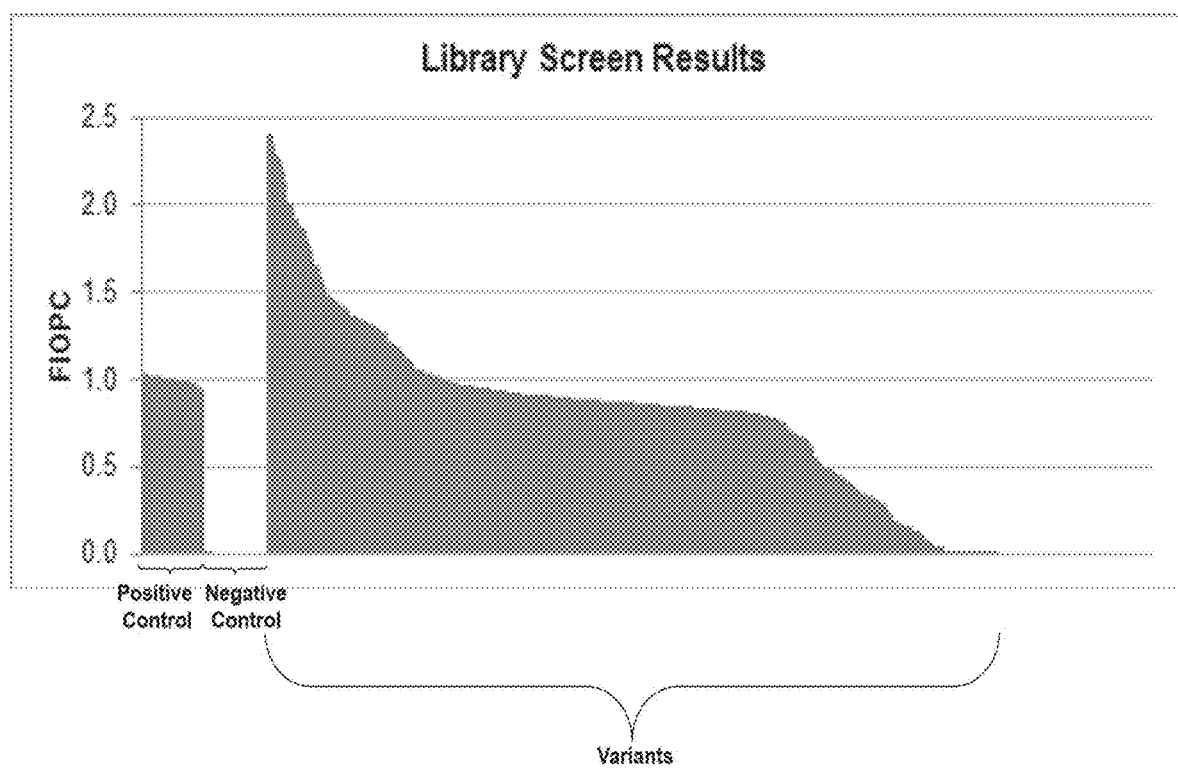

Example 3 provides an experimental validation of virtual directed evolution of transaminase for stereoselective C=O reduction to CH—NH$_2$, as the reaction shown at the top of FIG. 8.

The process involved creating 3-dimensional homology models of 228 virtual sequences from in silico saturated mutagenesis of 12 active site positions of the backbone (12 positions ×19 AA/position=228 variants, 1 mutation/variant) and virtually screening the 228 virtual variants to select variants that (a) docked with the substrate in an active pose, (b) docked in a conformation that lead to the desired stereoselectivity, and (c) had the lowest total binding energy among those that docked in active poses and in a targeted conformation.

The process then identified 12 variants or 12 mutations that can lead to active and energetically favorable poses. The 12 mutations were used to synthesize a library, which was screen in vitro. The in vitro screening was carried out for 360 variants (one or more than one mutations per variant) with a proprietary protocol. Substrate/products were detected with HPLC.

The results for the best variants from in vitro screening are shown in FIG. 8, where x-axis is the samples screened, and the y-axis is FIOPC defined as Fold Improvement Over Positive Control and calculated as (% Conversion$_{Variant}$−% Conversion$_{NegativeControl}$)÷(% Conversion$_{PositiveControl}$−% Conversion$_{NegativeControl}$)×100%. Positive Control is the backbone of virtual screening and in vitro screening and Negative Control is the empty vector without enzyme.

The in vitro library screening resulted in 13% of the variants having a FIOPC>1.5 and 5.3% with a FIOPC>2. The top hit had a FIOPC of 2.4. Virtual screening can therefore filter out deleterious mutations for in vitro screening and help design more targeted libraries, which can lead to significant time- and cost-savings. For example, if we had to do the saturated mutagenesis step in vitro, at least another 800 variants will need to be screened.

While the foregoing has been described in some detail for purposes of clarity and understanding, it will be clear to one skilled in the art from a reading of this disclosure that various changes in form and detail can be made without departing from the true scope of the disclosure. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method, implemented using a computer system that includes one or more processors and system memory, for screening a plurality of protein variants for interaction with a ligand, the method comprising:
    (a) providing, by the computer system, a structural model for each protein variant of the plurality of protein variants, wherein each structural model contains a three-dimensional computational representation of an active site of a protein variant, and wherein the plurality of protein variants comprises at least ten different variants;
    (b) for each protein variant of the plurality of protein variants, docking, by the computer system, a computational representation of the ligand to the three-dimensional computational representation of the active site of the protein variant, wherein docking (i) generates a plurality of poses of the ligand in the active site, wherein a pose comprises a position or orientation of the ligand with respect to the active site of the protein variant, and (ii) identifies energetically favorable poses of the ligand in the active site, wherein an energetically favorable pose is a pose having an energy that is favorable for binding between the ligand and the protein variant;
    (c) for at least one energetically favorable pose, determining, by the computer system, that the pose meets one or more constraints for the ligand to undergo a particular interaction with the protein variant, the one or more constraints comprise one or more ranges of position, distance, angle, and torsion of the ligand with respect to the active site of the protein variant, a cofactor of the protein variant, or an ideally positioned native ligand in the active site of the protein variant, and thereby determining that the at least one energetically favorable pose is an active pose; and
    (d) performing one or more rounds of directed evolution on at least one protein variant of the plurality of protein variants,
    wherein
        the at least one protein variant has an active site in which the ligand has the active pose, and
        the at least one protein variant has desired activity and/or selectivity in its interaction with the ligand, and
        the one or more rounds of directed evolution comprise synthesizing one or more polynucleotides encoding the at least one protein variant or portions thereof.
2. The method of claim 1, wherein the ligand is selected from a substrate, an intermediate of a substrate, a transition state of a substrate, a product of a substrate, an inhibitor of a protein variant, an agonist of a protein variant, and an antagonist of a protein variant.

3. The method of claim 1, wherein the protein is an enzyme.

4. The method of claim 1, wherein the computational representation of the ligand represents a species along a reaction coordinate, the species being selected from the ligand, a reaction intermediate of the ligand, or a transition state of the ligand.

5. The method of claim 1, wherein the plurality of protein variants comprise a panel of enzymes that can turn over multiple substrates and wherein members of the panel possess at least one mutation relative to a reference sequence.

6. The method of claim 5, wherein the at least one mutation is a single-residue mutation in the active site of the protein.

7. The method of claim 1, wherein the plurality of protein variants comprise one or more enzymes that can catalyze a chemical reaction selected from oxidoreduction, transferation, hydrolysis, isomerization, ligation, and chemical bond breaking by a reaction other than hydrolysis, oxidation, or reduction.

8. The method of claim 7, wherein the one or more enzymes are selected from the group consisting of oxidoreductase, transferase, hydrolase, isomerase, ligase, and lyase.

9. The method of claim 7, wherein the plurality of protein variants comprise one or more enzymes that can catalyze a chemical reaction selected from ketone reduction, transamination, oxidation, nitrile hydrolysis, imine reduction, enone reduction, acyl hydrolysis, and halohydrin dehalogenation.

10. The method of claim 9, wherein the one or more enzymes are selected from the group consisting of ketone reductase, transaminase, cytochrome P450, Baeyer-Villiger monooxygenase, monoamine oxidase, nitrilase, imine reductase, enone reductase, acylase, and halohydrin dehalogenase.

11. The method of claim 1, wherein the plurality of variants comprises members of library produced by one or more rounds of directed evolution in vitro and/or in silico.

12. The method of claim 1, wherein the plurality of poses of the ligand is obtained by one or more docking operations selected from the group consisting of: high temperature molecular dynamics, random rotation, refinement by grid-based simulated annealing, grid-based or full force field minimization, and any combinations thereof.

13. The method of claim 1, wherein the at least one protein variant is selected from variants determined to have large numbers of active poses by comparison to other variants.

14. The method of claim 1, wherein the at least one protein variant is selected by:
ranking variants by one or more of the following: numbers of active poses the variants have, docking scores of the active poses, and binding energies of the active poses; and
selecting the at least one protein variant based on its rank.

15. The method of claim 14, wherein the docking scores are based on van de Waals force and electrostatics interaction.

16. A method of claim 14, wherein the binding energies are based on one or more of the following: van der Waals force, electrostatic interaction, and solvation energy.

17. The method of claim 1, wherein performing one or more rounds of directed evolution comprises fragmenting and recombining the polynucleotides.

18. The method of claim 1, wherein performing one or more rounds of directed evolution comprises performing mutagenesis on the polynucleotides.

19. A system comprising: one or more processors, system memory, and a nucleic acid synthesizer;
wherein the one or more processors are configured to:
(a) provide a structural model for each protein variant of a plurality of protein variants, wherein each structural model contains a three-dimensional computational representation of an active site of a protein variant, and wherein the plurality of protein variants comprises at least ten different variants;
(b) for each protein variant of the plurality of protein variants, dock a computational representation of the ligand to the three-dimensional computational representation of the active site of the protein variant, wherein docking (i) generates a plurality of poses of the ligand in the active site, wherein a pose comprises a position or orientation of the ligand with respect to the active site of the protein variant, and (ii) identifies energetically favorable poses of the ligand in the active site, wherein an energetically favorable pose is a pose having an energy that is favorable for binding between the ligand and the protein variant; and
(c) for at least one energetically favorable pose, determine that the pose meets one or more constraints for the ligand to undergo a particular interaction with the protein variant, the one or more constraints comprise one or more ranges of position, distance, angle, and torsion of the ligand with respect to the active site of the protein variant, a cofactor of the protein variant, or an ideally positioned native ligand in the active site of the protein variant, and thereby determine that the at least one energetically favorable pose is an active pose,
wherein the nucleic acid synthesizer is configured to:
synthesize at least one polynucleotide encoding at least a portion of at least one protein variant of the plurality of protein variants, wherein the at least one protein variant has an active site in which the ligand has the active pose, and wherein the at least one protein variant has desired activity and/or selectivity in its interaction with the ligand.

20. A computer program product comprising one or more computer-readable non-transitory storage media having stored thereon computer-executable instructions that, when executed by one or more processors of a computer system, cause the computer system to implement a method for virtual screening of enzyme variants, the instructions comprising:
(a) providing a structural model for each protein variant of a plurality of protein variants, wherein each structural model contains a three-dimensional computational representation of an active site of a protein variant, and wherein the plurality of protein variants comprises at least ten different variants;
(b) for each protein variant of the plurality of protein variants, docking a computational representation of the ligand to the three-dimensional computational representation of the active site of the protein variant, wherein docking (i) generates a plurality of poses of the ligand in the active site, wherein a pose comprises a position or orientation of the ligand with respect to the active site of the protein variant, and (ii) identifies energetically favorable poses of the ligand in the active site, wherein an energetically favorable pose is a pose having an energy that is favorable for binding between the ligand and the protein variant;

(c) for at least one energetically favorable pose, determining that the pose meets one or more constraints for the ligand to undergo a particular interaction with the protein variant, the one or more constraints comprise one or more ranges of position, distance, angle, and torsion of the ligand with respect to the active site of the protein variant, a cofactor of the protein variant, or an ideally positioned native ligand in the active site of the protein variant, and thereby determining that the at least one energetically favorable pose is an active pose; and (d) controlling a nucleic acid synthesizer to synthesize one or more polynucleotides encoding at least one protein variant or portions thereof, wherein the at least one protein variant has an active site in which the ligand has the active pose, and the at least one protein variant has desired activity and/or selectivity in its interaction with the ligand.

* * * * *